(12) United States Patent
Savage

(10) Patent No.: US 9,943,614 B2
(45) Date of Patent: Apr. 17, 2018

(54) CATIONIC STEROID ANTIMICROBIAL DIAGNOSTIC, DETECTION, SCREENING AND IMAGING METHODS

(75) Inventor: Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 424 days.

(21) Appl. No.: 13/000,010

(22) PCT Filed: Jun. 16, 2009

(86) PCT No.: PCT/US2009/047485
§ 371 (c)(1),
(2), (4) Date: Dec. 17, 2010

(87) PCT Pub. No.: WO2010/036427
PCT Pub. Date: Apr. 1, 2010

(65) Prior Publication Data
US 2011/0091376 A1  Apr. 21, 2011

Related U.S. Application Data

(60) Provisional application No. 61/132,361, filed on Jun. 17, 2008.

(51) Int. Cl.
*A61K 51/04* (2006.01)
(52) U.S. Cl.
CPC ................. *A61K 51/0493* (2013.01)
(58) Field of Classification Search
None
See application file for complete search history.

(56) References Cited

U.S. PATENT DOCUMENTS

| | | | |
|---|---|---|---|
| 4,248,236 A | 2/1981 | Linder | |
| 4,661,341 A | 4/1987 | Benedict et al. | |
| 4,723,950 A | 2/1988 | Lee | |
| 4,765,855 A | 8/1988 | Geoffroy-Dechaume et al. | |
| 4,842,593 A | 6/1989 | Jordan et al. | |
| 4,972,848 A | 11/1990 | DiDomenico | |
| 5,025,754 A | 6/1991 | Plyler | |
| 5,286,479 A | 2/1994 | Garlich et al. | |
| 5,310,545 A | 5/1994 | Eisen | |
| 5,356,630 A | 10/1994 | Laurencin et al. | |
| 5,364,650 A | 11/1994 | Guthery | |
| 5,380,839 A | 1/1995 | McCall et al. | |
| 5,552,057 A | 9/1996 | Hughes et al. | |
| 5,624,704 A | 4/1997 | Darouiche et al. | |
| 5,721,359 A | 2/1998 | Dunn et al. | |
| 6,117,332 A | 9/2000 | Hatch et al. | |
| 6,228,393 B1 | 5/2001 | DiCosmo et al. | |
| 6,329,488 B1 | 12/2001 | Terry et al. | |
| 6,350,738 B1 | 2/2002 | Savage et al. | |
| 6,486,148 B2 | 11/2002 | Savage et al. | |
| 6,562,318 B1 | 5/2003 | Filler | |
| 6,582,713 B2 | 6/2003 | Newell et al. | |
| 6,673,771 B1 | 1/2004 | Greene et al. | |
| 6,767,904 B2 | 7/2004 | Savage et al. | |
| 6,803,066 B2 | 10/2004 | Traeder | |
| 6,872,303 B2 | 3/2005 | Knapp et al. | |
| 6,939,376 B2 | 9/2005 | Shulze et al. | |
| 7,282,214 B2 | 10/2007 | Wilcox et al. | |
| 7,381,439 B2 | 6/2008 | Hilgren et al. | |
| 7,598,234 B2 | 10/2009 | Savage et al. | |
| 7,659,061 B2 | 2/2010 | Hendl et al. | |
| 7,754,705 B2 | 7/2010 | Savage et al. | |
| 7,854,941 B2 | 12/2010 | Urban et al. | |
| 7,993,903 B2 | 8/2011 | Hayakawa et al. | |
| 8,211,879 B2 | 7/2012 | Savage et al. | |
| 8,529,681 B1 | 9/2013 | Hibbs et al. | |
| 8,623,416 B2 | 1/2014 | Zasloff et al. | |
| 8,691,252 B2 | 4/2014 | Savage | |
| 8,784,857 B2 | 7/2014 | Savage | |
| 8,787,857 B2 | 7/2014 | Savage | |
| 9,527,883 B2 | 12/2016 | Savage et al. | |
| 2002/0091278 A1 | 7/2002 | Savage et al. | |
| 2003/0018306 A1 | 1/2003 | Bucay-Couto et al. | |
| 2003/0099717 A1 | 5/2003 | Cabrera | |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

Ding et al. Origins of cell selectivity of cationic steroid antibiotics. 2004 J. Am. Chem. Soc. 126: 13642-13648.*
Britton et al. Imaging bacterial infection with (99m)Tc-ciprofloxacin (Infecton). 2002 J. Clin. Pathol. 55: 817-823.*
Bridot et al. Hybrid gadolinium oxide nanoparticles: multimodal contrast agents for in vivo imaging. 2007 J. Am. Chem. Soc. 129: 5076-5084. Published online Mar. 31, 2007.*
Welling et al. Radiochemical and biological characteristics of 99mTc-UBI 29-41 for imaging of bacterial infections. 2002 Nucl. Med. Biol. 29: 413-422.*
Meléndez-Alafort et al. Lys and Arg in UBI: a specific site for a stable Tc-99m complex? 2003 Nucl. Med. Biol. 30: 605-615.*
Lankinen et al. 68Ga-DOTA-peptide targeting VAP-1 for in vivo evaluation of inflammatory and infectious bone conditions. In: 52nd annual meeting of the Orthopaedic Research Society; Mar. 19-22, 2006; Chicago, IL. Paper No. 0237.*

(Continued)

*Primary Examiner* — Michael G Hartley
*Assistant Examiner* — Jennifer Lamberski
(74) *Attorney, Agent, or Firm* — Workman Nydegger

(57) ABSTRACT

The invention relates to diagnostic, detection, screening and imaging methods. In various embodiments, methods of diagnosis, detection, screening and imaging include administering a cationic steroid antimicrobial or CSA to a subject having or at risk of having an infection or a hyperproliferative disorder (e.g., a tumor, cancer or neoplasia) in an amount effective to diagnose or detect the infection or the hyperproliferative disorder (e.g., a tumor, cancer or neoplasia) in the subject. In a particular aspect, a detectable CSA, namely CSA-13 labeled with $^{99m}$Tc is used to detect the presence of an infection.

13 Claims, 11 Drawing Sheets

(56) References Cited

U.S. PATENT DOCUMENTS

| | | | |
|---|---|---|---|
| 2004/0009227 A1 | 1/2004 | Yao | |
| 2004/0018154 A1 | 1/2004 | Pan | |
| 2004/0058974 A1 | 3/2004 | Courtney et al. | |
| 2004/0071781 A1 | 4/2004 | Chattopadhyay et al. | |
| 2004/0170563 A1* | 9/2004 | Meade | A61K 47/48076 424/9.35 |
| 2004/0259445 A1 | 12/2004 | Hilfenhaus et al. | |
| 2005/0032765 A1 | 2/2005 | Savage et al. | |
| 2005/0075321 A1 | 4/2005 | Ahlem et al. | |
| 2005/0244468 A1 | 11/2005 | Huang et al. | |
| 2005/0267051 A1 | 12/2005 | Lee et al. | |
| 2006/0062742 A1 | 3/2006 | Davis et al. | |
| 2006/0269485 A1 | 11/2006 | Friedman et al. | |
| 2007/0106393 A1 | 5/2007 | Miles et al. | |
| 2007/0134292 A1 | 6/2007 | Suokas et al. | |
| 2007/0190066 A1 | 8/2007 | Savage et al. | |
| 2007/0190067 A1 | 8/2007 | Savage et al. | |
| 2007/0190558 A1 | 8/2007 | Savage et al. | |
| 2008/0174035 A1 | 7/2008 | Winterton | |
| 2008/0188819 A1 | 8/2008 | Kloke et al. | |
| 2008/0279944 A1 | 11/2008 | Sawhney | |
| 2009/0016973 A1 | 1/2009 | Ratcliff et al. | |
| 2009/0054295 A1 | 2/2009 | Vicari et al. | |
| 2009/0068122 A1 | 3/2009 | Pilch et al. | |
| 2009/0099531 A1 | 4/2009 | Griesbach, III | |
| 2009/0252781 A1 | 10/2009 | Sawhney et al. | |
| 2009/0324517 A1 | 12/2009 | Kline | |
| 2010/0092398 A1 | 4/2010 | Reynolds | |
| 2010/0226884 A1 | 9/2010 | Chang et al. | |
| 2010/0310478 A1 | 12/2010 | Fitzgerald et al. | |
| 2010/0330086 A1 | 12/2010 | Savage et al. | |
| 2011/0091376 A1 | 4/2011 | Savage | |
| 2011/0123624 A1 | 5/2011 | Zasloff | |
| 2011/0135742 A1 | 6/2011 | Kim et al. | |
| 2012/0088733 A1 | 4/2012 | Kim et al. | |
| 2012/0107382 A1 | 5/2012 | Savage et al. | |
| 2013/0022651 A1 | 1/2013 | Savage | |
| 2013/0053507 A1 | 2/2013 | Savage | |
| 2013/0234842 A1 | 9/2013 | Genberg et al. | |
| 2013/0236619 A1 | 9/2013 | Savage | |
| 2013/0243823 A1 | 9/2013 | Genberg et al. | |
| 2013/0243840 A1 | 9/2013 | Savage et al. | |
| 2013/0245760 A1 | 9/2013 | Savage et al. | |
| 2013/0280312 A1 | 10/2013 | De Szalay | |
| 2013/0280391 A1 | 10/2013 | Savage | |
| 2014/0107090 A1 | 4/2014 | Beus et al. | |
| 2014/0194401 A1 | 7/2014 | Genberg et al. | |
| 2014/0219914 A1 | 8/2014 | Govindan et al. | |
| 2014/0271761 A1 | 9/2014 | Savage et al. | |
| 2014/0274913 A1 | 9/2014 | Savage et al. | |
| 2014/0315873 A1 | 10/2014 | Beus et al. | |
| 2014/0363780 A1 | 12/2014 | Vazquez et al. | |
| 2014/0369941 A1 | 12/2014 | Vazquez et al. | |
| 2015/0140063 A1 | 5/2015 | Savage | |
| 2015/0203527 A1 | 7/2015 | Savage | |
| 2015/0239928 A1 | 8/2015 | Savage | |
| 2015/0258121 A1 | 9/2015 | Darien et al. | |
| 2015/0258122 A1 | 9/2015 | Beus et al. | |
| 2015/0258123 A1 | 9/2015 | Savage et al. | |
| 2016/0193232 A1 | 3/2016 | Beus et al. | |
| 2016/0199790 A1 | 3/2016 | Beus et al. | |
| 2016/0311850 A1 | 10/2016 | Savage et al. | |
| 2016/0311851 A1 | 10/2016 | Savage et al. | |
| 2017/0035677 A1 | 2/2017 | Vazquez et al. | |
| 2017/0080128 A1 | 3/2017 | Genberg et al. | |
| 2017/0137459 A1 | 5/2017 | Savage | |
| 2017/0210776 A1 | 7/2017 | Savage | |

FOREIGN PATENT DOCUMENTS

| | | |
|---|---|---|
| EP | 0341951 | 11/1989 |
| EP | 1208844 | 5/2002 |
| EP | 1219631 | 7/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002558093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 1995024415 | 9/1995 |
| WO | WO9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO 2003015757 | 2/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2009 |
| WO | WO 2009079066 | 6/2009 |
| WO | WO2009144708 | 12/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO 2013109236 | 7/2013 |

OTHER PUBLICATIONS

Fichna et al. Synthesis of target-specific radiolabeled peptides for diagnostic imaging. 2003 Bioconjug. Chem. 14: 3-17.*

Massoud et al. Molecular imaging in living subjects: seeing fundamental biological processes in a new light. 2003 Genes Dev. 17: 545-580.*

Li et al. Incremental conversion of outer-membrane permeabilizers into potent antibiotics for gram-negative bacteria. 1999 J. Am. Chem. Soc. 121: 931-940.* de Cuyper et al. Surface functionalization of magnetoliposomes in view of improving iron oxide-based magnetic resonance imaging contrast agents: anchoring of gadolinium ions to a lipophilic chelate. 2007 Anal. Biochem. 367: 266-273. Published online May 10, 2007.*

Winter et al. Improved paramagnetic chelate for molecular imaging with MRI. 2005 J. Magn. Magn. Mater. 293: 540-545.*

U.S. Appl. No. 13/783,007, filed Mar. 1, 2013, Savage.
U.S. Appl. No. 14/288,126, filed May 27, 2014, Savage et al.
U.S. Appl. No. 14/339,342, filed Jul. 23, 2014, Vazquez et al.
U.S. Appl. No. 14/341,304, filed Jul. 25, 2014, Savage et al.
U.S. Appl. No. 14/364,283, filed Jul. 29, 2014, Vazquez et al.
U.S. Appl. No. 14/398,094, filed Oct. 30, 2014, Savage et al.
U.S. Appl. No. 14/515,858, filed Oct. 16, 2014, Savage et al.

P. B. Savage, et al., "Thin Films Containing Ceragenins Prevent Biofilm Formation on Endotracheal Tubes", 9th International Federation of Infection Control Congress, Oct. 14, 2008, pp. 1-1.

Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.

K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.

Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.

(56) References Cited

OTHER PUBLICATIONS

Savage, et al., "Antibacterial Activities of Thin Films Containing Ceragenins", Microbial Surfaces: Structure, Interactions and Reactivity, ACS, May 30, 2008, pp. 65-78.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Alhanout K et al: "Squalamine as an example of a new potent antimicrobial agents class: a critical review.", Current Medicinal Chemistry 2010, vol. 17, No. 32, 2010, pp. 3909-3917.
International Search Report for PCT Application No. PCT/US2012/047750, dated Oct. 5, 2012, Filed Date: Sep. 27, 2012, 3 pages.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Paul B. Savage, et al: "Antibacterial Properties of cationic steroid antibiotics", FEMS Microbiology Letters, vol. 217, Nov. 2002, pp. 1-7.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
International Search Report for PCT Application No. PCT/US2013/038090, dated Jul. 24, 2013.
Steeneveld, et al., "Cow-specific treatment of clinical mastitis: an economic approach", Journal of Dairy Science vol. 94, Jan. 2011, pp. 174-188.
International Search Report for PCT Application No. PCT/US2012/055248 dated Feb. 14, 2013.
International Search Report for PCT Application No. PCT/US2012/055244 dated Dec. 5, 2012.
U.S. Appl. No. 13/554,957, filed Apr. 1, 2014, Office Action.
U.S. Appl. No. 13/554,957, filed Aug. 1, 2014, Notice of Allowance.
U.S. Appl. No. 13/594,608, filed Jan. 30, 2014, Office Action.
U.S. Appl. No. 13/594,612, filed May 15, 2014, Office Action.
U.S. Appl. No. 13/615,324, filed Jan. 30, 2014, Office Action.
U.S. Appl. No. 13/554,930, filed Jul. 11, 2014, Office Action.
U.S. Appl. No. 13/783,131, filed Oct. 23, 2014, Office Action.
U.S. Appl. No. 14/056,122, filed Sep. 3, 2014, Office Action.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl file/o10062704 sl.pdf.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
International Search Report for PCT Application No. PCT/US2011/059225 dated Jan. 31, 2012.
U.S. Appl. No. 13/288,902, filed Nov. 3, 2011, Restriction Requirement dated Jun. 21, 2012.
U.S. Appl. No. 13/288,902, filed Nov. 3, 2011, Office Action dated Nov. 7, 2012.
U.S. Appl. No. 13/288,902, filed Nov. 3, 2011, Notice of Allowance dated Aug. 9, 2013.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
International Search Report for PCT Application No. PCT/US2009/047485 dated Feb. 17, 2010.
U.S. Appl. No. 13/000,010, filed Dec. 4, 2012, Restriction Requirement.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.
U.S. Appl. No. 13/783,007, filed Mar. 1, 2013, Restriction Requirement dated Mar. 31, 2015.
U.S. Appl. No. 14/257,776, filed Apr. 21, 2014, Office Action dated Apr. 16, 2015.
U.S. Appl. No. 14,694,028, filed Apr. 23, 2015, Beus et al.
U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.
U.S. Appl. No. 14/875,953, filed Oct. 6, 2015, Savage.
U.S. Appl. No. 14/926,738, filed Oct. 29, 2015, Vazquez et al.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 2004.
International Search Report for PCT Application No. PCT/US2014/034986 dated Aug. 28, 2014.
International Search Report for PCT Application No. PCT/US2013/065510, dated Apr. 30, 2015.

(56) References Cited

OTHER PUBLICATIONS

International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Suzuki et al., "Molecular Genetics of Plant Sterol Backbone Synthesis", 2007; Lipids; 42: 47-54.
Van Den Bogaard et al., "Antibiotic Usage in Animals: Impact on Bacterial Resistance and Public Health"; 1999; Drugs; 58 (4): 589-607.
Zanger et al., "Structure-Activity Relationship and Drug Design", Remington's Pharmaceutical Sciences, Chapter 27, 16th Edition, 1980, pp. 420-425.
U.S. Appl. No. 15/454,135, filed Mar. 9, 2017, Savage et al.
U.S. Appl. No. 15/585,632, filed May 3, 2017, Savage et al.
Bush, "Staphylococcal Infections", Merck Manuals Professional Edition, http://www.merckmanuals.com/professional/infectious-diseases/gram-positive-cocci/staphylococcal-infections, 2017.
Elder et al., "The Utility of Sulfonate Salts in Drug Development", Journal of Pharmaceutical Sciences 99(7): 2948-2961, 2010.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824, 2002.
Louw et al., "Recueil des Travaux Chimiques des Pays-Bas et la Belgique", vol. 73, pp. 667-676, 1954.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO—Published Dec. 20, 2007).
Pycock, "The Dirty Mare", https://www.equine-reproduction.com/articles/DirtyMare.shtml, 2003.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Papo et al., "Host peptides as new weapons in cancer treatment", CMLS Cell. Mol. Life Sci. 62 (2005), 784-790.
Cipolla et al., "Inhaled antibiotics to treat lung infection", Pharm Pat Anal., Sep. 2013.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Survey Research on Behcet's Disease, 2005 to 2007 Comprehensive Survey Reports, 2008, pp. 34-39.

\* cited by examiner

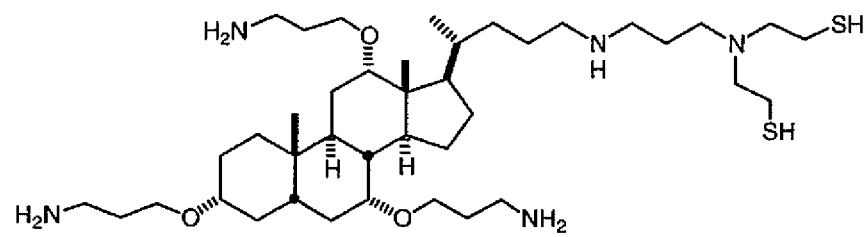
CSA-107
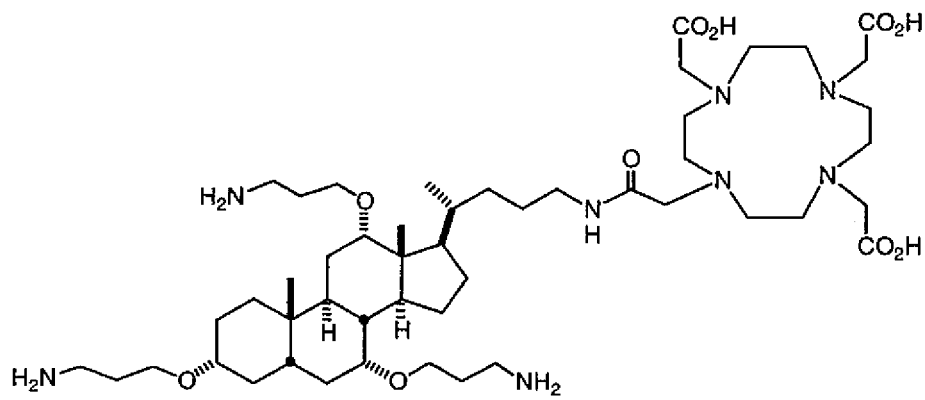
CSA-110
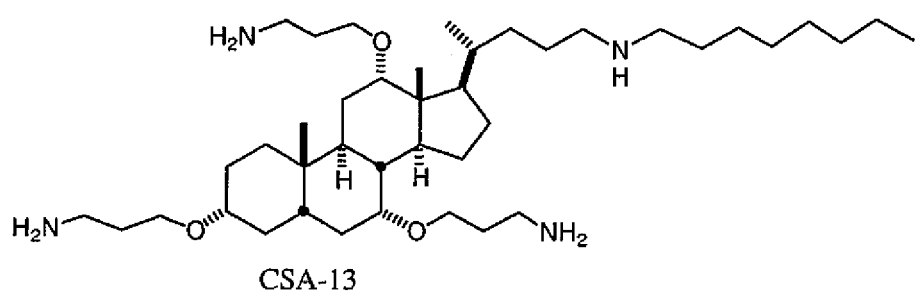
CSA-13
FIG. 1

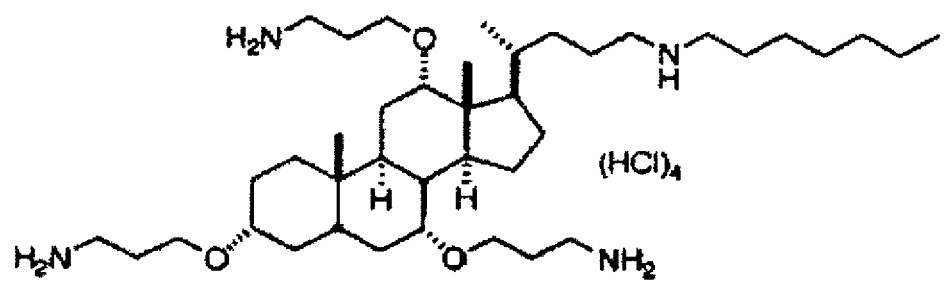
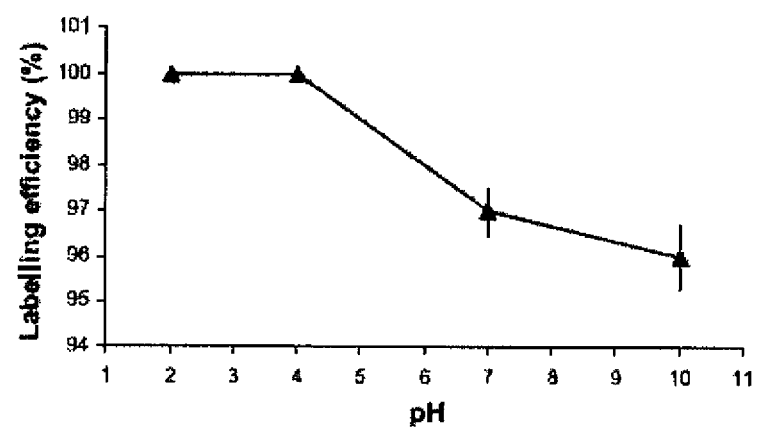
Fig. 2.

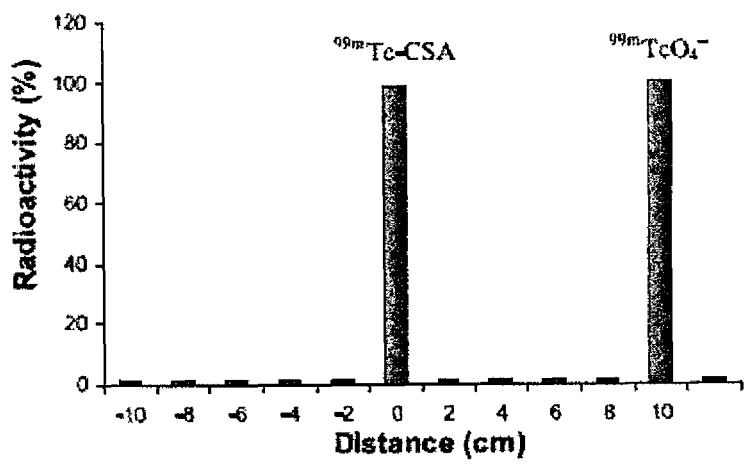
Fig. 5.
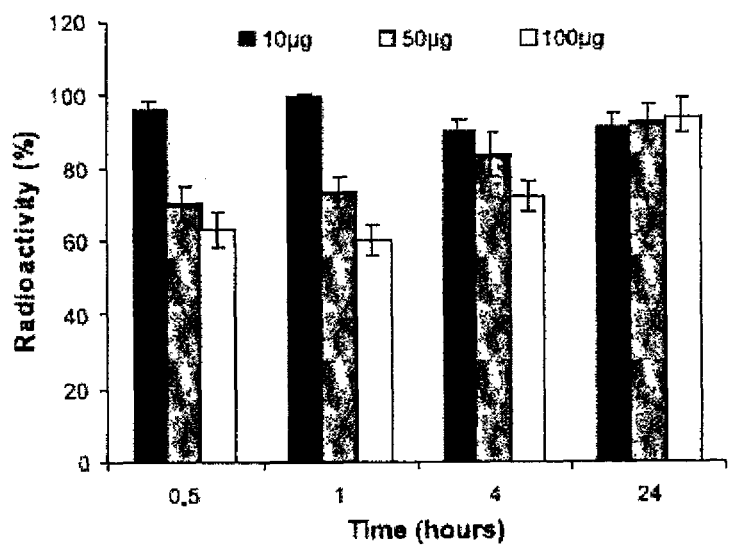
Fig. 6. *In-vi*

140

CSA-31

132

352　n = 1
353　n = 2
354　n = 3

| | | |
|---|---|---|
| 341 | n = 1, | R = -(CH$_2$)$_7$CH$_3$ |
| 342 | n = 2, | R = -(CH$_2$)$_7$CH$_3$ |
| 343 | n = 3 | R = -(CH$_2$)$_7$CH$_3$ |
| 324 | n = 1 | R = -CH$_2$CH$_2$N$^+$(CH$_3$)$_3$ |
| 325 | n = 2 | R = -CH$_2$CH$_2$N$^+$(CH$_3$)$_3$ |
| 326 | n = 3 | R = -CH$_2$CH$_2$N$^+$(CH$_3$)$_3$ |
| 327 | n = 1 | R = -H |

CATIONIC STEROID ANTIMICROBIAL DIAGNOSTIC, DETECTION, SCREENING AND IMAGING METHODS

RELATED APPLICATIONS

This application is the National Phase of International Application No. PCT/US2009/047485, filed Jun. 16, 2009 which designated the U.S. and that International Application was published under PCT Article 21(2) in English, and claims priority to U.S. Provisional Application No. 61/132,361, filed Jun. 17, 2008, all of which applications are incorporated herein by reference in their entirety.

TECHNICAL FIELD

The invention relates to diagnostic, detection, screening and imaging methods. In various embodiments, methods of the invention include administering a cationic steroid antimicrobial or CSA to a subject having or at risk of having an infection or a hyperproliferative disorder (e.g., a tumor, cancer or neoplasia) in an amount effective to diagnose or detect, diagnose, screen for or image the infection or the hyperproliferative disorder (e.g., a tumor, cancer or neoplasia) in the subject.

INTRODUCTION

Ceragenins (cationic steroid antimicrobials or CSAs) are synthetically produced small molecules that display broad spectrum antibacterial activity. These compounds are derived from a steroid backbone appended with amino groups, amino acids and other chemical groups (Savage P. B., et al., *FEMS Microbiology Letters* (2002) 217:1). Specific ceragenins are highly bactericidal and while others effectively permeabilize the outer membranes of Gram-negative bacteria (Li C., et al., *Antimicrob Agents Chemother* 43:1347 (1999), (Schmidt E. J., et al., *J Antimicrob Chemother* 47:671 (2001)). Ceragenins exhibit various levels of selectivity for membranes of eukaryotes vs. prokaryotes (Ding B., et al., *J Med Chem* 45:663 (2002)). These compounds have a net positive charge that is electrostatically attracted to the negatively charged cell membranes of certain viruses, fungi and bacteria.

Ceragenins have a high binding affinity for such membranes (including lipid A) and are able to rapidly disrupt the target membranes leading to rapid cell death. While ceragenins have a mechanism of action that is also seen in antimicrobial peptides, which form part of the body's innate immune system, they avoid many of the difficulties associated with their use as medicines. They are simple to prepare and are not substrates for proteases. In vitro studies show that ceragenins are active against a wide range of viral, fungal, and bacterial targets including those resistant to current therapies. The antibacterial properties of a ceragenin, CSA-13 (FIG. 1) (Savage P. B., et al., *FEMS Microbiology Letters* (2002) 217:1), against vancomycin-resistant *Staphylococcus aureus*, vancomycin intermediate resistant *S. aureus* strains, vancomycin-resistant Enterococci, and methicillin-resistant *S. aureus*, as well as key Gram-negative pathogens such as *Pseudomonas aeruginosa* and *Escherichia coli*, and bioterrorism surrogate strains for Anthrax, Listeria and plague have also been reported. CSA-13 also inhibit HIV infection of primary human CD4+ T cells, the virus's in vivo targets. The reports indicate that CSA-13 most likely attacks the viral membrane and disrupts the virus from interacting with its target cells, similar to some of the known microbicidal peptides. This is important, as a compound that targets the viral membrane is likely to be effective against all strains of the virus, regardless of mutations, as the viral membrane remains unchanged.

Ceragenin CSA-13 is not to be toxic to epithelial cells, keratinocytes and fibroblasts at concentrations significantly higher than those required for bactericidal and virucidal activity. CSA-13 is indefinitely stable as a solid and in solution form and may be stored at room temperature or in refrigerator (Savage P. B., et al., *Eur J Org Chem* 759 (2002)).

SUMMARY

The invention provides methods and kits for diagnosis, detection, screening and imaging, in vitro, ex vivo and in vivo. Methods include, among other things, administering a cationic steroid antimicrobial or CSA (e.g., a detectable or labeled CSA) to a subject having or at risk of having an infection or a hyperproliferative disorder (e.g., a tumor, cancer or neoplasia) in an amount effective to diagnose, detect, screen for or image the infection or the hyperproliferative disorder (e.g., a tumor, cancer or neoplasia) in the subject. A direct method of labeling of ceragenins with $^{99m}$Tc is disclosed which is simple, rapid, and efficient. The labeled ceragenin, CSA-13 (FIG. 1), contains multiple amine groups, and it is expected that labeling occurs via association with one or more of the amine groups.

DESCRIPTION OF THE DRAWINGS

FIG. 1: Structures of CSA-13, CSA-107 and CSA-110.

FIG. 2: Effect of pH on labeling efficiency of $^{99m}$Tc-CSA (n=4 per study).

FIG. 5: Paper electrophoresis of $^{99m}$Tc-CSA and $^{99m}$TcO$_4^-$ in sodium phosphate buffer of pH: 6.8 using Whatman 1 as support. The samples were run at constant voltage of 300V for 1 hour.

FIG. 6: In-vitro binding of $^{99m}$Tc-CSA to viable *S. aureus* (n=4 per study).

DETAILED DESCRIPTION

Figure 3:
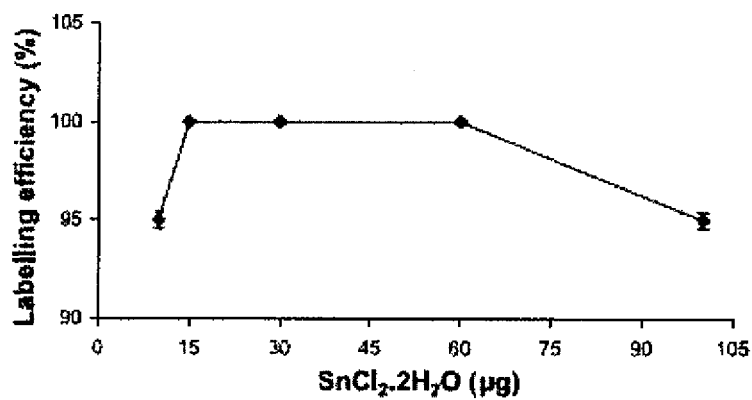
FIG. 3: Effect of reducing agent SnCL.2H$_2$O amount on the labeling efficiency of $^{99m}$Tc-CSA (n=4 per study).

In accordance with the invention, there are provided methods and kits for diagnosis, detection, screening and imaging, infection or a hyperproliferative disorder (e.g., a tumor, cancer or neoplasia, or metastasis thereof) in vitro, ex vivo and in vivo. In one embodiment, a method of the invention includes administering a detectably labeled CSA to the subject under conditions whereby the labeled CSA can bind to an infection, and detecting the labeled CSA in the subject to ascertain the presence or absence of an infection, thereby detecting the infection, or diagnosing the subject as having or not having an infection. In another embodiment, a method of the invention includes administering a detectably labeled CSA to the subject under conditions whereby the labeled CSA can bind to a tumor, cancer or neoplasia, and detecting the labeled CSA in the subject to ascertain the presence or absence of a tumor, cancer or neoplasia, thereby detecting a tumor, cancer or neoplasia, or diagnosing the subject as having or not having a tumor, cancer or neoplasia. In an additional embodiment, a method of the invention includes administering a detectably labeled CSA to the subject under conditions whereby the labeled CSA can bind to an infection, and imaging the labeled CSA in the subject to ascertain the presence or absence of an infection. In a further embodiment, a method of the invention includes administering a detectably labeled CSA to the subject under conditions whereby the labeled CSA can bind to a tumor, cancer or neoplasia, and imaging the labeled CSA in the subject to ascertain the presence or absence of a tumor, cancer or neoplasia.

The invention methods include, among other things, in vitro, ex vivo and in vivo methods. Subjects can be contacted with, administered, or delivered a compound (e.g., one or more CSAs) in order to diagnose, detect, screen for or image an infection, or a tumor, cancer or neoplasia, or a metastasis thereof. A sample, such as a biological sample, can be contacted with, administered, or delivered a compound (e.g., one or more CSAs) in order to diagnose, detect, screen for or image an infection, or a tumor, cancer or neoplasia, or a metastasis thereof.

The term "contact" and grammatical variations thereof means the subject or a sample is given or delivered a CSA under conditions allowing a physical interaction between the CSA and an infection or a hyperproliferative disorder (e.g., a tumor, cancer or neoplasia, or metastasis thereof) in vitro, ex vivo and in vivo. The term "administering" includes delivery to a subject in which the CSA can physically interact with an infection or a hyperproliferative disorder (e.g., a tumor, cancer or neoplasia, or metastasis thereof) in vitro, ex vivo and in vivo.

In particular embodiments of the methods and kits of the invention, a CSA is any of CSA-1 through CSA-400. In more particular aspects, a CSA is selected from: CSA-7, CSA-8, CSA-10, CSA-11, CSA-13, CSA-15, CSA-17, CSA-21, CSA-25, CSA-26, CSA-31, CSA-46, CSA-54 and CSA-59, CSA-107 and CSA-110. In other embodiments, a CSA does not have a charged group at position C24 or a CSA has a hydrophobic moiety at position C24 (e.g., a lipid). In additional embodiments, a CSA has a charged group at position C7. In further embodiments, a CSA comprises a multimer (e.g., a dimer, trimer, tetramer or higher order polymer). In yet additional embodiments, a CSA has a shorter tether length between the steroid scaffold and any amine group at positions C3, C7 or C12, relative to the tether length between the steroid scaffold and any amine group at positions C3, C7 or C12 of CSA-7, CSA-8, CSA-10, CSA-11, CSA-13, CSA-15, CSA-17, CSA-21, CSA-25, CSA-26, CSA-31, CSA-46, CSA-54 or CSA-59.

Detectable labels include labels suitable for diagnosis, detection, screening or imaging. A detectable label can be included or within in the structure of the CSA. As the structure of CSAs includes carbon, hydrogen, nitrogen, oxygen, sulfur, etc., radioisotopes of any of carbon, hydrogen, nitrogen, oxygen, sulfur, etc., can be included or within in a CSA structure such that the CSA is detectable labelled.

A detectable label can also be covalently linked or conjugated to the CSA. Non-limiting exemplary detectable labels include a radioactive material, such as a radioisotope, a metal or a metal oxide. In particular embodiments, a radioisotope can be one or more of: C, N, O, H, S, Cu, Fe, Ga, Ti, Sr, Y, Tc, In, Pm, Gd, Sm, Ho, Lu, Re, At, Bi or Ac. In additional embodiments, radioisotope can be one or more of: $^{3}H$, $^{10}B$, $^{18}F$, $^{11}C$, $^{14}C$, $^{13}N$, $^{18}O$, $^{15}O$, $^{32}P$, $^{35}S$, $^{35}Cl$, $^{45}Ti$, $^{46}Sc$, $^{51}Cr$, $^{52}Fe$, $^{59}Fe$, $^{57}Co$, $^{60}Cu$, $^{61}Cu$, $^{62}Cu$, $^{64}Cu$, $^{67}Cu$, $^{67}Ga$, $^{68}Ga$, $^{72}As$, $^{76}Br$, $^{77}Br$, $^{81m}Kr$, $^{82}Rb$, $^{85}Sr$, $^{89}Sr$, $^{86}Y$, $^{90}Y$, $^{95}Nb$, $^{94m}Tc$, $^{99m}Tc$, $^{97}Ru$, $^{103}Ru$, $^{105}Rh$, $^{109}Cd$, $^{111}In$, $^{113}Sn$, $^{113m}In$, $^{114}In$, $^{140}La$, $^{141}Ce$, $^{149}Pm$, $^{153}Gd$, $^{157}Gd$, $^{153}Sm$, $^{161}Tb$, $^{166}Dy$, $^{166}Ho$, $^{169}Er$, $^{169}Y$, $^{175}Yb$, $^{177}Lu$, $^{186}Re$, $^{188}Re$, $^{201}Tl$, $^{203}Pb$, $^{211}At$, $^{212}Bi$ or $^{225}Ac$. In more particular embodiments, a radionuclide includes technetium and rhenium isotopes, more specifically, for example, technetium-99m, rhenium-186 and rhenium-188.

Radionuclides include, but are not limited to, isotopes emitting alpha, beta or gamma radiation. In diagnostic, screening, detection and imaging methods, typically a beta emitter is employed. Non-limiting examples of beta emitters include cesium-137, cobalt-60, radium-226, and technetium-99m.

CSAs typically include several basic sites (oxygen, sulfur, and nitrogen lone pairs) which are suitable for binding cationic radionuclides and metals. This allows easy and optionally reversible complexation of the CSA with the radionuclide or metal. Thus, detectably labeled CSAs can include cationic radionuclides and cationic metals.

Additional non-limiting exemplary detectable labels include a metal or metal oxide. In particular embodiments, a metal or metal oxide is one or more of: gold, silver, copper, boron, manganese, gadolinium, iron, chromium, barium, europium, erbium, praseodynium, indium, or technetium. In additional embodiments, a metal oxide includes one or more of: Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), or Er(III). Metals and oxides include crystals.

A label can also be a contrast agent (e.g., gadolinium; manganese; barium sulfate; an iodinated or noniodinated agent; an ionic agent or nonionic agent); a magnetic agent or a paramagnetic agent (e.g., gadolinium, iron-oxide chelate); nanoparticles; an enzyme (horseradish peroxidase, alkaline phosphatase, beta.-galactosidase, or acetylcholinesterase); a prosthetic group (e.g., streptavidin/biotin and avidinfbiotin); a fluorescent material (e.g., umbelliferone, fluorescein, fluorescein isothiocyanate, rhodamine, dichlorotriazinylamine fluorescein, dansyl chloride or phycoerythrin); or a luminescent material (e.g., luminol). A label can also be a bioluminescent material (e.g., luciferase, luciferin, aequorin); or any other imaging agent that can be employed for detection, screening, diagnostic, or imaging (e.g., for CT, fluoroscopy, SPECT imaging, optical imaging, PET, MRI, gamma imaging).

The term "infection" means an initial or primary (acute) or a chronic infection. An infection may be "infectious" in the sense that other sites in the infected host subject, or contagious to other subjects (cross-infection), or may be latent. An initial/primary (acute) infection can cause mild, moderate or severe pathogenesis or symptoms, or be asymptomatic. A primary/initial infection may or may not be self-limiting, and can become progressively worse, or become latent. A "latent" infection in a host subject is a state in which the infection (e.g., virus) evades immune clearance and remains in the host subject, which infection can be chronic, even lifelong. In the latent state illness or symptoms may not be present or may be mild. Reactivation of an infection means activation in the host subject following a period of latency. Reactivation is associated with increased replication and proliferation in a subject. Symptoms and pathologies associated with or caused by reactivation may also increase.

Specific non-limiting examples of infections include chronic, acute or latent bacterial (gram negative and gram positive and non-gram staining) viral, parasite and fungal infections. Infections can be either pathogenic or non-pathogenic infections (e.g., pathogenic or non-pathogenic bacterial, viral, parasite and fungal infections).

Specific non-limiting examples of gram negative bacterial infections include: *Bordetella, Bordetella pertussis; Borrelia, Borrelia burgdorferi; Brucella, Brucella abortus, Brucella canis, Brucella melitensis, Brucella suis, Campylobacter, Campylobacter jejuni; Escherichia, Escherichia coli; Francisella, Francisella tularensis; Haemophilus*, aemophilus influenzae; *Helicobacter, Helicobacter pylori; Legionella, Legionella pneumophila; Leptospira, Leptospira interrogans; Neisseria, Neisseria gonorrhoeae, Neisseria meningitides; Pseudomonas, Pseudomonas aeruginosa; Rickettsia Rickettsia rickettsii, Salmonella, Salmonella typhi, Salmonella typhimurium; Shigella Shigella sonnei; Treponema, Treponema pallidum; Vibrio, Vibrio cholerae; Yersinia, Yersinia pestis.* a mycobacterium (e.g., tuberculosis and atypical *mycobacterium*), *listeria* monocytogenes, *helicobacter, bordetella, streptococcus, salmonella* and *chlamydia.*

Specific non-limiting examples of gram positive bacterial infections include: *Clostridium, Clostridium botulinum, Clostridium difficile, Clostridium perfringens, Clostridium tetani; Corynebacterium, Corynebacterium diphtheriae; Enterococcus, Enterococcus faecalis, Enterococcus faecum; Listeria Listeria*, monocytogenes; *Staphylococcus, Staphylococcus aureus; Staphylococcus epidermidis, Staphylococcus saprophyticus; Streptococcus, Streptococcus agalactiae; Streptococcus pneumoniae; Streptococcus pyogenes.*

Specific non-limiting examples of non-gram staining bacteria include: *Chlamydia, Chlamydia pneumoniae, Chlamydia psittaci, Chlamydia trachomatis; Mycobacterium, Mycobacterium leprae, Mycobacterium tuberculosis; Mycoplasma, Mycoplasma pneumoniae.*

Specific non-limiting examples of viral infections include poxvirus, herpesvirus, hepatitis virus, immunodeficiency virus, flavivirus, papilloma virus (PV), polyoma virus, rhabdovirus, a myxovirus, an arenavirus, a coronavirus, adenovirus, reovirus, picornavirus, togavirus, bunyavirus, parvovirus or retrovirus.

Poxviruses include a vaccinia virus, *Molluscum contagiosum*, variola major smallpox virus, variola minor smallpox virus, cow pox, camel pox, sheep pox, and monkey pox. Herpesviruses include alpha-herpesvirus, beta-herpesvirus, gamma-herpesvirus, Epstein Bar Virus (EBV), Cytomegalovirus (CMV), varicella zoster virus (VZV/HHV-3), and human herpes simplex virus-1 (HSV-1), herpes simplex virus-2 (HSV-2) and varicella zoster virus (VZV/HHV-3). Particular non-limiting examples of beta- and gamma-herpesvirus include cytomegalovirus (CMV), Epstein-Barr virus (EBV), human herpes virus-6, -7 and -8 (HHV-6, HHV-7, or HHV-8/Kaposi's sarcoma herpesvirus/KSHV). Hepatitis viruses include hepatitis A, B, C, D, E and G. Immunodeficiency viruses include human immunodeficiency virus (HIV), such as HIV-1, HIV-2 and HIV-3.

Flaviviruses include Hepatitis C virus, Yellow Fever virus, Dengue virus, and Japanese Encephalitis and West Nile viruses. Papilloma viruses include human papilloma virus (HPV), such as HPV strain 1, 6, 11, 16, 18, 30, 31, 42, 43, 44, 45, 51, 52, and 54. Polyoma viruses include BK virus (BKV) and JC virus (JCV). Rhabdoviruses include rabies virus and vesiculovirus. Myxoviruses include paramyxovirus (e.g., measles, mumps, pneumovirus and respiratory syncytial virus (RSV) and orthomyxovirus (e.g., influenza virus, such as influenza A, influenza B and influenza C). Arenaviruses include lymphocytic choriomeningitis virus (LCMV), Junin virus, Lassa virus, Guanarito virus, Sabia virus and Machupo virus. Coronaviruses include viruses that cause a common cold or severe acute respiratory syndrome (SARS). Adenoviruses include viral infections of the bronchii, lung, stomach, intestine (gastroenteritis), eye (conjunctivitis), bladder (cystitis) and skin. Reoviruses include a rotavirus, cypovirus and orbivirus. Picornaviruses include rhinovirus (e.g., causing a common cold), apthovirus, hepatovirus, enterovirus, coxsackie B virus and cardiovirus. Togaviruses include alphavirus, sindbus virus, and rubellavirus. Bunyaviruses incltide hantavirus, phlebovirus and nairovirus. Retroviruses include alpha, beta, delta, gamma, epsilon, lentivirus, spumavirus and human T-cell leukemia virus, such as human T-cell leukemia virus 1 and 2 (HTLV-1 and HTLV-2). Lentiviruses include immunodeficiency virus, such as bovine, porcine, equine, canine, feline and primate virus.

Specific non-limiting examples of parasites include a protozoa or nematode. Exemplary protozoa include a *Toxoplasma gondii, Leishmania, Plasmodium*, or *Trypanosoma cruzi*. Exemplary nematodes include a *Schistosoma mansoni*, or a *Heligmosomoides polygyrus*. Exemplary fungus includes *Candida albicans*.

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" refers to spread or dissemination of a tumor, cancer or neoplasia to other sites, locations or regions within the subject, in which the sites, locations or regions are distinct from the primary tumor or cancer.

Invention methods include diagnosing, detecting, screening for, or imaging a primary neoplasia, tumor cancer and metastasis thereof. Metastasis include spreading to other sites, or the formation or establishment of neoplasia, tumors or cancers at other sites distal from the primary neoplasia, tumor or cancer. Thus, methods of the invention include, amoung other things, diagnosing, detecting, screening for, or imaging a metastases arising from a primary neoplasia, tumor or cancer to one or more other sites, locations or regions distinct from the primary neoplasia, tumor or cancer, growth or proliferation of a metastasis at one or more other sites, locations or regions distinct from the primary neoplasia, tumor or cancer, and formation or establishment of additional metastasis.

Neoplasias, tumors and cancers that can be diagnosed, detected, screened for, or imaged include sarcoma, carcinoma, adenocarcinoma, melanoma, myeloma, blastoma, glioma, lymphoma or leukemia. Exemplary cancers include, for example, carcinoma, sarcoma, adenocarcinoma, melanoma, neural (blastoma, glioma), mesothelioma and reticuloendothelial, lymphatic or haematopoietic neoplastic disorders (e.g., myeloma, lymphoma or leukemia).

Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission.

A "solid neoplasia, tumor or cancer" refers to neoplasia, tumor or cancer (e.g., metastasis) that typically aggregates together and forms a mass. Specific examples include visceral tumors such as melanomas, breast, pancreatic, uterine and ovarian cancers, testicular cancer, including seminomas, gastric or colon cancer, hepatomas, adrenal, renal and bladder carcinomas, lung, head and neck cancers and brain tumors/cancers.

Carcinomas refer to malignancies of epithelial or endocrine tissue, and include respiratory system carcinomas (lung, small cell lung), gastrointestinal system carcinomas, genitourinary system carcinomas, testicular carcinomas, breast carcinomas, prostatic carcinomas, endocrine system carcinomas, and melanomas. The term also includes carcinosarcomas, e.g., which include malignant tumors composed of carcinomatous and sarcomatous tissues. Adenocarcinoma includes a carcinoma of a glandular tissue, or in which the tumor forms a gland like structure. Melanoma refers to malignant tumors of melanocytes and other cells derived from pigment cell origin that may arise in the skin, dermis, eye (including retina), or other regions of the body. Additional carcinomas can form from the uterine/cervix, endometrium, lung, head/neck, colon, pancreas, testes, adrenal gland, kidney, esophagus, stomach, liver and ovary.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma, oligodendrocytoma Specific non-limiting examples of neoplasias, tumors and cancers include malignant and non-malignant neoplasias, tumors and cancers, and metastasis. In particular, a neoplasia, tumor, cancer or metastasis of any stage (e.g., stages IA, IB, IIA, IIB, IIIA, IIIB or IV) or grade (e.g., grades G1, G2 or G3).

A "liquid neoplasia, tumor or cancer" refers to a neoplasia, tumor or cancer of the reticuloendothelial or hematopoetic system, such as a lymphoma, myeloma, or leukemia, or a neoplasia that is diffuse in nature. Particular examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML); lymphoid malignancies include, but are not limited to, acute lymphoblastic leukemia (ALL), which includes B-lineage ALL and T-Iineage ALL, chronic lymphocytic leukemia (CLL), prolymphocytic leukemia (PLL), hairy cell leukemia (HLL) and Waldenstrom's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

An infection, tumor, cancer or neoplasia, or a metastasis thereof may arise from any cause or may affect any part of the body of a subject. Exemplary parts (e.g., organ, tissue) affected include skin, dermis, breast, lung, nasopharynx, nose or sinuses, thyroid, head, neck, brain, spine, adrenal gland, thyroid, lymph, blood, gastrointestinal (mouth, esophagug, stomach, duodenum, ileum, jejunum (small intestine), colon, rectum), genito-urinary tract (uterus, ovary, endometrium, cervix, bladder, testicle, penis, urinary tract, prostate), kidney, pancreas, adrenal gland, liver, bone, bone marrow, heart, muscle, and the hematopoetic system. Thus, a method of the invention may be performed to diagnose, detect, screen, or image an infection, a tumor, cancer or neoplasia, or a metastasis thereof in the whole body of a subject, a particular region or general area, a specific organ or tissue, or a local portion of a region, organ or tissue.

Methods of the invention include detecting the type, kind, presence or absence, location or extent of an infection, tumor, cancer or neoplasia, or a metastasis thereof. Such methods can be used to alternatively or additionally provide information on severity or progression of infection, tumor, cancer or neoplasia, or a metastasis thereof; prognosis of infection, tumor, cancer or neoplasia, or a metastasis thereof; and/or therapy or treatment of infection, tumor, cancer or neoplasia, or a metastasis thereof based upon detecting, diagnosing, screening or imaging.

As used herein, a "sufficient amount" or "effective amount" or an "amount sufficient" or an "amount effective" refers to an amount that is sufficient to detect an infection, tumor, cancer or neoplasia, or a metastasis thereof. Typically, the amount is less than an amount that leads to substantial lysis or killing of the target infection, tumor, cancer or neoplasia, or a metastasis thereof. Thus, an amount sufficient or effective is that amount to allow detection, diagnosis, screening or imaging, without substantial cell or infection killing such that an infection; tumor, cancer or neoplasia, or a metastasis thereof is no longer detected, diagnosed, or imaged. Further, the amount of labeled CSA may vary with the particular label used and the method of detection in order to achieve a desired image.

Methods of detection, diagnostics or screening, such as in vitro, ex vivo, and vivo imaging methods, permit the detection of a labeled CSA. Such methods of CSA detection include magnetic resonance spectroscopy (MRS), magnetic resonance imaging (MRI), positron-emission tomography (PET), gamma-scintigraphy, computed tomography (CT), Computed Axial Tomography (CAT), or single photon emission tomography (SPECT).

Methods also include detecting an infection, or diagnosing a subject having or at risk of having an infection, a tumor, cancer or neoplasia, (in vivo, ex vivo or in vitro). Such methods include contacting a detectably labeled CSA to a biological sample from a subject under conditions whereby the labeled CSA can bind to an infection in the sample, and detecting the labeled CSA in the sample to ascertain the presence or absence of an infection, a tumor, cancer or neoplasia, in the sample, thereby of detecting an infection, a tumor, cancer or neoplasia, or diagnosing the subject as having or not having an infection, a tumor, cancer or neoplasia.

Biological samples include any sample capable of having a biological material. Specific non-limiting examples include mucus, saliva, feces, blood, serum, plasma, cerebrospinal fluid, urine, or placenta. Biological samples also include biopsies, for example, of skin, dermis, breast, lung, nasopharynx, nose or sinuses, thyroid, head, neck, adrenal gland, thyroid, lymph, gastrointestinal tract, genito-urinary tract, kidney, pancreas, adrenal gland, liver, bone, bone marrow, heart, muscle, or a sample of the hematopoetic system.

For in vitro, ex vivo, and in vivo diagnosing, detecting, screening or imaging, the type of detection instrument available can depend upon a given label or conjugate. As an example, a radioisotope or paramagnetic isotope is suitable for in vivo detection, diagnosis, screening or imaging. The type of lable, such as a radionuclide or metal, will guide the selection of the instrument used. For instance, decay parameters of a chosen alpha, beta, or gamma radionuclide chosen can be detectable or measured by the selected instrument.

In various embodiments a label or conjugate, such as a radionuclide or metal or metal oxide can be bound to a CSA, either directly or indirectly, using an intermediary functional group. Intermediary functional groups which are often used to bind radioisotopes which exist as, for example, metallic ions (e.g, cations) that bind to groups on the CSAs. Examples include agents that react with free or semi-free amines, oxygen, sulfur, hydroxy or carboxy groups. Such functional groups therefore include mono and bifunctional crosslinkers, such as DSS, BS3 (Sulfo-DSS), DSG. Non-limiting examples include diethylenetriaminepentaacetic acid (DTPA) and ethylene diaminetetracetic acid (EDTA). Additional functional groups include carbon esideus, or one or more of a succinly groups, such as disulfosuccinimidyl tartarate, disuccinimidyl glutarate and disuccinimidyl suberate.

A "subject" refers to an animal, typically mammalian animals, such as but not limited to non-human primates (apes, gibbons, gorillas, chimpanzees, orangutans, macaques), domestic animals (dogs and cats), a farm animals (chickens, ducks, horses, cows, goats, sheep, pigs), experimental animal (mouse, rat, rabbit, guinea pig) and humans. Subjects include animal models, for example, a mouse model of an infection, tumor, cancer or neoplasia, or a metastasis thereof. Subjects include naturally occurring or non-naturally occurring mutated or non-human genetically engineered (e.g., transgenic or knockout) animals. Subjects further include animals having or at risk of having an infection, tumor, cancer or neoplasia, or a metastasis thereof. Subjects can be any age. For example, a subject (e.g., human) can be a newborn, infant, toddler, child, teenager, or adult, e.g., 50 years or older.

Subjects include those in need of a method of the invention, e.g., in need of diagnosis, detection, screening or imaging. A subject is considered to be in need of a method of the invention where a method is likely to provide information concerning the presence or absence of, the extent or severity of, the status or prognosis of, or possible treatment or therapy of, an infection, tumor, cancer or neoplasia, or a metastasis thereof.

Subjects appropriate for treatment therefore include those having or at risk of having an infection, tumor, cancer or neoplasia, or a metastasis thereof. At risk subjects include subjects that have been exposed to an infection or infectious agent, or are at risk of developing a tumor, cancer or neoplasia, or a metastasis thereof, due to a genetic predispositon or family history, or environmental risk due to smoking, exposure to smoke or carcinogens, chemicals, sun exposure, etc. A subject may therefore be symptomatic or asymptomatic for an infection, tumor, cancer or neoplasia, or a metastasis thereof. Candidate subjects therefore include subjects that have been exposed to or contacted with an infection, or that are at risk of exposure to or contact with an infection, regardless of the type, timing or extent of exposure or contact. The invention methods are therefore applicable to a subject who is at risk of an infection, tumor, cancer or neoplasia, or a metastasis thereof, but has not yet been diagnosed for an an infection, tumor, cancer or neoplasia, or a metastasis thereof. Prophylactic methods are therefore included.

Compounds of the invention, including CSAs, can be incorporated into pharmaceutical compositions or formulations. Such pharmaceutical compositions/formulations are useful for administration to a subject, in vivo or ex vivo.

Pharmaceutical compositions and formulations include carriers or excipients for administration to a subject. As used herein the terms "pharmaceutically acceptable" and "physiologically acceptable" mean a biologically compatible formulation, gaseous, liquid or solid, or mixture thereof, which is suitable for one or more routes of administration, in vivo delivery or contact. A formulation is compatible in that it does not destroy activity of an active ingredient therein (e.g., a CSA), or induce adverse side effects that far outweigh any prophylactic or therapeutic effect or benefit.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

The formulations may, for convenience, be prepared or provided as a unit dosage form. Preparation techniques include bringing into association the active ingredient (e.g., CSA) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA) moistened with an inert liquid diluent. The tablets may optionally be coated or scored and may be formulated so as to provide a slow or controlled release of the active ingredient therein.

Pharmaceutical compositions can optionally be formulated to be compatible with a particular route of administration. Exemplary routes of administration include administration to a biological fluid or tissue, mucosal cell or tissue (e.g., mouth, buccal cavity, labia, nasopharynx, esophagus, trachea, lung, stomach, small intestine, vagina, rectum, or colon), neural cell or tissue (e.g., ganglia, motor or sensory neurons) or epithelial cell or tissue (e.g., nose, fingers, ears, cornea, conjunctiva, skin or dermis). Thus, pharmaceutical compositions include carriers (excipients, diluents, vehicles or filling agents) suitable for administration to any cell, tissue or organ, in vivo, ex vivo (e.g., tissue or organ transplant) or in vitro, by various routes and delivery, locally, regionally or systemically.

Exemplary routes of administration for contact or in vivo delivery which a compound of the invention (e.g., CSA) can optionally be formulated include inhalation, respiration, intubation, intrapulmonary instillation, oral (buccal, sublingual, mucosal), intrapulmonary, rectal, vaginal, intrauterine, intradermal, topical, dermal, parenteral (e.g., subcutaneous, intramuscular, intravenous, intradermal, intraocular, intratracheal and epidural), intranasal, intrathecal, intraarticular, intracavity, transdermal, iontophoretic, ophthalmic, optical (e.g., corneal), intraglandular, intraorgan, intralymphatic.

Formulations suitable for parenteral administration include aqueous and non-aqueous solutions, suspensions or emulsions of the compound, which may include suspending agents and thickening agents, which preparations are typically sterile and can be isotonic with the blood of the intended recipient. Non-limiting illustrative examples of aqueous carriers include water, saline (sodium chloride solution), dextrose (e.g., Ringer's dextrose), lactated Ringer's, fructose, ethanol, animal, vegetable or synthetic oils. Examples of non-aqueous solvents are propylene glycol, polyethylene glycol, vegetable oils such as olive oil, and injectable organic esters such as ethyl oleate. Intravenous vehicles include fluid and nutrient replenishers, electrolyte replenishers (such as those based on Ringer's dextrose). The formulations may be presented in unit-dose or multi-dose kits, for example, ampules and vials, and may be stored in a freeze-dried (lyophilized) condition requiring addition of a sterile liquid carrier, for example, water for injections, prior to use.

For transmucosal or transdermal administration (e.g., topical contact), penetrants can be included in the pharmaceutical composition. Penetrants are known in the art, and include, for example, for transmucosal administration, detergents, bile salts, and fusidic acid derivatives. For transdermal administration, the active ingredient can be formulated into aerosols, sprays, ointments, salves, gels, pastes, lotions, oils or creams as generally known in the art.

For topical administration, for example, to skin, pharmaceutical compositions typically include ointments, creams, lotions, pastes, gels, sprays, aerosols or oils. Carriers which may be used include Vaseline, lanolin, polyethylene glycols, alcohols, transdermal enhancers, and combinations thereof.

For oral administration, aceutical compositions include capsules, cachets, lozenges, tablets or troches, as powder or granules. Oral administration formulations also include a solution or a suspension (e.g., aqueous liquid or a non-aqueous liquid; or as an oil-in-water liquid emulsion or a water-in-oil emulsion).

For airway or nasal administration, pharmaceutical compositions can be formulated in a dry powder for delivery, such as a fine or a coarse powder having a particle size, for example, in the range of 20 to 500 microns which is administered in the manner by inhalation through the airways or nasal passage. Depending on delivery device efficiency, effective dry powder dosage levels typically fall in the range of about 10 to about 100 mg. Appropriate formulations, wherein the carrier is a liquid, for administration, as for example, a nasal spray or as nasal drops, include aqueous or oily solutions of the active ingredient. Dry-powder inhalers (DPI) can be used to deliver the compounds (CSAs), either alone or in combination with a pharmaceutically acceptable carrier.

For airway or nasal administration, aerosol and spray delivery systems and devices, also referred to as "aerosol generators" and "spray generators," such as metered dose inhalers (MDI), nebulizers (ultrasonic, electronic and other nebulizers), nasal sprayers and dry powder inhalers can be used. MDIs typically include an actuator, a metering valve, and a container that holds a suspension or solution, propellant, and surfactant (e.g., oleic acid, sorbitan trioleate, lecithin). Activation of the actuator causes a predetermined amount to be dispensed from the container in the form of an aerosol, which is inhaled by the subject.

For rectal administration, pharmaceutical compositions can be included as a suppository with a suitable base comprising, for example, cocoa butter or a salicylate. For vaginal administration, pharmaceutical compositions can be included as pessaries, tampons, creams, gels, pastes, foams or spray formulations containing in addition to the active ingredient (e.g., CSA) a carrier, examples of appropriate carriers which are known in the art.

Pharmaceutical formulations and delivery systems appropriate for the compositions and methods of the invention are known in the art (see, e.g., *Remington: The Science and Practice of Pharmacy* (2003) $20^{th}$ ed., Mack Publishing Co., Easton, Pa.; *Remington's Pharmaceutical Sciences* (1990) $18^{th}$ ed., Mack Publishing Co., Easton, Pa.; *The Merck Index* (1996) $12^{th}$ ed., Merck Publishing Group, Whitehouse, N.J.; *Pharmaceutical Principles of Solid Dosage Forms* (1993), Technonic Publishing Co., Inc., Lancaster, Pa.; Ansel and Stoklosa, *Pharmaceutical Calculations* (2001) $11^{th}$ ed., Lippincott Williams & Wilkins, Baltimore, Md.; and Poznansky et al., *Drug Delivery Systems* (1980), R. L. Juliano, ed., Oxford, N.Y., pp. 253-315).

Compounds of the invention (e.g., CSAs), including pharmaceutical formulations can be packaged in unit dosage forms for ease of administration and uniformity of dosage. A "unit dosage form" as used herein refers to a physically discrete unit suited as unitary dosages for the subject to be administered or contacted; each unit containing a predetermined quantity of compound optionally in association with a pharmaceutical carrier (excipient, diluent, vehicle or filling agent). Unit dosage forms can contain a daily dose or unit, daily sub-dose, or an appropriate fraction thereof, of an administered compound (e.g., CSA). Unit dosage forms also include, for example, capsules, troches, cachets, lozenges, tablets, ampules and vials, which may include a composition in a freeze-dried or lyophilized state; a sterile liquid carrier, for example, can be added prior to administration, contact, or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds of the invention (e.g., CSAs) can be administered at any duration or frequency. Typically, a labeled CSA is administered as a bolus or is administered in multiple dose to provide detection, diagnosis, screening or imaging.

Exemplary non-limiting doses include, for example, those based on the mass of a subject. Doses can generally be in a range from about 0.1-1 ug/kg, 1-10 ug/kg, 10-25 ug/kg, 25-50 ug/kg, 50-100 ug/kg, 100-500 ug/kg, 500-1,000 ug/kg, 1-4 mg/kg, 4-10 mg/kg, 10-20 mg/kg, 20-50 mg/kg, 50-100 mg/kg, 100-250 mg/kg, 250-500 mg/kg, or more, of subject body weight, two, three, four, or more times per hour, day, week, month or annually. Of course, doses can be more or less, as appropriate, for example, 0.00001 mg/kg of subject body weight to about 10,000.0 mg/kg of subject body weight, about 0.001 mg/kg, to about 100 mg/kg, about 0.01 mg/kg, to about 10 mg/kg, or about 0.1 mg/kg, to about 1 mg/kg of subject body weight over a given time period, e.g., 1, 2, 3, 4, 5 or more hours, days, weeks, months, years.

A subject may be administered single bolus or in divided/metered doses, which can be adjusted to be more or less according to the various consideration set forth herein and known in the art. Dosage levels of labeled CSA also can take, into consideration the particular detectable label and detection system in order to achieve a desired image.

The invention provides kits including compounds of the invention (e.g., CSA), combination compositions and pharmaceutical compositions/formulations thereof, packaged into a suitable packaging material. In one embodiment, a kit includes packaging material, a cationic steroid antimicrobial (CSA) and instructions. In various aspects, the instructions are for administering the CSA to diagnose, detect, screen or image an infection, tumor, cancer or neoplasia, or a metastasis thereof.

The term "packaging material" refers to a physical structure housing one or more components of the kit. The packaging material can maintain the components sterilely, and can be made of material commonly used for such purposes (e.g., paper, corrugated fiber, glass, plastic, foil, ampules, vials, tubes, etc.). A kit can contain a plurality of components, e.g., two or more CSAs of the invention alone or in combination.

A kit optionally includes a label or insert including a description of the components (type, amounts, doses, etc.), instructions for use in vitro, in vivo, or ex vivo, and any other components therein. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacturer location and date, expiration dates.

Labels or inserts can include information on a infection, disorder or disease (e.g., bacterial, virus infection, tumor, neoplasia or cancer) for which a kit component may be used. Labels or inserts can include instructions for a clinician or subject for using one or more of the kit components in a method, treatment protocol or therapeutic/prophylactic regimen, including the methods of the invention. Instructions can include amounts of compound, frequency or duration of administration, and instructions for practicing any of the methods, treatment protocols or prophylactic or therapeutic regimes described herein. Kits therefore can additionally include labels or instructions for practicing any of the methods of the invention described herein including detection, diagnosis, screening or other methods.

Invention kits can additionally include a buffering agent, or a preservative or a stabilizing agent in a pharmaceutical formulation containing a compound of the invention. Each component of the kit can be enclosed within an individual container and all of the various containers can be within a single package. Invention kits can be designed for cold storage.

Compounds useful in accordance with the invention, are described herein, both generically and with particularity, and in U.S. Pat. Nos. 6,350,738; 6,486,148; and 6,767,904, which are incorporated herein by reference in their entirety. Compounds include steroid derivatives, such as cationic steroid antimicrobials (CSA). The skilled artisan will recognize the compounds within the generic formula set forth herein. Particular CSAs are described herein and can be characterized using the assays set forth herein and in the art.

Compounds of formula I, also referred to as cationic steroid antibmicrobials (CSA), comprise:

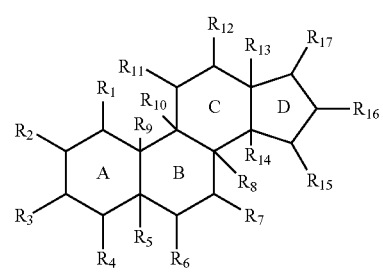

I wherein:
fused rings A, B, C, and D are independently saturated or fully or partially unsaturated; and
each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted (C1-C10) alkyl, (C1-C10) hydroxyalkyl, (C1-C10) alkyloxy-(C1-C10) alkyl, (C1-C10) alkylcarboxy-(C1-C10) alkyl, (C1-C10) alkylamino-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkyl, a substituted or unsubstituted aryl, a substituted or unsubstituted arylamino-(C1-C10) alkyl, (C1-C10) haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkyloxy-(C1-C10) alkyl, a substituted or unsubstituted (C1-C10) aminoalkylcarboxy, a substituted or unsubstituted (C1-C10) aminoalkylaminocarbonyl, a substituted or unsubstituted (C1-C10) aminoalkylcarboxamido, $H_2N$—HC(Q5)-C(O)—O—, $H2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyl oxy, (C1-C10) quaternaryammoniumalkylcarboxy, and (C1-C10) guanidinoalkyl carboxy, where Q5 is a side chain of any amino acid (including the side chain of glycine, i.e., H), P.G. is an amino protecting group, and
$R_5$, $R_8$, $R_9$, $R_{10}$, $R_{13}$, and $R_{14}$ is each independently: deleted when one of fused rings A, B, C, or D is unsaturated so as to complete the valency of the carbon atom at that site, or selected from the group consisting of hydrogen, hydroxyl, a substituted or unsubstituted (C1-C10) alkyl, (C1-C10) hydroxyalkyl, (C1-C10) alkyloxy-(C1-C10) alkyl, a substituted or unsubstituted (C1-C10) aminoalkyl, a substituted or unsubstituted aryl, C1-C10 haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkylcarboxy, a substituted or unsubstituted (C1-C10) aminoalkylaminocarbonyl, $H2N$—HC(Q5)-C(O)—O—, $H2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy, where Q5 is a side chain of any amino acid, P.G. is an amino protecting group, and provided that at least two of $R_1$ through $R_{14}$ are independently selected from the group consisting of a substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkylcarboxy, a substituted or unsubstituted arylamino-(C1-C10) alkyl, a substituted or unsubstituted (C1-C10) aminoalkyloxy-(C1-C10) alkyl, a substituted or unsubstituted (C1-C10) aminoalkylaminocarbonyl, (C1-C10) quaternaryammonium alkylcarboxy, H2N—HC(Q5)-C(O)—O—, H2N—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy; or a pharmaceutically acceptable salt thereof.

A "ring" as used herein can be heterocyclic or carbocyclic. The term "saturated" used herein refers to the fused ring of formula I having each atom in the fused ring either hydrogenated or substituted such that the valency of each atom is filled. The term "unsaturated" used herein refers to the fused ring of formula I where the valency of each atom of the fused ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond; such as $R_5$ and $R_9$; $R_8$ and $R_{10}$; and $R_{13}$ and $R_{14}$.

The term "unsubstituted" used herein refers to a moiety having each atom hydrogenated such that the valency of each atom is filled.

The term "halo" used herein refers to a halogen atom such as fluorine, chlorine, bromine, or iodine.

Examples of amino acid side chains include but are not limited to H (glycine), methyl (alanine), —$CH_2$—(C=O)—$NH_2$ (asparagine), —$CH_2$—SH (cysteine), and —CH(OH)$CH_3$ (threonine).

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. Substituted alkyl groups may have one, two, three or more substituents, which may be the same or different, each replacing a hydrogen atom. Substituents are halogen (e.g., F, Cl, Br, and I), hydroxyl, protected hydroxyl, amino, protected amino, carboxy, protected carboxy, cyano, methylsulfonylamino, alkoxy, acyloxy, nitro, and lower haloalkyl.

The term "substituted" used herein refers to moieties having one, two, three or more substituents, which may be the same or different, each replacing a hydrogen atom. Examples of substituents include but are not limited to halogen (e.g., F, Cl, Br, and I), hydroxyl, protected hydroxyl, amino, protected amino, carboxy, protected carboxy, cyano, methylsulfonylamino, alkoxy, alkyl, aryl, aralkyl, acyloxy, nitro, and lower haloalkyl.

An aryl group is a C6-20 aromatic ring, wherein the ring is made of carbon atoms (e.g., C6-C14, C6-10 aryl groups). Examples of haloalkyl include fluoromethyl, dichloromethyl, trifluoromethyl, 1,1-difluoroethyl, and 2,2-dibromoethyl.

An aralkyl group is a group containing 6-20 carbon atoms that has at least one aryl ring and at least one alkyl or alkylene chain connected to that ring. An example of an aralkyl group is a benzyl group.

A linking group is any divalent moiety used to link a compound of formula to another steroid, e.g., a second compound of formula I. An example of a linking group is (C1-C10) alkyloxy-(C1-C10) alkyl.

Amino-protecting groups are known to those skilled in the art. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in T. W. Greene, Protective Groups in Organic Chemistry, (1st ed., 1981, 2nd ed., 1991).

The invention compounds also include a ring system of at least 4 fused rings, where each of the rings has from 5-7 atoms. The ring system has two faces, and contains 3 chains attached to the same face. Each of the chains contains a nitrogen-containing group that is separated from the ring system by at least one atom; the nitrogen-containing group is an amino group, e.g., a primary amino group, or a guanidino group. The compound can also contain a hydrophobic group, such as a substituted (C3-10) aminoalkyl group, a (C1-10) alkyloxy (C3-10) alkyl group, or a (C1-10) alkylamino (C3-10)alkyl group, attached to the steroid backbone. For example, the compound may have the formula V, where each of the three chains containing nitrogen-containing groups is independently selected from $R_1$ through $R_4$, $R_6$, $R_7$, $R_{11}$, $R_{12}$, $R_{15}$, $R_{16}$, $R_{17}$, and $R_{18}$, defined below.

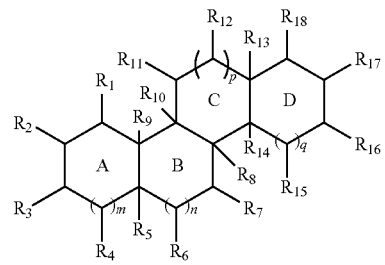

V where:
each of fused rings A, B, C, and D is independently saturated, or is fully or partially unsaturated, provided that at least two of A, B, C, and D are saturated, wherein rings A, B, C, and D form a ring system;
each of m, n, p, and q is independently 0 or 1;
each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, a substituted or unsubstituted (C1-C10) alkyl, (C1-C10) hydroxyalkyl, (C1-C10) alkyloxy-(C1-C10) alkyl, (C1-C10)alkylcarboxy-(C1-C10 alkyl, (C1-C10) alkylamino-(C1-C10) alkyl, (C1-C10) alkylamino-(C1-C10) alkylamino, (C1-C10 alkylamino-(C1-C10) alkylamino-(C1-C10) alkylamino, a substituted or unsubstituted (C1-C10) aminoalkyl, a substituted or unsubstituted aryl, a substituted or unsubstituted arylamino-(C1-C10) alkyl, (C1-C10) haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkyloxy-(C1-C10) alkyl, a substituted or unsubstituted (C1-C10) aminoalkylcarboxy, a substituted or unsubstituted (C1-C10) aminoalkylaminocarbonyl, a substituted or unsubstituted (C1-C10) aminoalkylcarboxamido, $H_2N$—HC(Q5)-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyl oxy, (C1-C10) quaternaryammoniumalkylcarboxy, and (C1-C10) guanidinoalkyl carboxy, where Q5 is a side chain of any amino acid (including a side chain of glycine, i.e., H). P.G. is an amino protecting group; and each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, a substituted or unsubstituted (C1-C10) alkyl, (C1-C10) hydroxyalkyl, (C1-C10) alkyloxy-(C1-C10) alkyl, a substituted or unsubstituted (C1-C10) aminoalkyl, a substituted or unsubstituted aryl, C1-C10 haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkylcarboxy, a substituted or unsubstituted (C1-C10) aminoalkylaminocarbonyl, $H2N$—HC(Q5)-C(O)—O—, HN—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy, where Q5 is a side chain of any amino acid, P.G. is an amino protecting group, provided that at least three of $R_1$ through $R_4$, $R_6$, $R_7$, $R_{11}$, $R_{12}$, $R_{15}$, $R_{16}$, $R_{17}$, and $R_{18}$ are disposed on the same face of the ring system and are independently selected from the group consisting of a substituted or unsubstituted (C1-C10) aminoalkyl, a substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkylcarboxy, a substituted or unsubstituted arylamino-(C1-C10) alkyl, a substituted or unsubstituted (C1-C10) aminoalkyloxy-(C1-C10) aminoalkylaminocarbonyl, a substituted or unsubstituted (C1-C10) aminoalkylaminocarbonyl, a substituted or unsubstituted (C1-C5) aminoalkylcarboxamido, a (C1-C10) quaternaryammoniumalkylcarboxy, $H_2N$—HC(Q5)-C(O)—O—, $H_2N$—HC(Q5)-C(O)—N(H)—, (C1-C10) azidoalkyloxy, (C1-C10) cyanoalkylox, P.G.—HN—HC(Q5)-C(O)—O—, (C1-C10) guanidinoalkyloxy, and a (C1-C10) guanidinoalkylcarboxy; or a pharmaceutically acceptable salt thereof. In various aspects, at least two, or at least, three, of m, n, p, and q are 1.

Compounds set forth herein preserve certain stereochemical and electronic characteristics found in steroids. The term "same configuration" as used herein refers to substituents on the fused steroid having the same stereochemical orientation. For example substituents $R_3$, $R_7$ and $R_{12}$ are all β-substituted or α-substituted.

Compounds include but are not limited to compounds having amine or guanidine groups covalently attached to a steroid backbone or scaffold at any carbon position, e.g., cholic acid. In various embodiments, a group is covalently attached at any one, or more, of positions C3, C7 and C12 of the steroid backbone or scaffold. In additional embodiments, a group is absent from any one, or more, of positions C3, C7 and C12 of the steroid backbone or scaffold.

Compounds that include such groups can include a tether, the tether having variable chain length or size. As used herein, the terms "tether" or "tethered," when used in reference to a compound of the invention, refers to the chain of atoms between the steroid backbone or scaffold and a terminal amino or guanidine group. In various embodiments, a tether is covalently attached at any one, or more, of positions C3, C7 and C12. In additional embodiments, a tether is lacking at any one, or more, of positions C3, C7 and C12. A tether length may include the heteroatom (O or N) covalently attached to the steroid backbone.

Other ring systems can also be used, e.g., 5-member fused rings. Compounds with backbones having a combination of 5- and 6-membered rings are also included in the invention. Amine or guanidine groups can be separated from the backbone by at least one, two, three, four or more atoms. The backbone can be used to orient the amine or guanidine groups on one face, or plane, of the steroid. For example, a scheme showing a compound having primary amino groups on one face, or plane, of a backbone is shown below:

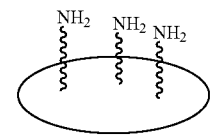

Methods of synthesizing compounds of formula I are provided, wherein for example, at least two of $R_1$ through $R_{14}$ are independently selected from the group consisting of a substituted or unsubstituted (C1-C10) aminoalkyloxy. In one embodiment, a method includes the step of contacting a compound of formula IV,

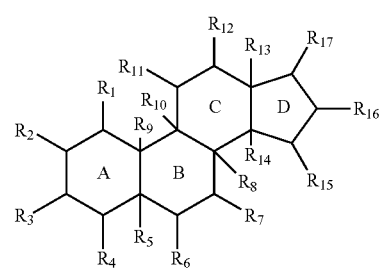

IV where at least two of $R_1$ through $R_{14}$ are hydroxyl, and the remaining moieties on the fused rings A, B, C, and D are defined for formula I, with an electrophile to produce an alkyl ether compound of formula IV, wherein at least two of $R_1$ through $R_{14}$ are (C1-C10)alkyloxy. The alkyl ether compounds are converted into an amino precursor compound wherein at least two of $R_1$ through $R_{14}$ are independently selected from the group consisting of (C1-C10) azidoalkyloxy and (C1-C10) cyanoalkyloxy and the amino precursor compound is reduced to form a compound of formula I.

Electrophiles include but are not limited to 2-(2-bromoethyl)-1,3-dioxolane, 2-iodoacetamide, 2-chloroacetamide, N-(2-bromoethyl)phthalimide, N-(3-bromopropyl)phthalimide, and allybromide. An exemplary electrophile is allylbromide.

Compounds of formula I include at least two of $R_1$ through $R_{14}$ are (C1-C10) guanidoalkyloxy. In one embodiment, a method includes contacting a compound of formula IV, where at least two of $R_1$ through $R_{14}$ are hydroxyl, with an electrophile to produce an alkyl ether compound of formula IV, where at least two of $R_1$ through $R_{14}$ are (C1-C10)alkyloxy. The allyl ether compound is converted into an amino precursor compound where at least two of $R_1$ through $R_{14}$ are independently selected from the group consisting of (C1-C10) azidoalkyloxy and (C1-C10) cyanoalkyloxy. The amino precursor compound is reduced to produce an aminoalkyl ether compound wherein at least two of $R_1$ through $R_{14}$ are (C1-C10) aminoalkyloxy. The aminoalkyl ether compound is contacted with a guanidino producing electrophile to form a compound of formula I.

The term "guanidino producing electrophile" used herein refers to an electrophile used to produce a guanidino compound of formula I. An example of an guanidino producing electrophile is $HSO_3$—$C(NH)$—$NH_2$.

Compounds of formula I also include at least two of $R_1$ through $R_{14}$ are H2N—HC(Q5)-C(O)—O— and Q5 is the side chain of any amino acid. In one embodiment, a method includes the step of contacting a compound of formula IV, where at least two of $R_1$ through $R_{14}$ are hydroxyl, with a protected amino acid to produce a protected amino acid compound of formula IV where at least two of at least two of $R_1$ through $R_{14}$ are P.G.—HN—HC(Q5)-C(O)—O— and Q5 is the side chain of any amino acid and P.G. is an amino protecting group. The protecting group of the protected amino acid compound is removed to form a compound of formula I.

Exemplary non-limiting synthesis schemes for preparing compounds of the invention include the following:

Scheme 1 Illustrates Preparation of Compounds 1, 2, 4 and 5

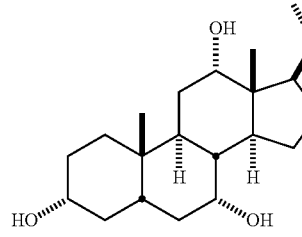

methyl cholate

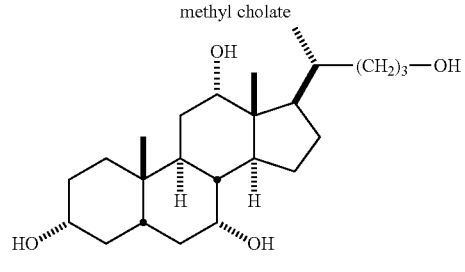

13

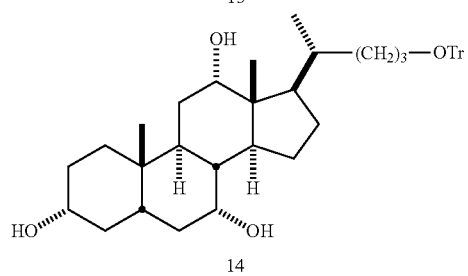

14

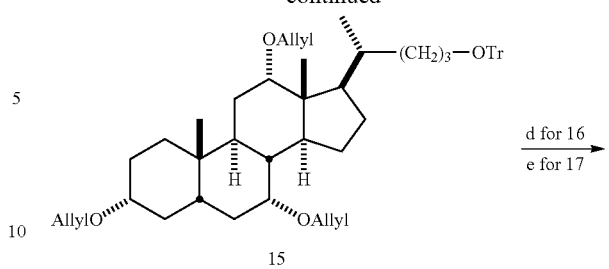

15

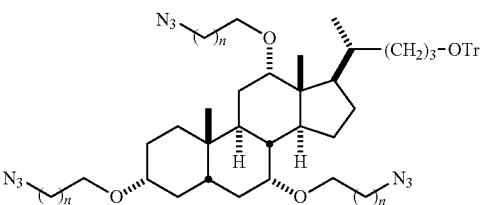

16 n = 1
17 n = 2

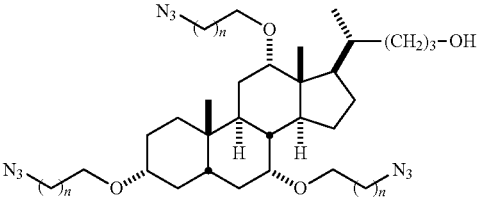

18 n = 1
19 n = 2

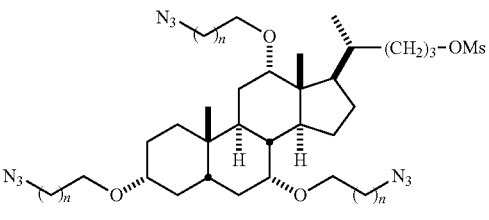

20 n = 1
21 n = 2

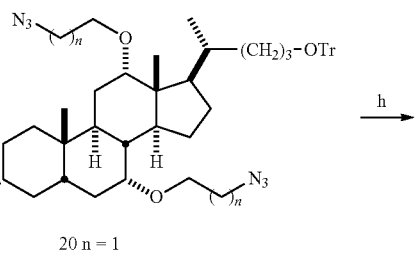

22 n = 1
23 n = 2

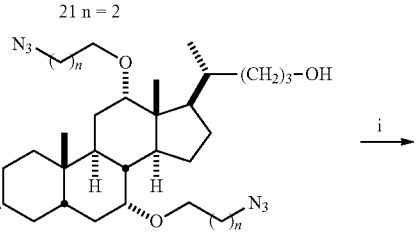

24 n = 1
25 n = 2

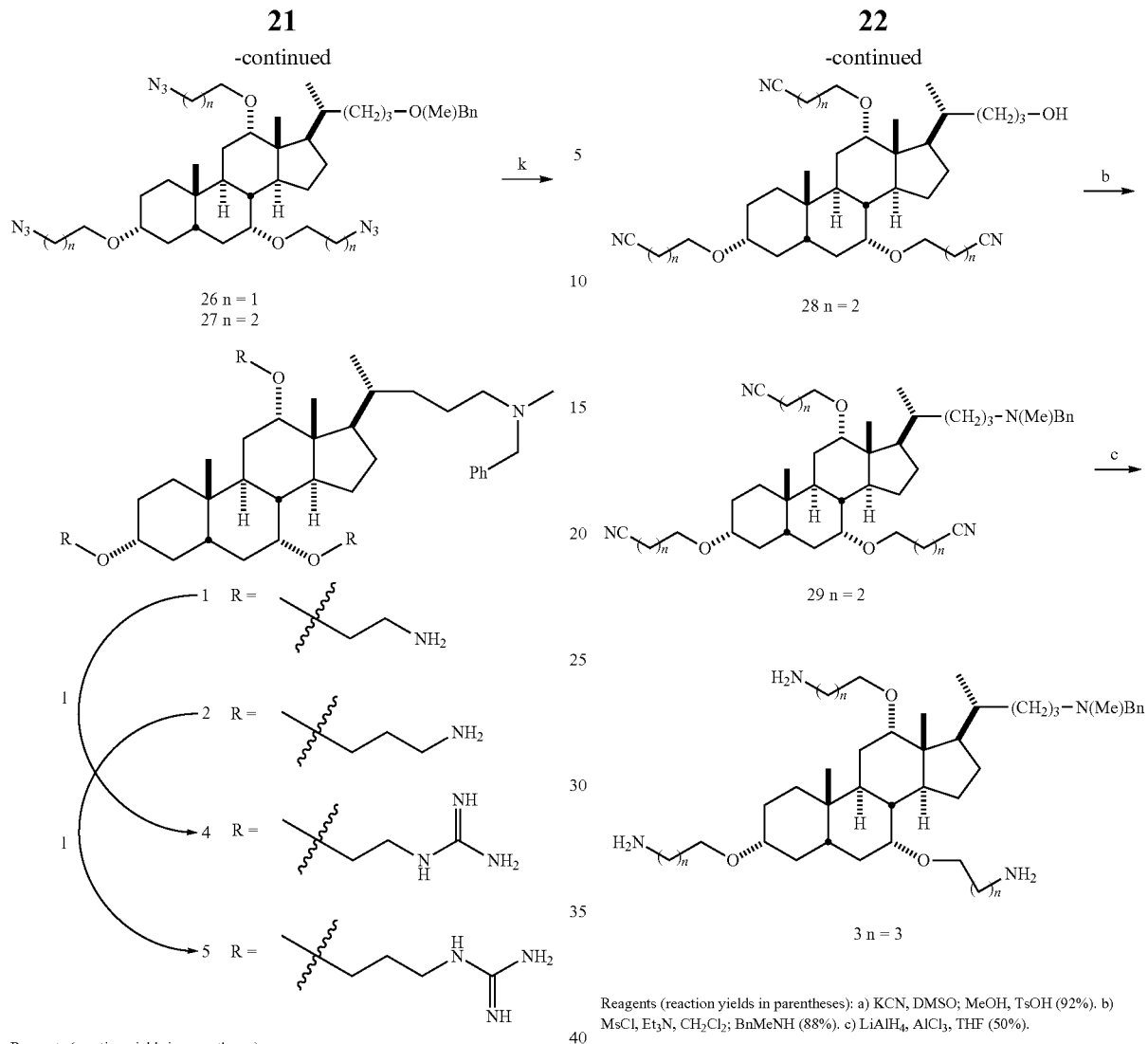

Reagents (reaction yields in parentheses):
a) LiAlH$_4$, THF (98%).
b) triylchloride, Et$_3$N, DMF (70%).
c) allylbromide, NaH, THF (96%).
d) O$_3$, CH$_2$Cl$_2$, MeOH; Me$_2$S; NaBH$_4$ (95%).
e) 9-BBN, THF; H$_2$O$_2$, NaOH (80%).
F) MsCl, CH$_2$Cl$_2$, Et$_3$N (78%, 82%).
g) NaN$_3$, DMSO (66% for 20, 19 carried directly on to 23).
h) TsOH, MeOH (94%, 94% overall from 19).
i) MsCl, CH$_2$Cl$_2$, Et$_3$N (99%, 97%).
j) N-benzylmethylamine (95%, 96%).
k) LiAlH$_4$, THF (95%, 99%).
l) NH$_2$C(NH)SO$_3$H, MeOH (91%, 89%).

Reagents (reaction yields in parentheses): a) KCN, DMSO; MeOH, TsOH (92%). b) MsCl, Et$_3$N, CH$_2$Cl$_2$; BnMeNH (88%). c) LiAlH$_4$, AlCl$_3$, THF (50%).

Scheme 2 Illustrates Preparation of Compound 3

Scheme 3 Illustrates Preparation of Compounds 6 and 7

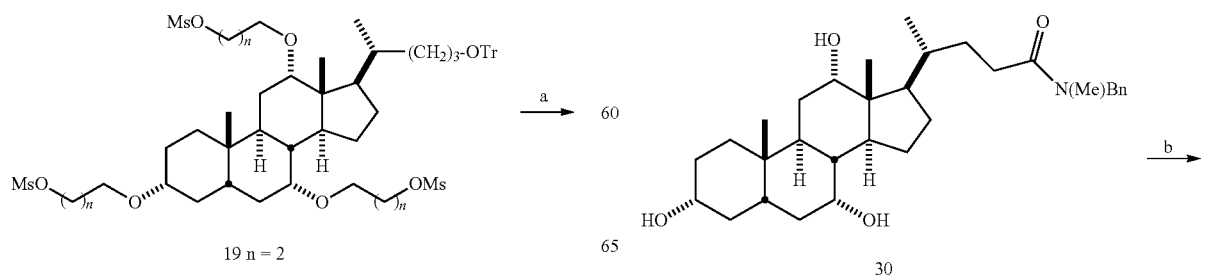

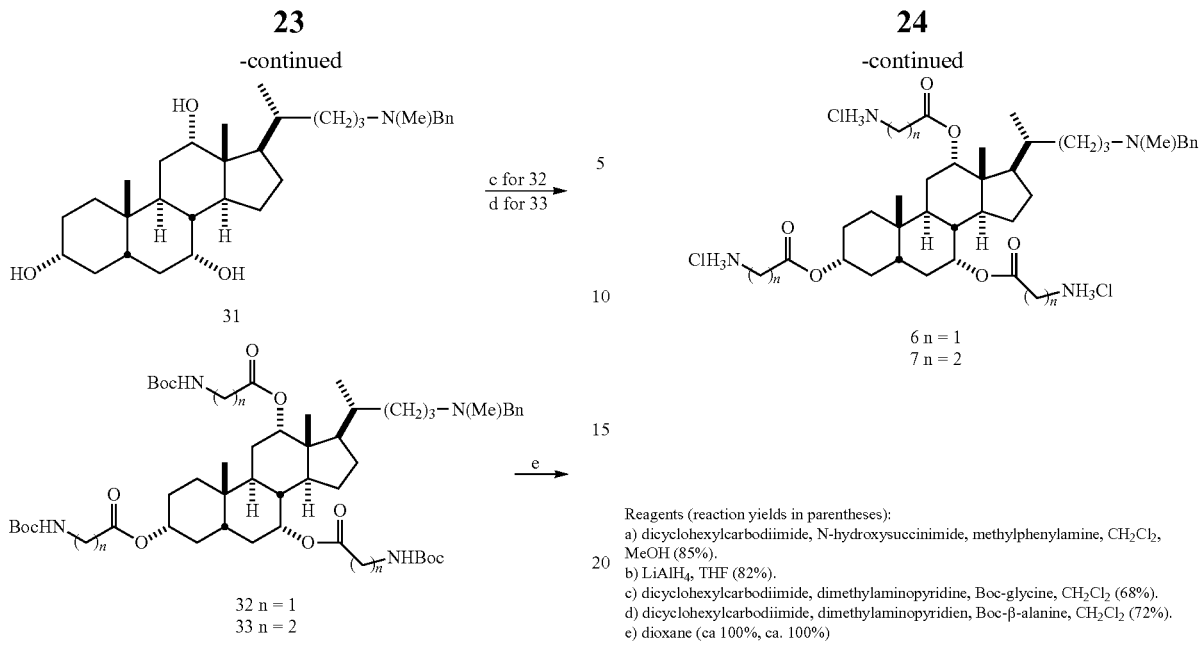
Reagents (reaction yields in parentheses):
a) dicyclohexylcarbodiimide, N-hydroxysuccinimide, methylphenylamine, $CH_2Cl_2$, MeOH (85%).
b) $LiAlH_4$, THF (82%).
c) dicyclohexylcarbodiimide, dimethylaminopyridine, Boc-glycine, $CH_2Cl_2$ (68%).
d) dicyclohexylcarbodiimide, dimethylaminopyridien, Boc-β-alanine, $CH_2Cl_2$ (72%).
e) dioxane (ca 100%, ca. 100%)
Scheme 4 Illustrates Synthesis of Compound 8
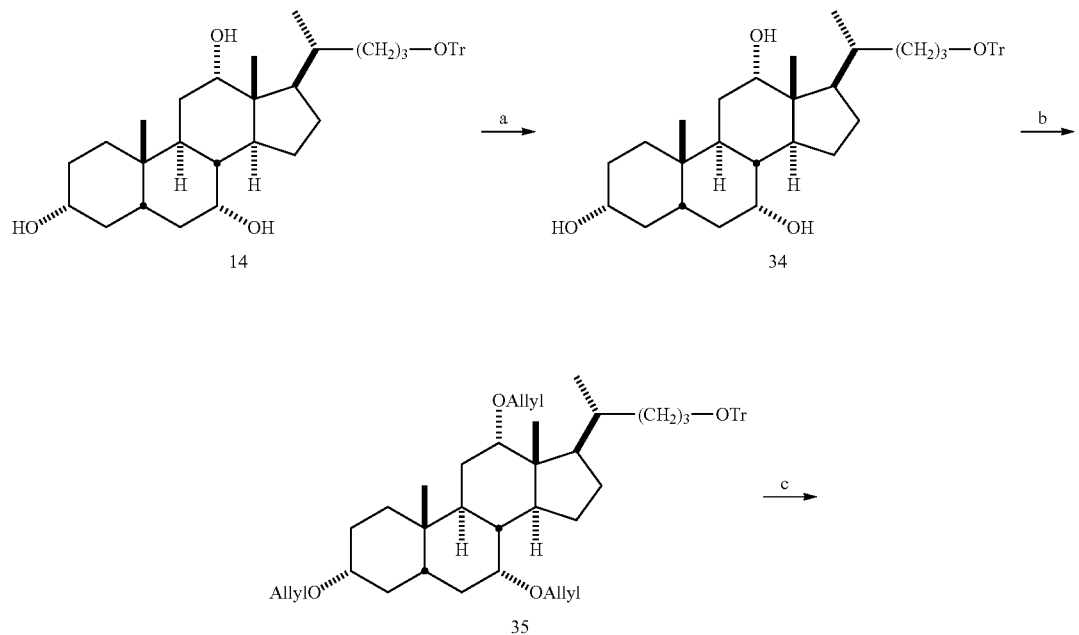
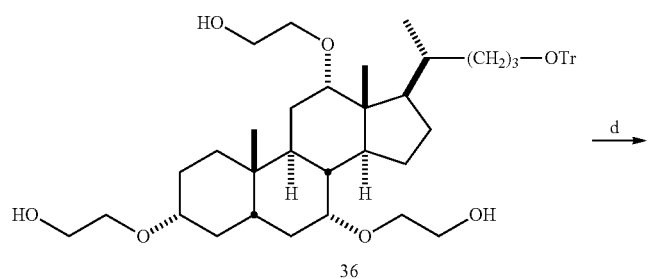

-continued
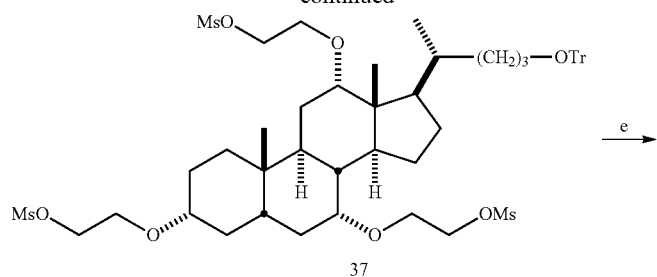
37
38
39
40

-continued

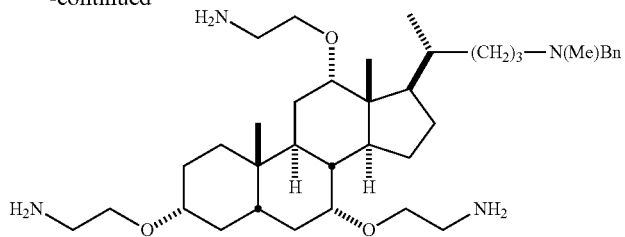

8

Reagents (reaction yields in parentheses):
a) DIAD, Ph₃P, p-nitrobenzoic acid, THF (85%); NaOH, MeOH (85%).
b) allylbromide, NaH, THF (79%).
c) O₃, CH₂Cl₂, MeOH; Me₂S; NaBH₄, (65%).
d) MsCl, CH₂Cl₂, Et₃N (86%).
e) NaN₃, DMSO (80%).
f) TsOH, MeOH (94%).
g) MsCl, CH₂Cl₂, Et₃N; N-benzylmethylamine (93%). g) LiAlH₄ THF (94%).

Scheme 5 Illustrates Synthesis of Compounds CSA-7 and CSA-8

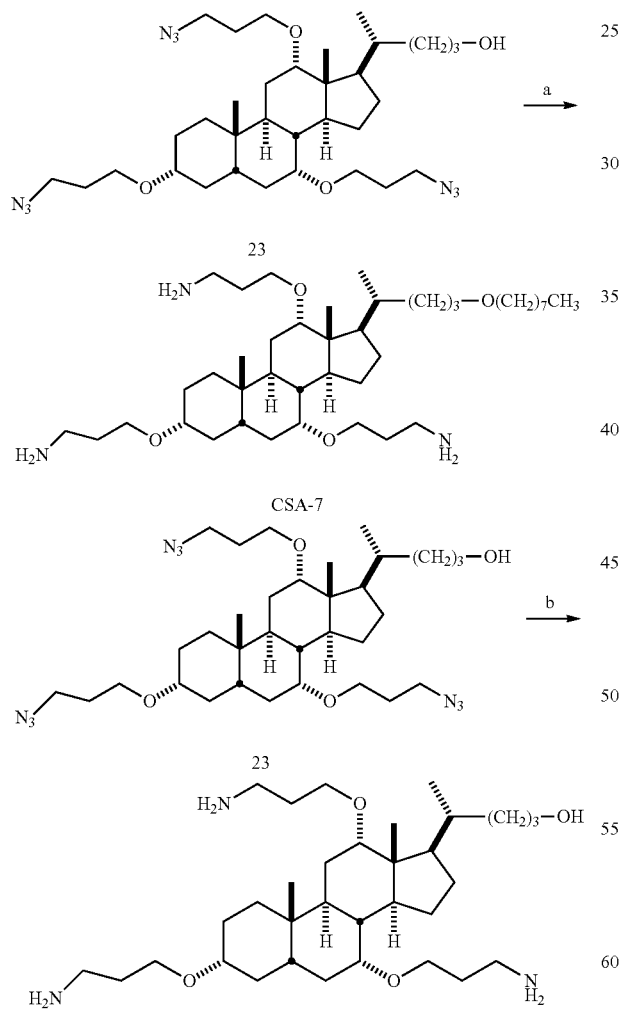

Reagents (reaction yields in parentheses): a) NaH, octylbromide, DMF (80%); LiAlH₄, THF (60%). b) LiAlH₄, THF (60%).

Scheme 6 Illustrates Synthesis of Compound CSA-11

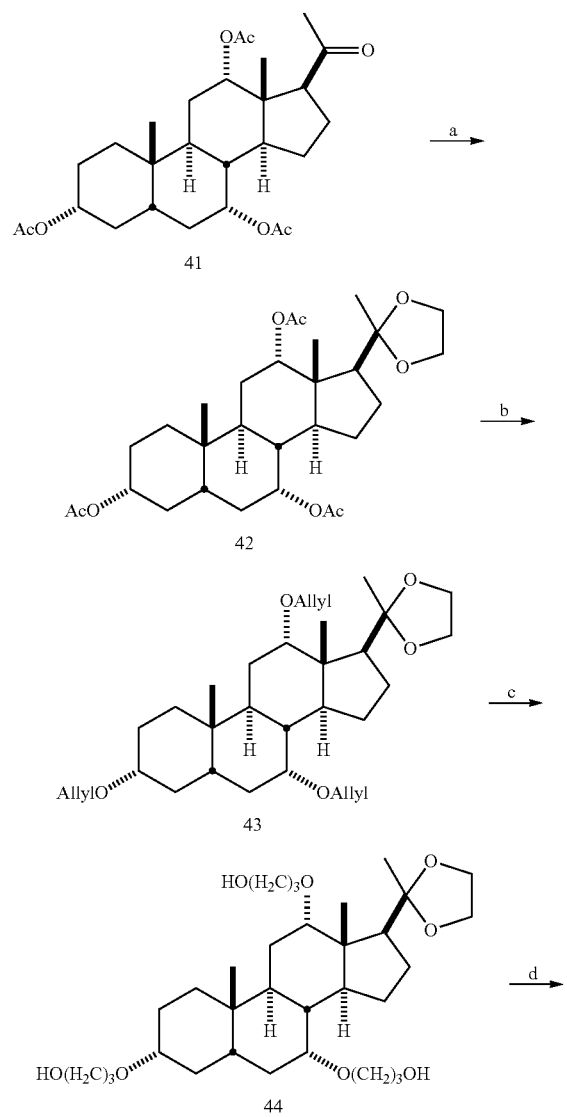

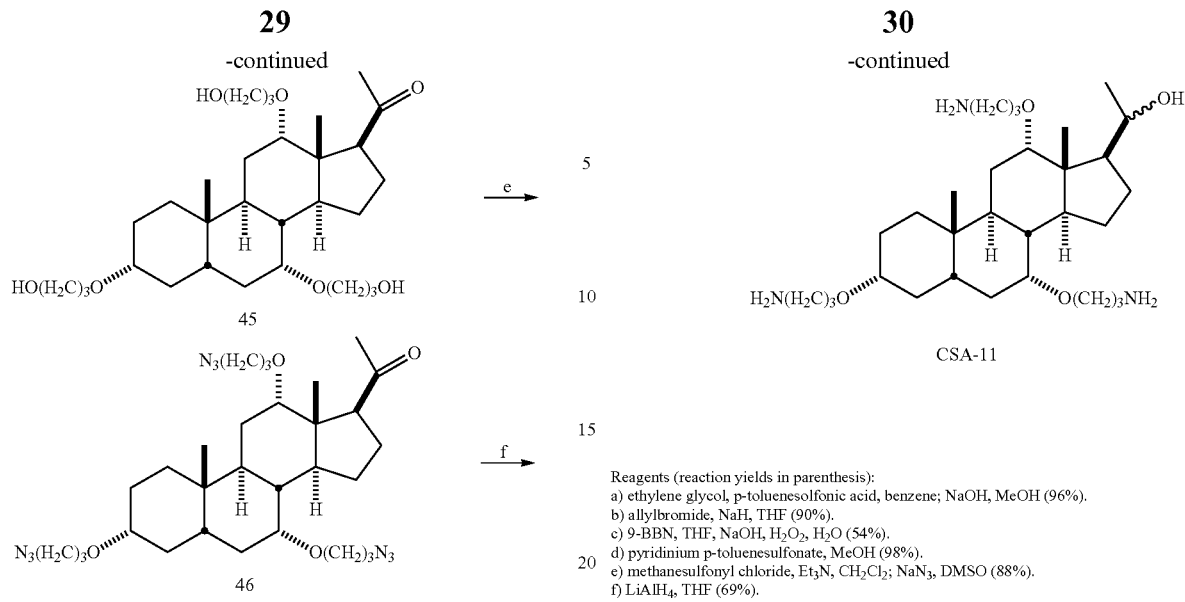

Reagents (reaction yields in parenthesis):
a) ethylene glycol, p-toluenesolfonic acid, benzene; NaOH, MeOH (96%).
b) allylbromide, NaH, THF (90%).
c) 9-BBN, THF, NaOH, $H_2O_2$, $H_2O$ (54%).
d) pyridinium p-toluenesulfonate, MeOH (98%).
e) methanesulfonyl chloride, $Et_3N$, $CH_2Cl_2$; $NaN_3$, DMSO (88%).
f) $LiAlH_4$, THF (69%).

Scheme 7 Illustrates Synthesis of Compound CSA-10

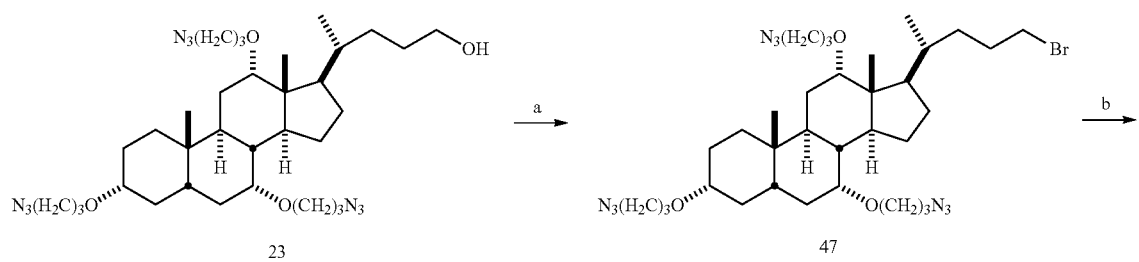

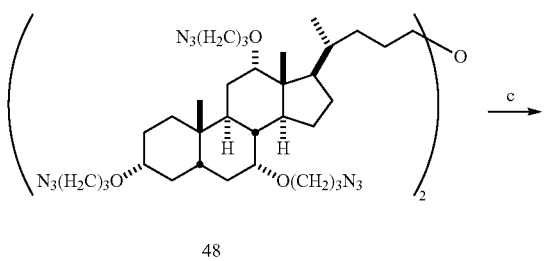

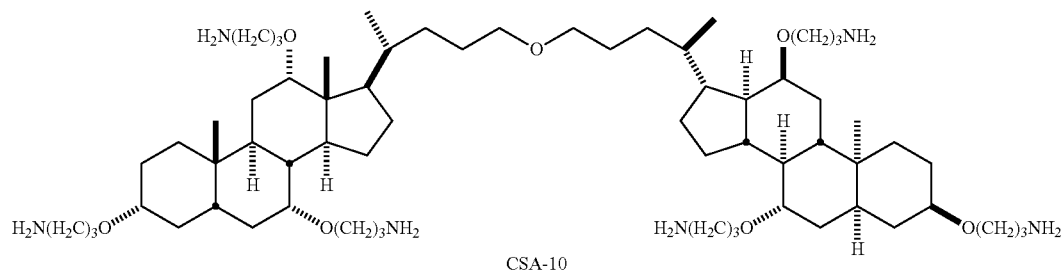

Reagents (reaction yields in parentheses):
a) methanesulfonylchloride, $Et_3N$, $CH_2Cl_2$; NaBr, DMF (97%).
b) 23, NaH, DMF (52%).
c) $LiAlH_4$, THF (76%).

Scheme 8
Illustrates Preparation of Compounds 111, CSA-17, 113 and CSA-7

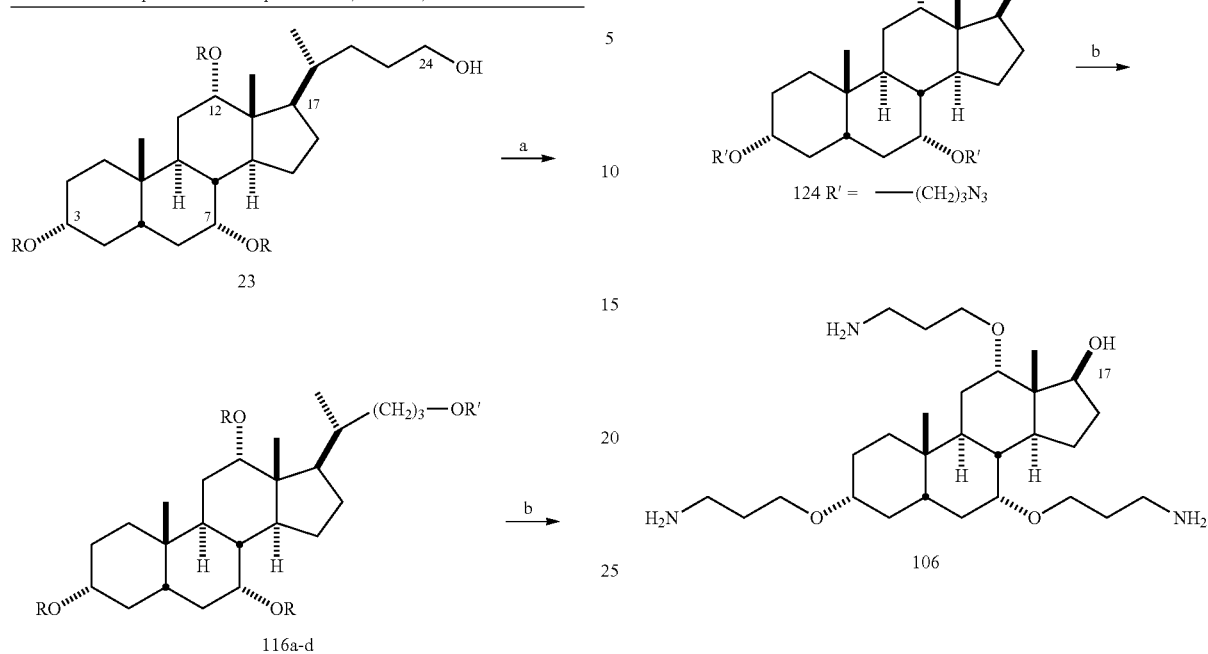

for 23, 116a-d, R = —(CH$_2$)$_3$N$_3$
for 116a, 111, R' = —CH$_3$
for 116b, CSA-17, R' = —(CH$_2$)$_2$CH$_3$
for 116c and 113, R' = —(CH$_2$)$_4$CH$_3$
for 116d and CSA-7, R' = —(CH$_2$)$_7$CH$_3$ Reagents (reaction yields, in parentheses):
a) NaH, DMF, CH$_3$I, CH$_3$(CH$_2$)$_2$Br, CH$_3$(CH$_2$)$_4$Br, or CH$_3$(CH$_2$)$_7$Br (85-90%).
b) LiAlH$_4$, THF (55-70%).

Scheme 9 Illustrates Preparation of Compound 106

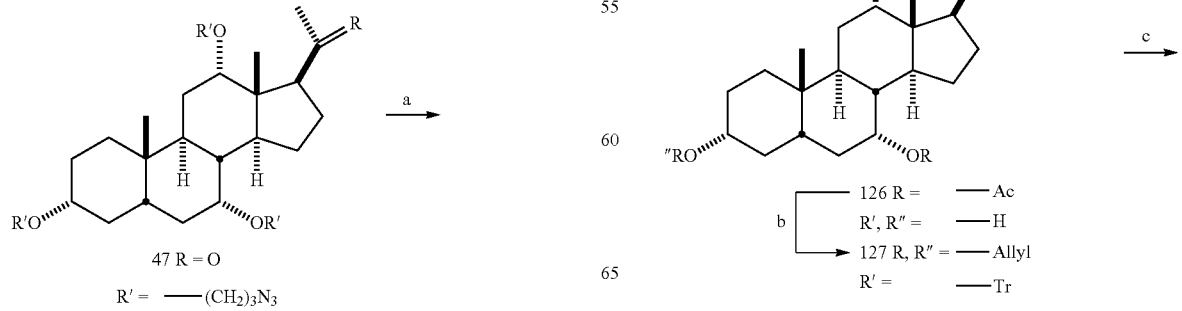

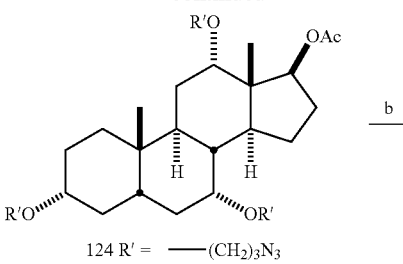

Reagents (reaction yields in parentheses): a) Urea-hydrogen peroxide complex, trifluoroacetic anhydride, CH$_2$Cl$_2$ (55%). B) NaOH, MeOH; LiAl$_4$, THF (43%).

Scheme 10 Illustrates Preparation of Compounds 108 and 109

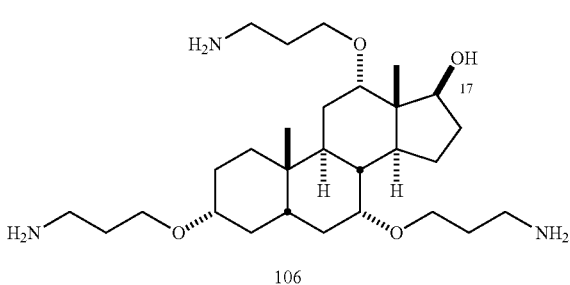

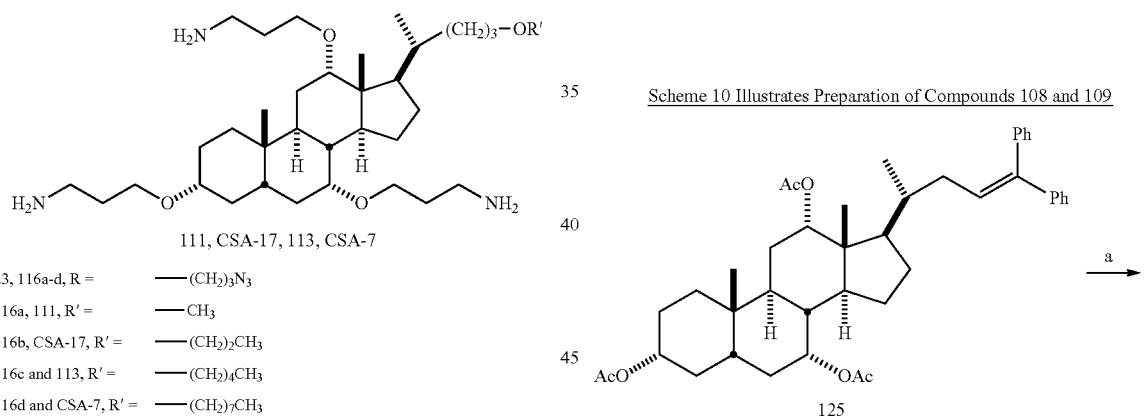

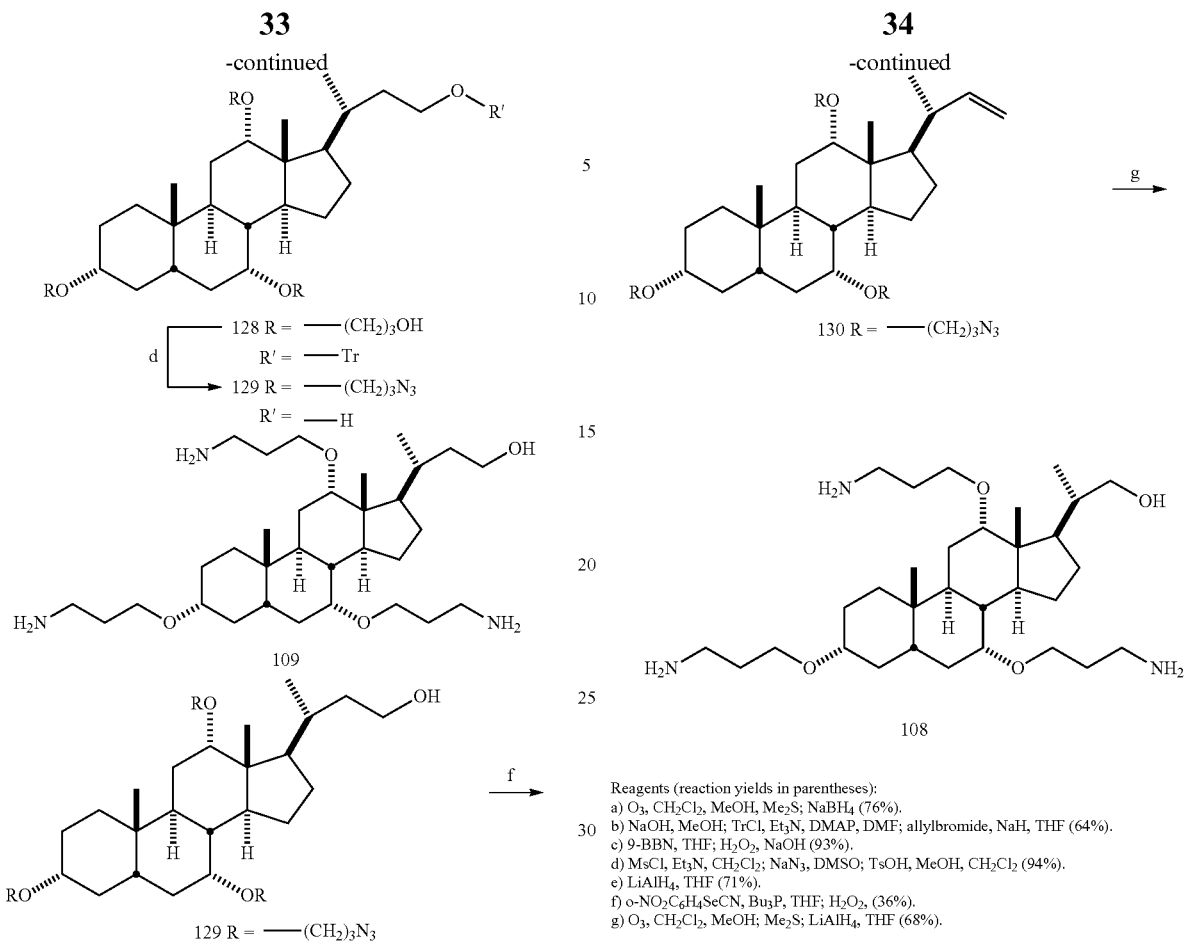

Reagents (reaction yields in parentheses):
a) O$_3$, CH$_2$Cl$_2$, MeOH, Me$_2$S; NaBH$_4$ (76%).
b) NaOH, MeOH; TrCl, Et$_3$N, DMAP, DMF; allylbromide, NaH, THF (64%).
c) 9-BBN, THF; H$_2$O$_2$, NaOH (93%).
d) MsCl, Et$_3$N, CH$_2$Cl$_2$; NaN$_3$, DMSO; TsOH, MeOH, CH$_2$Cl$_2$ (94%).
e) LiAlH$_4$, THF (71%).
f) o-NO$_2$C$_6$H$_4$SeCN, Bu$_3$P, THF; H$_2$O$_2$, (36%).
g) O$_3$, CH$_2$Cl$_2$, MeOH; Me$_2$S; LiAlH$_4$, THF (68%).

Scheme 11 Illustrates Preparation of Compounds 202 and 203

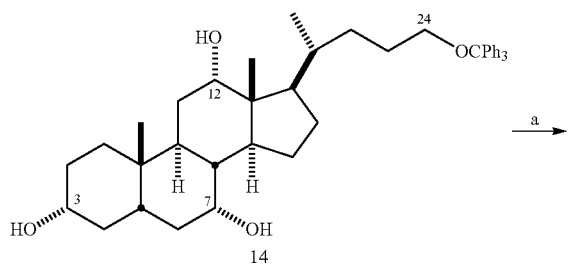

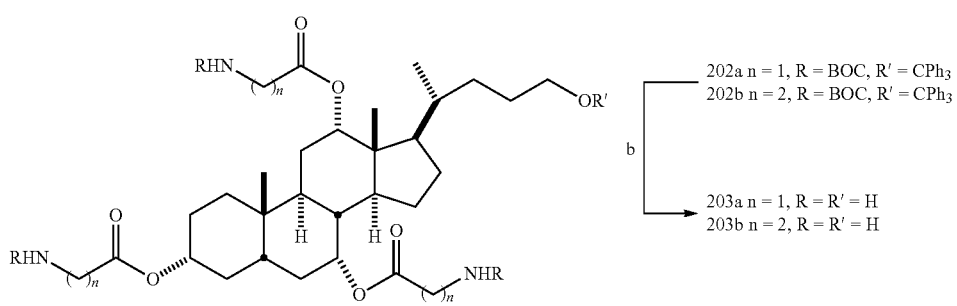

202a n = 1, R = BOC, R' = CPh$_3$
202b n = 2, R = BOC, R' = CPh$_3$ 203a n = 1, R = R' = H
203b n = 2, R = R' = H

Reagents (reaction yields in parentheses):
a) BOC-glycine or BOC-alanine, DCC, DMAP, CH$_2$Cl$_2$ (60%, 94%).
b) 4 M HCl in dioxane (74%, 71%).

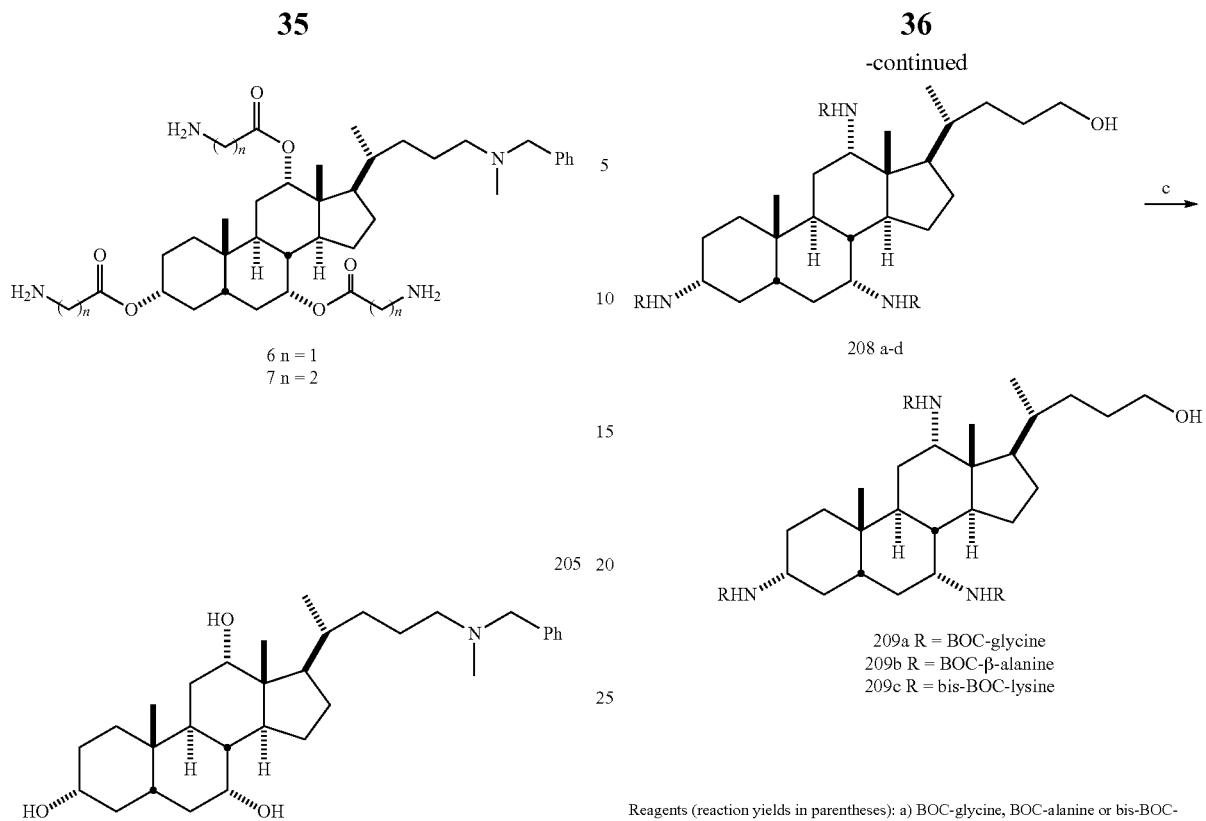
Reagents (reaction yields in parentheses): a) BOC-glycine, BOC-alanine or bis-BOC-lysine, DCC, DMAP, CH₂Cl₂. b) LiOH, THF, MeOH (71-85% for two steps). c) 4 M HCl in dioxane (ca. 100%)
Scheme 12 Illustrates Preparation of Compounds 209a-209c
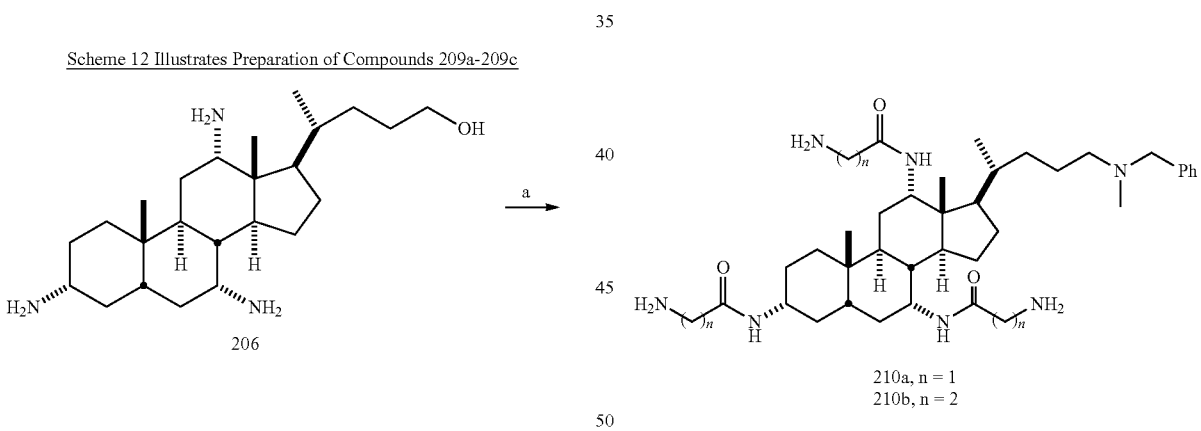
Scheme 13 Illustrates Preparation of Compound 206
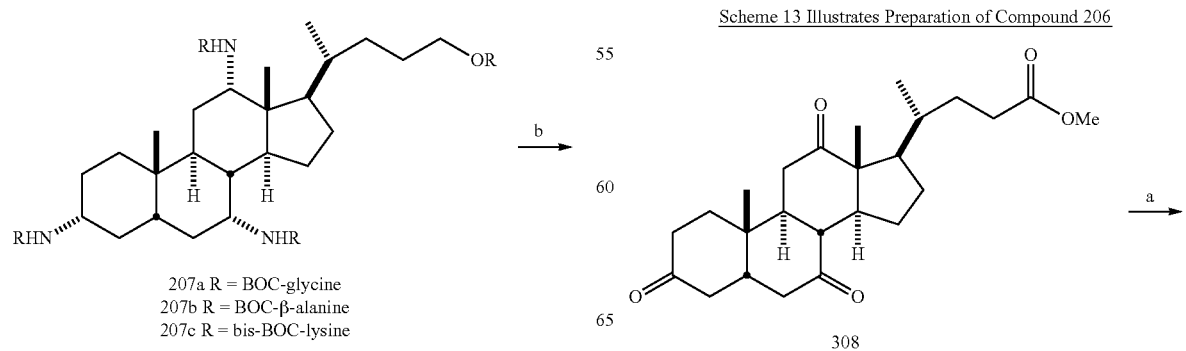

37
-continued
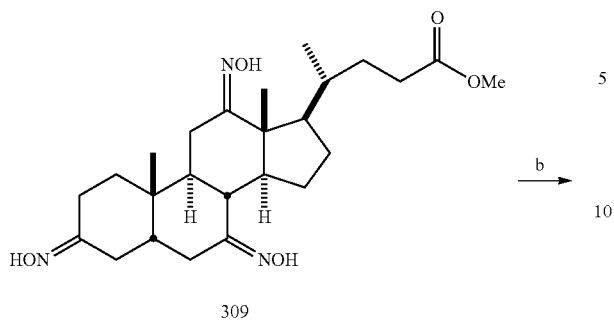
309
38
-continued
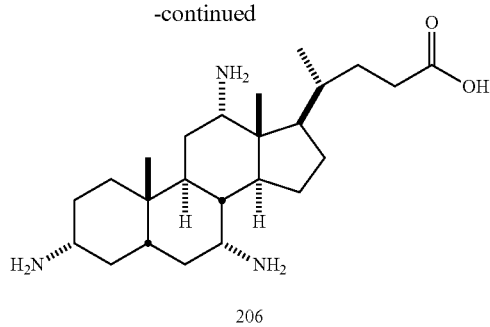
206
Reagents (reaction yields in parentheses): a) NH$_2$OH•HCl, AcONa., EtOH (97%). b) NaBH$_4$, TiCl$_4$, glyme (33%).
Scheme 14 Illustrates Syntheses of Compounds 324-326
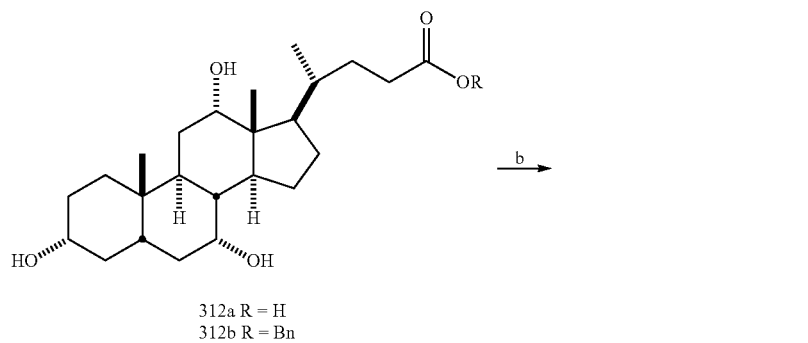
312a R = H
312b R = Bn
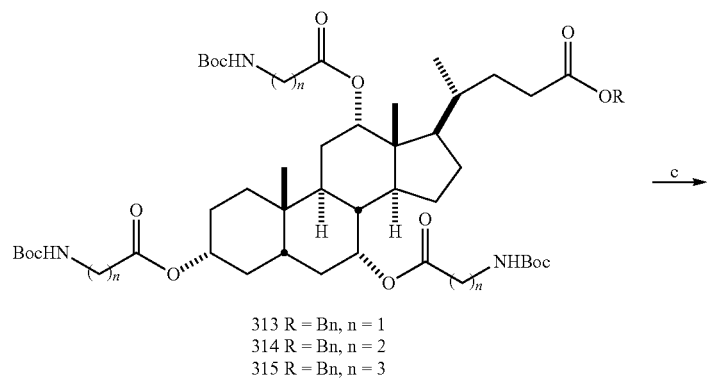
313 R = Bn, n = 1
314 R = Bn, n = 2
315 R = Bn, n = 3
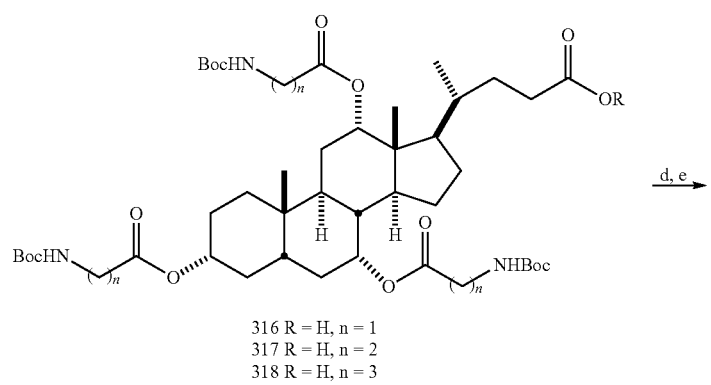
316 R = H, n = 1
317 R = H, n = 2
318 R = H, n = 3

-continued
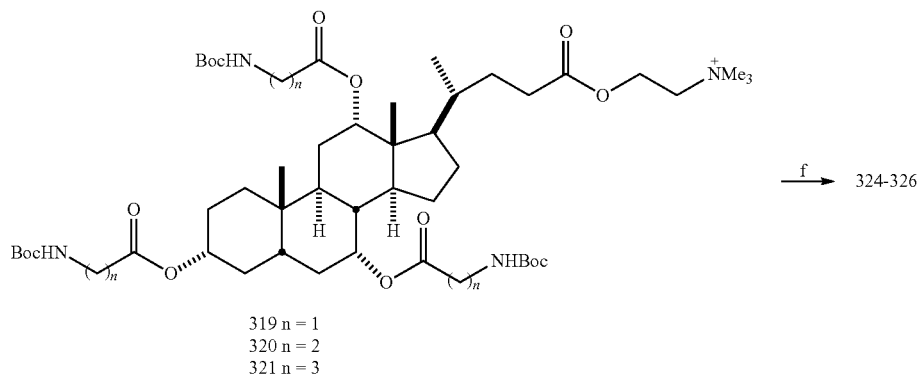
319 n = 1
320 n = 2
321 n = 3
Reagents (reaction yields in parentheses):
a) benzyl alcohol.
b) BOC-glycine, BOC-β-alanine or -BOC-γ-aminobutyric acid, DCC, DMAP, $CH_2Cl_2$ (68-78%).
c) $H_2$, Pd/C (97-99%).
d) $(CH_3)_2N(CH_2)_2OH$, DCC, DMAP, $CH_2Cl_2$ or THF (62-82%).
e) MeI, $CH_2Cl_2$.
f) HCl, dioxane (83-90% for two steps).
Scheme 15 Illustrates Syntheses of Compounds 341-343
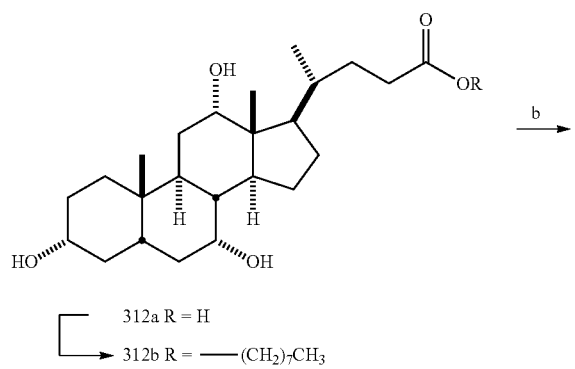
312a R = H
312b R = —$(CH_2)_7CH_3$
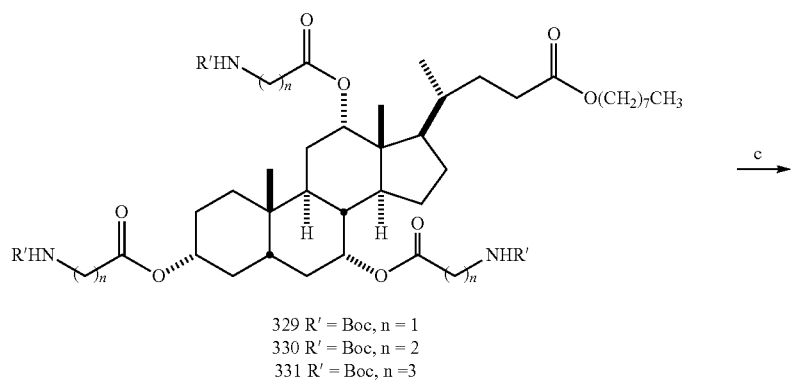
329 R' = Boc, n = 1
330 R' = Boc, n = 2
331 R' = Boc, n = 3

-continued
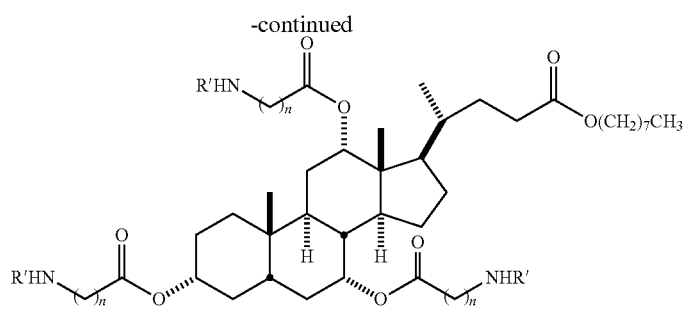
341 R' = H, n = 1
342 R' = H, n = 2
343 R' = H, n = 3
Reagents (reaction yields in parentheses): a) octanol, TsOH (73%).
b) Boc-glycine, BOC-β-alanine or-BOC-γ-aminobutyric acid, DCC, DMAP, CH$_2$Cl$_2$ (91-95%).
c) HCl, dioxane (84-99%).
Scheme 16 Illustrates Synthesis of Compound 356
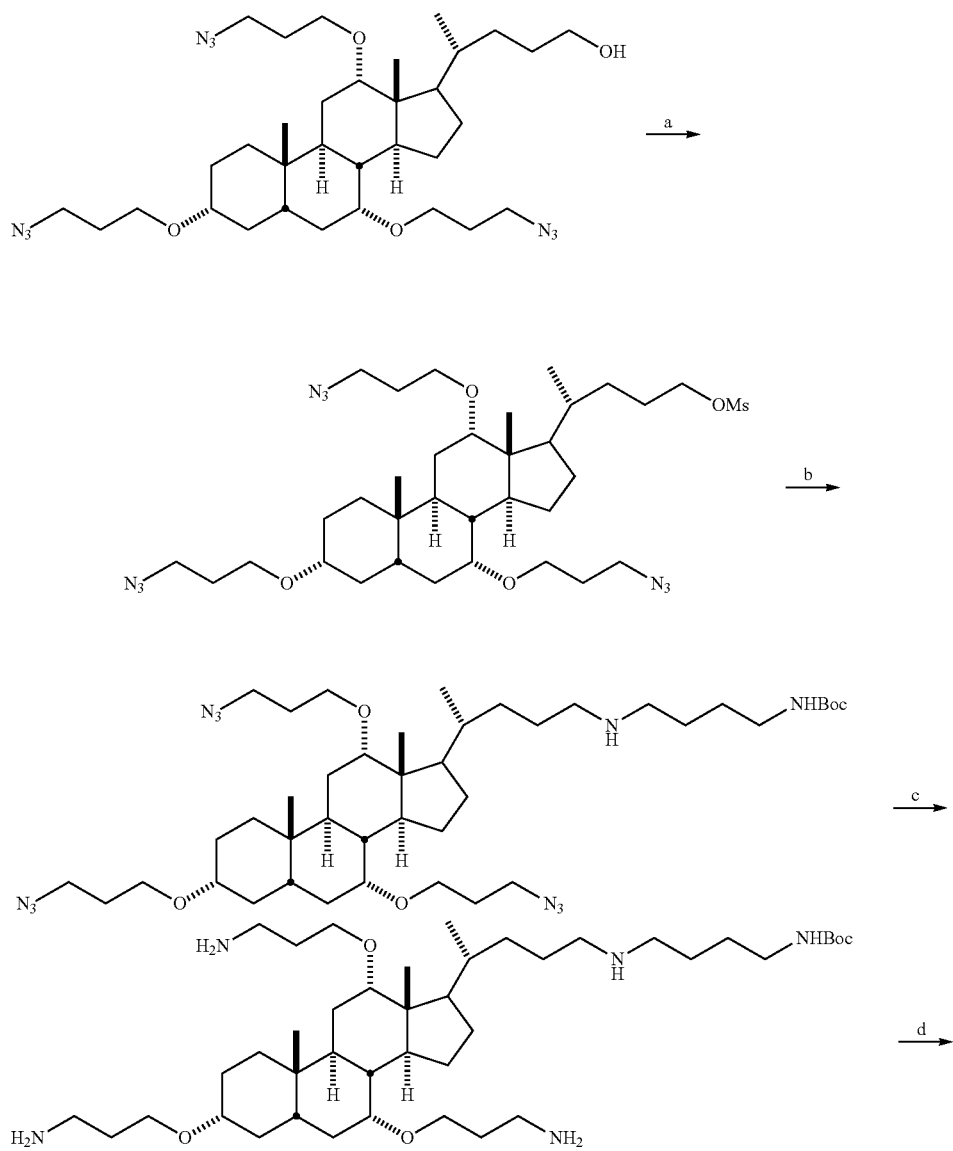

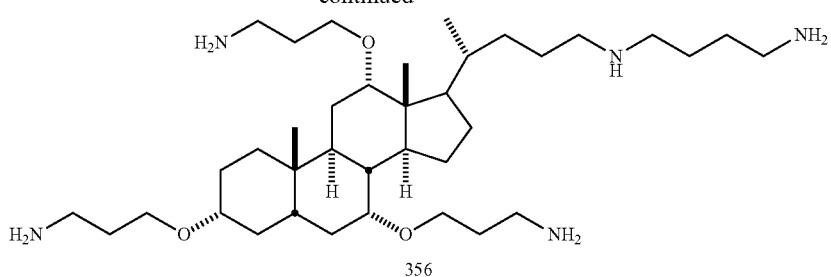
Reagents (reaction yields in parentheses):
a) MsCl, NEt3, CH2Cl2 (86%).
b) NH2(CH2)3NHBoc, THF (97%).
c) PPh3, THF/H2O, (86%).
d) HCl, 2M in ethyl ether, (89%).
Scheme 17 Illustrates Synthesis of Compound CSA-54
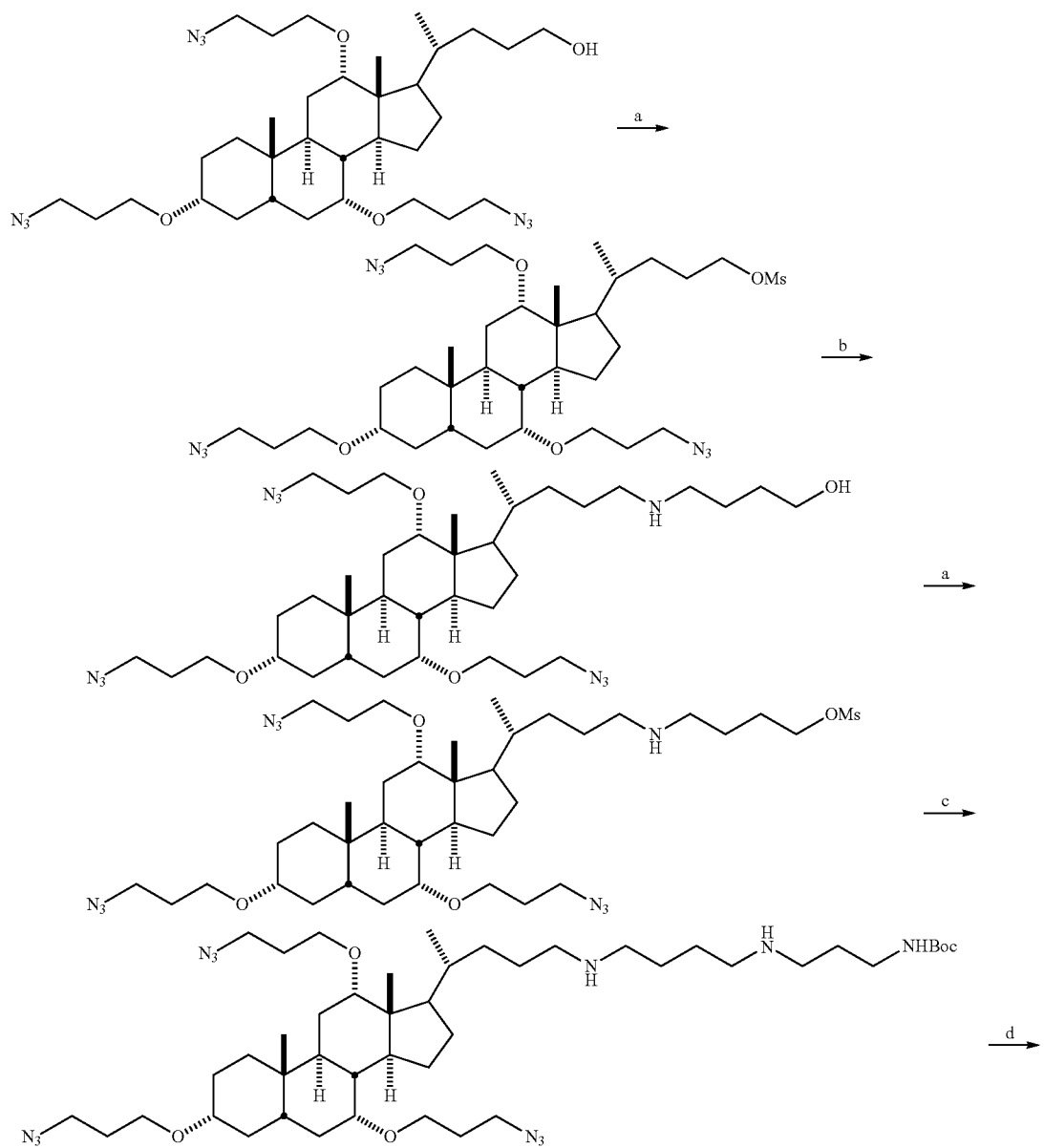

-continued

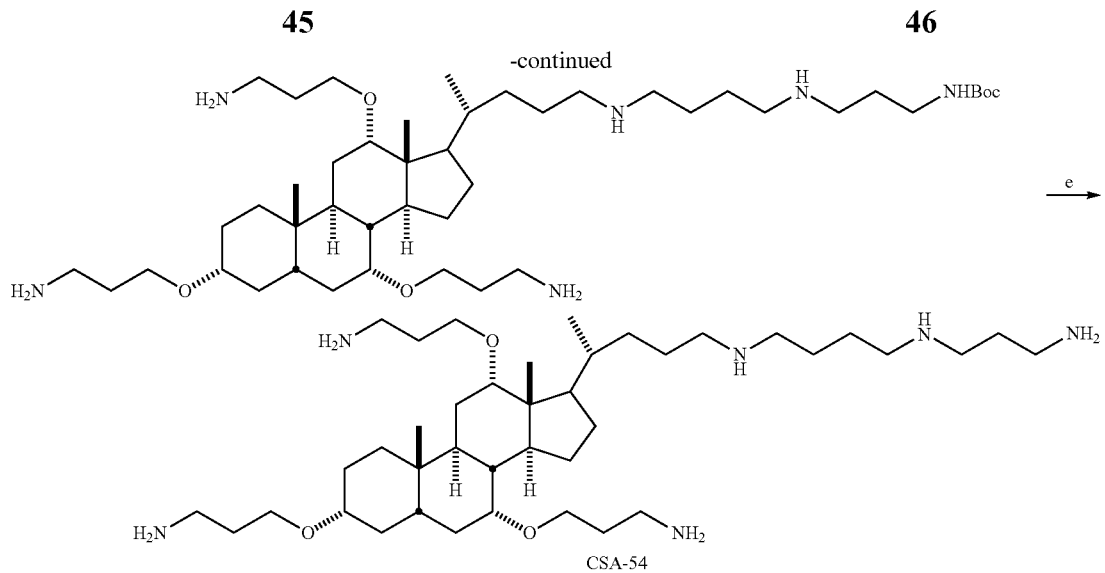

CSA-54

Reagents (reaction yields in parentheses):
a) MsCl, NEt₃, CH₂Cl₂ (86%).
b) NH₂(CH₂)₃OH, THF, then step a. (63%).
c) NH₂(CH₂)₃NHBoc, THF, (83%).
d) PPh₃, THF/H₂O, (90%).
e) HCl, 2M in ethyl ether, (94%).

Compounds of the invention and precursors to the compounds according to the invention are available commercially, e.g., from Sigm-Aldrich Co., St. Louis; Mo.; and Research Plus, Inc., Manasquan, N.J. Other compounds according to the invention can be synthesized according to methods dioscolsed herein, in U.S. Pat. Nos. 6,350,738; 6,486,148; and 6,767,904, and in the art.

Unless otherwise defined, all technical and scientific terms used herein have the same meaning as commonly understood by one of ordinary skill in the art to which this invention belongs. Although methods and materials similar or equivalent to those described herein can be used in the practice or study of the present invention, suitable methods and materials are described herein.

All of the features disclosed herein may be combined in any combination. Each feature disclosed in the specification may be replaced by an alternative feature serving a same, equivalent, or similar purpose. Thus, unless expressly stated otherwise, disclosed features (e.g., compound structures) are an example of a genus of equivalent or similar features.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a compound" or "a CSA" includes a plurality of compounds/CSAs and reference to "an infection" can include reference to one or more infections, and so forth.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 ug/kg, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 ug/kg, 2-9 ug/kg, 11.5-24.5 ug/kg, 26-49 ug/kg, 55-90 ug/kg, 125-400 ug/kg, 750-800 ug/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc. A series of ranges, for example, 1-10 ug/kg, 10-25 ug/kg, 25-50 ug/kg, 50-100 ug/kg, 100-500 ug/kg, 500-1,000 ug/kg, 1-5 mg/kg, 5-10 mg/kg, 10-20 mg/kg, 20-50 mg/kg, 50-100 mg/kg, 100-250 mg/kg, 250-500 mg/kg, includes 1-25 ug/kg, 10-25 ug/kg, 25-100 ug/kg, 100-1,000 ug/kg, 1-10 mg/kg, 1-20 mg/kg etc.

The invention is generally disclosed herein using affirmative language to describe the numerous embodiments. The invention also includes embodiments in which subject matter is excluded, in full or in part, such as substances or materials, method steps and conditions, protocols, or procedures. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. For example, salts, esters, ethers and amides of invention compounds disclosed herein are within the scope of this invention. Accordingly, the following examples are intended to illustrate but not limit the scope of invention described in the claims.

EXAMPLES

CSA compounds and intermediates were characterized using the following instruments: $^1$H and $^{13}$C NMR spectra were recorded on a Varian Gemini 2000 (200 MHz), Varian Unity 300 (300 MHz), or Varian VXR 500 (500 MHz)

spectrometer and are referenced to TMS, residual CHCl$_3$ ($^1$H) or CDCl$_3$ ($^{13}$C), or residual CHD$_2$OD ($^1$H), or CD$_3$OD ($^{13}$C). IR spectra were recorded on a Perkin Elmer 1600 FTIR instrument. Mass spectrometric data were obtained on a JOEL SX 102A spectrometer. THF solvent was dried over Na/benzophenone and CH$_2$Cl$_2$ was dried over CaH$_2$ prior to use. Other reagents and solvents were obtained commercially and were used as received.

Example 1

This example includes a description of various Materials and Methods.

CSA-13 was obtained from the Paul B. Savage laboratory, Department of Chemistry and Biochemistry, Brigham Young University, C100 BNSN, Provo, Utah 84602. Rats (Sprague-Dawley) and *staphylococcus aureus* bacteria (American type culture collection, ATCC 25923) were obtained from the National Institute of Health (NIH) Islamabad. The Animal ethics Committee of Institute gave an ethical approval for the animal studies. $^{99m}$Tc was obtained from locally produced fission based PAKGEN $^{99}$Mo/$^{99m}$Tc generator system. All the chemicals used were AR grade and purchased from Merck., Germany. Freeze dried kits of DTPA and Ciprofloxacin were obtained from "Kit Production Group", PINSTECH, Islamabad.

Radiolabeling of DTPA, Ciprofloxacin and CSA-13

DTPA kits contain 10 mg of diethylene triamine pentaacetic acid, 0.4 mg of SnCl$_2$.2H$_2$O and NaOH to make pH 7. 1.0 ml of Na$^{99m}$TcO$_4$ (8-10 mCi) was then added and incubated at room temperature for 20 min. Ciprofloxacin kits contain 3.8 mg of ciprofloxacin, 0.39 mg of SnCl$_2$.2H$_2$O, 4.4 mg of NaCl and 6 ml of acetate buffer pH 3.4 in 4.0 ml of H$_2$O, prepared as described (Obradovic, V., et al., *World J Nuc. Med* 2:269 (2003)). 2.0 ml of Na$^{99m}$TcO$_4$ (8-10 mCi) was then added and incubated at room temperature for 10 min. Stock solution of CSA-13 (2 mg/1 ml) was prepared in distilled water and 0.1 ml aliquots (~200 µg) of CSA-13 were stored at 4° C. CSA-13 was labelled with $^{99m}$Tc essentially as described by Samina Roohi et al., with minor modifications (Roohi S., et al., *Journal of Radioanalytical and nuclear chemistry* 267:561 (2006), (Roohi S., et al., *Radiochim Acta* 94:147 (2006), (Roohi S., et al., *Radiochim Acta* 93:415 (2005)). Briefly, aliquots were thawed at room temperature and mixed with SnCl$_2$.2H$_2$O (Merck). 1 ml of Na$^{99m}$TcO$_4$ in saline (5-10 mCi/ml) was added in the vials and incubated for 10 min at room temperature. The effect of labeling conditions i.e., pH, amount of reducing agents was also determined. To determine the optimal amount of reducing agent, 5-100 µg of SnCl$_2$.2H$_2$O was used; pH was adjusted by using HCl/NaOH. The stability of $^{99m}$Tc-CSA was checked for 4 hours at room temperature. Reaction mixture volume used in all studies was 1±0.1 ml. All the studies were carried out at room temperature (22±2° C.).

Quality Control

Radiochemical yields of $^{99m}$Tc-DTPA, $^{99m}$Tc-Ciprofloxacin and $^{99m}$Tc-CSA were assessed by thin layer chromatographic methods. In the case of $^{99m}$Tc-DTPA free $^{99m}$TcO$_4^-$ was determined by using Whatman paper No. 3 as the stationary phase and acetone as the mobile phase. Reduced and hydrolyzed activity was determined by using Whatman paper no. 3 as the stationary phase and saline as mobile phase. Free $^{99m}$TCO$_4^-$ in $^{99m}$Tc-Ciprofloxacin was determined by using Whatman paper No. 3 as the stationary phase and acetone as the mobile phase. Reduced and hydrolyzed activity was determined by using Whatman paper no. 3 as the stationary phase and citrate buffer of pH 3.8 as mobile phase. In the case $^{99m}$Tc-CSA free $^{99m}$TcO$_4^-$ was determined by using Whatman paper No. 3 as the stationary phase and acetone as the mobile phase. Reduced and hydrolyzed activity was determined by using instant thin layer chromatography (ITLC-SG strips) as the stationary phase and 0.05 M NaOH as mobile phase. Radiocolloids were also determined by passing the preparation through 0.22 µm sterile filters (Millipore Filter Corp). Activity remaining on the filter and in solution was counted in a gamma counter (Ludlum). The distribution of radioactivity on chromatographic stripes was measured by 2π Scanner (Berthold, Germany) or cut into 1 cm segments and counted in a gamma counter (Ludlum, USA).

Paper Electrophoresis

The charge of $^{99m}$Tc-CSA was determined by paper electrophoresis using Na-phosphate buffer of pH 6.8 as electrolyte and Whatman No. 1 as support. The sample was run at a constant voltage of 300V for 1 h. The strip was cut into 1 cm pieces and counted in a well type gamma counter. For comparison, a sample of Na$^{99m}$TcO$_4$ was also run under identical condition.

Microorganism (Bacteria *Staphylococcus aureus* 25923)

*S. aureus* ATCC 25923 is the most widely used quality control organism in clinical microbiology laboratories. Being a standard reference strain, its use was similar to that of previous studies (Welling M. M., et al., *Eur J Nucl Med* 27:292 (2000)). Overnight cultures of bacteria were prepared in brain heart infusion broth (BHI, Oxoid) in a shaking water bath at 37° C. Aliquots of suspensions containing viable stationary phase bacteria were flash frozen in liquid nitrogen and stored at −70° C. Just before use, an aliquot of this suspension was rapidly thawed in a water bath at 37° C. and diluted in sodium phosphate buffer of pH 7.2 (Na-PB).

In Vitro Binding of $^{99m}$Tc-CSA to Bacteria

Binding of $^{99m}$Tc-CSA to *S. aureus* bacteria was assessed by the method described elsewhere (Welling M. M., et al., *Eur J Nucl Med* 27:292 (2000)). Briefly, 0.1 ml of sodium phosphate buffer (Na-PB) containing $^{99m}$Tc-CSA was transferred to a test tube. 0.8 ml of 50% (v/v) of 0.01 M acetic acid in Na-PB containing approximately 1×10$^8$ viable bacteria was added. The mixture was incubated for 1 h at 4° C. and then centrifuged for 5 min at 2000 rev/min. The supernatant was removed and the bacterial pellet was gently resuspended in 1 ml of ice cooled Na-PB and recentrifuged. The supernatant was removed and the radioactivity in the bacterial pellet was determined by a gamma-counter. The supernatants were also counted. The radioactivity related to bacteria was expressed in percent of the added $^{99m}$Tc activity bound to viable bacteria in regard to total $^{99m}$Tc activity (Table 1). For comparison purposes binding of $^{99m}$Tc-DTPA and $^{99m}$Tc-Ciprofloxacin to bacteria were also performed following the reported procedures (Sonmezonglu K., et al., *J Nucl Med* 42:567 (2001); (Vinjamuri S., et al., *Eur J Nucl Med* 347:233 (1996); (Oh S. J., et al., *Appl Radiation Isotopes* 57:193 (2002)).

Thigh Muscle Infection

Male Sprague-Dawley rats weighing ~200 g were used in all animal studies. A turbid suspension containing 2×10$^8$ colony-forming units (cfu) of *S. aureus* in 0.1 ml of saline was injected into the left thigh muscle of the rats. 48 h later, when visible swelling appeared in the infected thigh, 0.2 ml of $^{99m}$Tc-CSA (~1 mCi) was injected via the tail vein. Four rats were used for one set of studies. Similar method was followed using $^{99m}$Tc-Ciprofloxacin.

Biodistribution Study

After a definite time, the rats were sacrificed after ether anesthesia and biodistribution was determined. The whole animals were then weighed and dissected. Samples of infected muscle, normal muscle, liver, spleen, lung, kidney, stomach, and heart were weighed, and the activity was measured using a gamma counter (Table 2). The results were expressed as the percent uptake of injected dose per organ. The results of the bacterial uptake of $^{99m}$Tc-CSA were analyzed by an analysis of variance and compared with $^{99m}$Tc-Ciprofloxacin (Table 2). The level of significance was set at 0.05.

$^{99m}$Tc-CSA Scintigraphy

Scintigraphy was performed in the rats infected with the S. aureus infection in the thigh of left legs as described above. A single headed (Siemens Integrated ORBITER) Gamma Camera System interfaced with high-resolution parallel whole collimator was used. It was connected to an on-line dedicated computer (Macintosh® Operating System 7.5 Software used on the ICON™ Workstation). Each animal was placed on a flat hard surface with both hind legs spread out and all legs fixed with surgical tape. Saline (0.5 ml) containing ~0.4 mCi of $^{99m}$Tc-CSA was then injected intravenously into the tail vein. Immediately after injection, dynamic acquisition with both thighs in focus was done for 60 min. For the biodistribution study of the radiotracer, whole body acquisition was done at 1 h and 4 h after injection.

Example 2

This example includes a description of radiolabeling of a CSA.

Labeling efficiency and radiochemical purity and stability were assessed by a combination of ascending paper chromatography and instant thin layer chromatography on silica gel. In paper chromatography using acetone as the solvent, free $^{99m}$TcO$_4^-$ moved towards the solvent front (Rf=1), while $^{99m}$Tc-CSA and reduced/hydrolyzed $^{99m}$Tc remained at the point of spotting. In ITLC-SG chromatography using 0.05M NaOH as the solvent, reduced/hydrolyzed $^{99m}$Tc remained at the point of spotting, whereas $^{99m}$Tc-CSA and free $^{99m}$TcO$_4^-$ moved towards the solvent front. Radiocolloids were also determined by passing the preparation through sterile filters (0.22 nm). In this technique radiocolloids were retained on the filter, while $^{99m}$Tc-CSA and free $^{99m}$TcO$_4^-$ passed through. The results obtained by both methods were in excellent agreement. The amount of radiocolloid in the final preparations was ≤2.0%.

The effects of pH are shown in FIG. 2. At low pH (2-4), the labeling efficiency was 100%, while at pH 7 the labeling efficiency of $^{99m}$Tc-CSA was <97%. In basic media at pH 10 the labeling efficiency was decreased to 95%. Hence further studies were performed at pH 4.

Figure 4:
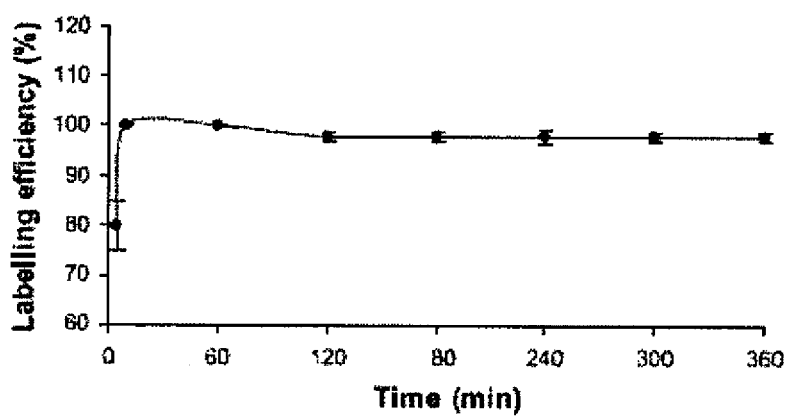
FIG. 4: Rate of complexion of $^{99m}$Tc with CSA-13 and stability of $^{99m}$Tc-CSA (n=4).

The amount of the reducing agent, SnCl$_2$.2H$_2$O, which gave the highest labeling efficiency, was 15-60 µg (FIG. 3). To avoid colloid formation, the optimum amount of reducing agent (30 µg) was used. The complexation of $^{99m}$Tc with CSA was rapid and maximum labeling efficiency was achieved after 10 min. The resulting complex of $^{99m}$Tc-CSA was quite stable and labeling of ≥98% is maintained for up to 6 h (FIG. 4). Paper electrophoresis showed that the $^{99m}$Tc-CSA species does not move to cathode or anode indicating that the compound exhibits neutral behavior (FIG. 5). The final formulation for the radiotracer $^{99m}$Tc-CSA was: CSA: 200 µg; SnCl$_2$.2H$_2$O: 30 µg; pH 4; $^{99m}$Tc ~10 mCi; reaction mixture volume ~1 ml; and incubation time 10 min at room temperature. Radiolabeling efficiency of $^{99m}$Tc-CSA monitored by paper and ITLC-SG was higher than 97%. The resulting complex of $^{99m}$Tc-CSA is quite stable and labeling of ≥98% is maintained for up to 4 h. No post-labeling purification was required. The biological activity (in vitro) of $^{99m}$Tc-CSA is significantly higher than $^{99m}$Tc-Ciprofloxacin. $^{99m}$Tc-CSA is able to localize in bacterial infection induced by S. aureus in animal models and may be used in a variety of patients referred for infection Example 3

This Example describes in vitro and in vivo binding of labeled CSA to Staphylococcus aureus.

Figure 7:
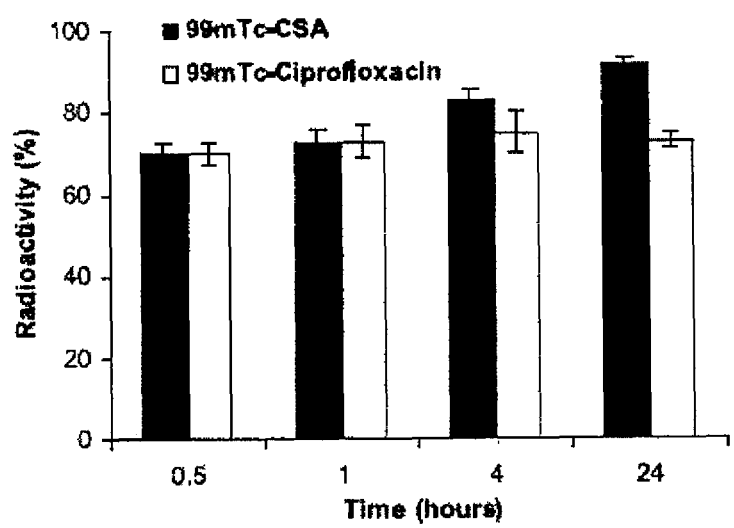
FIG. 7: In-vitro binding of $^{99m}$Tc-CSA to viable *S. aureus* in comparison with $^{99m}$Tc-Ciproflaxin at 50 µg concentration (n=4 per study).

In vitro binding of 10 µg of $^{99m}$Tc-CSA was in the range of 96.3% at 0.5 h, which decreased to 90% after 24 h. In-vitro binding of 50 µg and 100 µg $^{99m}$Tc-CSA was 70% and 63% respectively at 30 min; however, maximum binding with S. aureus was achieved after 24 h (>90%) (FIG. 6). In-vitro binding of $^{99m}$Tc-Ciprofloxacin, a promising agent for the diagnosis of bacterial infection, to bacteria at 50 µg $^{99m}$Tc-Ciprofloxacin concentration was observed as 70%±4.0 (FIG. 7, Table 1). In vitro binding of $^{99m}$Tc-DTPA (kidney/brain imaging agent) to bacteria at 10 µg $^{99m}$Tc-DTPA concentration was ~10% (FIG. 7, Table 1). In published reportes, the in-vitro binding of $^{99m}$Tc-Ciprofloxacin and $^{99m}$Tc-DTPA ranged from 40 to 65% and >8% respectively (Obradovic, V., et al., *World J Nuc. Med* 2:269 (2003), (Corn, M. J., et al., *Acad Sci* 76:27 (1958)).

TABLE 1

Table 1. In-vitro binding of $^{99m}$Tc-CSA to viable S. aureus in comparison with $^{99m}$Tc-Ciprofloxacin (n = 4 per study).

| | Conc. (µg) | Time (hrs) | | | |
|---|---|---|---|---|---|
| | | 0.5 | 1 | 4 | 24 |
| $^{99m}$Tc-CSA | 10 | 96.3 ± 3.0 | 99.4 ± 0.05 | 90 ± 5.0 | 90.6 ± 6.67 |
| | 50 | 70 ± 6.6 | 73 ± 2.78 | 83 ± 4.75 | 92 ± 7.70 |
| | 100 | 63 ± 5.05 | 60 ± 6.0 | 72 ± 5.9 | 94 ± 4.05 |
| $^{99m}$Tc-Ciprofloxacin | 10 | | | | |
| | 50 | 70 ± 4.0 | 73 ± 4.0 | 75 ± 4.5 | 73 ± 5.0 |
| | 100 | | | | |

Figure 8:
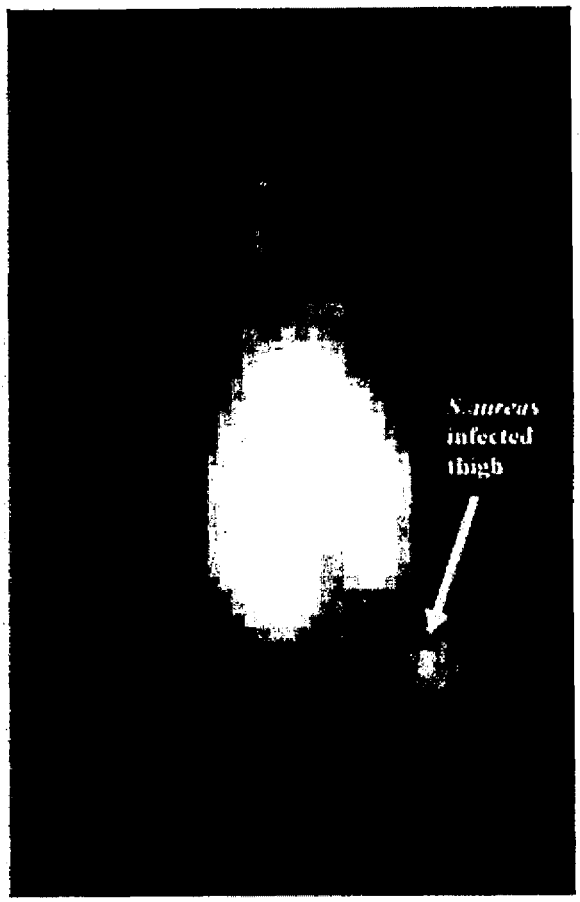
FIG. 8: Scintigram of a rat at 4 hours after administration of $^{99m}$Tc-CSA showing *S. aureus* lesion in left thigh muscles.

The tissue distribution of $^{99m}$Tc-CSA in rats with bacterial infection was studied at 1 and 4 h after intravenous administration, and results are presented in Table 2. The tissue distribution is expressed as percentage of injected dose per organ (% ID/organ). The $^{99m}$Tc-CSA was rapidly distributed after intravenous injection and liver and spleen uptake was significant after 1 h and remained high after 4 h. However, the lung lung shows a significant uptake after 4 h. It is assumed that $^{99m}$Tc-CSA is stable in vivo, since insignificant activity was noticed in thyroid and stomach during biodistribution studies. FIG. 8 shows the infected thigh muscles and normal thigh muscles obtained at 4 h after administration of $^{99m}$Tc-CSA. The infected thigh/normal thigh radioactivity ratio indicated that higher binding affinity to the infection induced with S. aureus was observed. The highest target/non-target ratio reached 1.6 at 1 h and remained 2.4 at 4 h post injection of $^{99m}$Tc-CSA, comparable to the $^{99m}$Tc-Ciprofloxacin which showed a value of 2.0 at 4 hours post injection time (Table 2).

TABLE 2

Table 2. Biodistribution data in percent injected dose per organ for $^{99m}$Tc-CSA and $^{99m}$Tc-Ciprofloxacin after 4 hours post injection in infected Sprauge-Dawley rats (n = 4).

| Organ | $^{99m}$Tc-CSA | $^{99m}$Tc-Ciprofloxacin |
|---|---|---|
| Infected thigh/Normal thigh | 2.3 ± 0.3 | 2.0 ± 0.5 |
| Liver | 93 ± 0.8 | 13.4 ± 0.8 |
| Spleen | 1.22 ± 0.05 | 0.4 ± 0.0 |

TABLE 2-continued

Table 2. Biodistribution data in percent injected dose per organ for $^{99m}$Tc-CSA and $^{99m}$Tc-Ciprofloxacin after 4 hours post injection in infected Sprauge-Dawley rats (n = 4).

| Organ | $^{99m}$Tc-CSA | $^{99m}$Tc-Ciprofloxacin |
|---|---|---|
| Stomach | 0.080 ± 0.02 | 0.6 ± 0.1 |
| Lungs | 0.41 ± 0.09 | 0.3 ± 0.0 |
| Kidney | 0.52 ± 0.05 | 8.9 ± 0.4 |
| Bladder | 0.016 ± 0.0 | 42.98 ± 4.0 |
| Heart | 0.066 ± 0.01 | 0.1 ± 0.0 |

A whole body image of the infected rat at 4 hours after $^{99m}$Tc-CSA administration is presented in FIG. 8. *S. aureus* infection in rat thigh was visualized as area of increased tracer accumulation after injection of labeled CSA. The infection was not clearly visible at 1 h post administration, whereas it was clearly visible after 4 hours. Target-to-background ratios obtained from region of interest analysis of $^{99m}$Tc-CSA ranged 1.6 to 2.4. In vitro studies and animal studies have shown that $^{99m}$Tc-CSA localizes in bacteria infected sites significantly. Due to the ease of $^{99m}$Tc-CSA preparation and infection uptake, it may be used similar to $^{99m}$Tc-Ciprofloxacin in a variety of patients referred for infection (Britton K. E., et al., *Eur J Nucl Med* 24:553 (1997); (Das, S. S., et al., *World J Nucl Med* 2:173 (2003); (Larikka, M. J., et al., *Nucl Med Commun* 23:167 (2002); (Corstens, F. H., et al., *Lancet* 354 (1997)). However; further studies are needed in this direction.

Example 4

This example includes a description of one or more exemplary synthetic procedures for obtaining Compounds 1-5, 13-20 and 22-27.

Compound 13: To a 1 L round-bottom flask were added methyl cholate (30.67 g, 72.7 mmol) in dry THF (600 mL) and LiAlH$_4$ (4.13 g, 109 mmol). After reflux for 48 hours, saturated aqueous Na$_2$SO$_4$ (100 mL) was introduced slowly, and the resulted precipitate was filtered out and washed with hot THF and MeOH. Recrystallization from MeOH gave colorless crystals of 13 (28.0 g, 98% yield). m.p. 236.5-238° C.; IR (KBr) 3375, 2934, 1373, 1081 cm$^{-1}$; $^1$H NMR (CDCl$_3$/MeOH-d$_4$, 200 MHz) δ 3.98 (bs, 1 H), 3.83 (bs, 1 H), 3.60-3.46 (m, 2 H), 3.38 (bs, 5 H), 2.30-2.10 (m, 2 H), 2.05-1.05 (series of multiplets, 22 H), 1.03 (bs, 3 H), 0.92 (s, 3 H), 0.71 (s, 3 H); $^{13}$C NMR (CDCl$_3$/MeOH-d$_4$, 50 MHz) δ 73.89, 72.44, 68.99, 63.51, 48.05, 47.12, 42.49, 40.37, 39.99, 36.62, 36.12, 35.58, 35.40, 32.77, 30.69, 30.04, 29.02, 28.43, 27.27, 23.96, 23.08, 18.00, 13.02; HRFAB-MS (thioglycerol+Na$^+$ matrix) m/e: ([M+Na]$^+$) 417.2992 (55.3%); calcd. 417.2981.

Compound 14: To a round-bottom flask were added 13 (28.2 g, 71.7 mmol) in DMF (300 ml), Et$_3$N (20 mL, 143.4 mmol), trityl chloride (25.98 g, 93.2 mmol) and DMAP (0.13 g, 1.07 mmol). The mixture was stirred at 50° C. under N$_2$ for 30 hours followed by the introduction of water (1000 mL) and extraction with EtOAc (5×200 mL). The combined extracts were washed with water and brine and then dried over MgSO$_4$. After removal of solvent in vacuo, the residue was purified using SiO$_2$ chromatography (CH$_2$Cl$_2$, Et$_2$O and MeOH as eluents) to give 14 as a pale yellow solid (31.9 g, 70% yield). m.p. 187° C. (decomposition); IR (KBr) 3405, 2935, 1448, 1075 cm$^{-1}$; $^1$H NMR (CDCl$_3$, 200 MHz) δ 7.46-7.42 (m, 6 H), 7.32-7.17 (m, 9 H), 3.97 (bs, 1 H), 3.83 (bs, 1 H), 3.50-3.38 (m, 1 H), 3.01 (bs, 1 H), 2.94 (dd, J=14.2, 12.2 Hz, 2 H), 2.64 (bs, 1 H), 2.51 (bs, 1 H), 2.36-2.10 (m, 2 H), 2.00-1.05 (series of multiplets, 22 H), 0.96 (d, J=5.8 Hz, 3 H), 0.87 (s, 3 H), 0.64 (s, 3 H); $^{13}$C NMR (CDCl$_3$, 50 MHz) δ 144.77, 128.93, 127.91, 127.01, 86.43, 73.35, 72.06, 68.66, 64.28, 47.47, 46.53, 41.74, 41.62, 39.64, 35.57, 35.46, 34.91, 34.82, 32.40, 30.55, 28.21, 27.69, 26.80, 26.45, 23.36, 22.59, 17.83, 12.61; HRFAB-MS (thioglycerol+Na$^+$ matrix) m/e: ([M+Na]$^+$) 659.4069 (100%); calcd. 659.4076.

Compound 15: To a round-bottom flask were added 14 (20.0 g, 31.4 mmol) in dry THF (600 mL) and NaH (60% in mineral oil, 6.3 g, 157.2 mmol). The mixture was refluxed for 30 min under N$_2$ followed by addition of allyl bromide (27 mL, 314 mmol). After 60 hours of reflux, additional NaH (3 eq.) and allyl bromide (4 eq.) were added. Following another 50 hours of reflux, water (20 mL) was introduced slowly followed by addition of 1% HCl until the aqueous layer became neutral. The mixture was then extracted with ether (3×100 mL) and the combined extracts were washed with water (100 mL) and brine (2×100 mL). The ether solution was dried over anhydrous Na$_2$SO$_4$, and after removal of solvent, the residue was purified using SiO$_2$ chromatography (hexanes and EtOAc/hexanes 1:8 as eluents) to give 15 (22.76 g, 96% yield) as a pale yellow glass. IR (neat) 2930, 1448, 1087 cm$^{-1}$; $^1$H NMR (CDCl$_3$, 200 MHz) δ 7.48-7.30 (m, 6 H), 7.32-7.14 (m, 9 H), 6.04-5.80 (m, 3 H), 5.36-5.04 (series of multiplets, 6 H), 4.14-3.94 (m, 4 H), 3.74 (td, J=13.8, 5.8 Hz, 2 H), 3.53 (bs, 1 H), 3.20-2.94 (m, 3 H), 3.31 (bs, 1 H), 2.38-1.90 (m, 4 H), 1.90-0.96 (series of multiplets, 20 H), 0.90 (d, J=5.4 Hz, 3 H), 0.89 (s, 3 H), 0.64 (s, 3 H); $^{13}$C NMR (CDCl$_3$, 50 MHz) δ 144.83, 136.27, 136.08, 128.94, 127.90, 126.98, 116.46, 115.70, 86.42, 80.94, 79.29, 74.98, 69.52, 69.39, 68.86, 64.39, 46.51, 46.42, 42.67, 42.14, 39.92, 35.63, 35.51, 35.13, 32.45, 28.98, 28.09, 27.66, 27.57, 26.72, 23.32, 23.11, 17.92, 12.69; HRFAB-MS (thioglycerol+Na$^+$ matrix) m/e: ([M+Na]$^+$) 779.5013 (86.1%); calcd. 779.5015.

Compound 16: To a three-necked round bottom flask was added 15 (3.34 g, 4.4 mmol) in CH$_2$Cl$_2$ (200 mL) and methanol (100 mL). Through the cold solution (−78° C.) ozone was bubbled through until a blue color persisted. Excess ozone was removed with oxygen flow. The mixture was left in a dry ice-acetone bath for an hour. Methyl sulfide (2.4 mL) was added and 15 minutes later, the mixture was treated with NaBH$_4$ (1.21 g, 32 mmol) in 5% aqueous NaOH solution (10 mL)/methanol (10 mL) and allowed to warm to room temperature. The mixture was washed with brine (3×50 mL), and the combined brine wash was extracted with CH$_2$Cl$_2$ (2×50 mL). The organic solution was dried over MgSO$_4$. After SiO$_2$ chromatography (MeOH (5%) in CH$_2$Cl$_2$), 3.30 g (95% yield) of 16 was isolated as an oil. IR (neat) 3358, 2934, 1448, 1070 cm$^{-1}$; $^1$H NMR (CDCl$_3$, 200 MHz) δ 7.50-7.42 (m, 6 H), 7.32-7.17 (m, 9 H), 3.80-2.96 (series of multiplets, 20 H), 2.25-0.96 (series of multiplets, 24 H), 0.89 (bs, 6 H), 0.65 (s, 3 H); $^{13}$C NMR (CDCl$_3$, 50 MHz) δ 144.73, 128.88, 127.87, 126.96, 86.38, 81.05, 79.75, 76.59, 70.33, 69.66, 69.30, 64.20, 62.25, 62.16, 62.03, 46.77, 46.36, 42.63, 41.77, 39.60, 35.43, 35.23, 35.05, 34.89, 32.42, 28.91, 27.93, 27.56, 27.15, 26.68, 23.35, 22.98, 22.85, 18.15, 12.60; HRFAB-MS (thioglycerol+Na$^+$ matrix) m/e: ([M+Na]$^+$) 791.4860 (100%), calcd. 791.4863.

Compound 17: To a round-bottom flask was added 16 (1.17 g, 1.55 mmol) in dry THF (30 mL) under N$_2$ in ice-bath followed by 9-BBN/THF solution (0.5 M, 10.2 mL, 5.51 mmol). The mixture was stirred at room temperature for 12 hours. Aqueous NaOH (20%) (2 mL) and hydrogen peroxide (30%) (2 mL) were added in sequence. The mixture was refluxed for 1 hour followed by the addition of brine (60 mL) and extraction with EtOAc (4×30 mL). The combined extracts were dried over anhydrous $Na_2SO_4$. The product (1.01 g, 80% yield) was obtained as a colorless oil after $SiO_2$ chromatography (5% MeOH in $CH_2Cl_2$). IR (neat) 3396, 2936, 1448, 1365, 1089 cm$^{-1}$; $^1$H NMR (CDCl$_3$, 200 MHz) δ 7.50-7.42 (m, 6 H), 7.34-7.16 (m, 9 H), 3.90-3.56 (m, 13 H), 3.50 (bs, 1 H), 3.40-2.96 (series of multiplets, 6 H), 2.30-0.94 (series of multiplets, 30 H), 0.90 (s, 3 H), 0.88 (d, J=5.4 Hz, 3 H), 0.64 (s, 3 H); $^{13}$C NMR (CDCl$_3$, 50 MHz) δ 144.73, 128.88, 127.85, 126.94, 86.36, 80.52, 78.90, 76.36, 66.82, 66.18, 65.77, 64.22, 61.53, 61.41, 61.34, 46.89, 46.04, 42.60, 41.59, 39.60, 35.37, 35.27, 34.88, 32.75, 32.44, 32.31, 28.82, 27.65, 27.48, 27.13, 26.77, 23.35, 22.74, 22.38, 18.08, 12.48; HRFAB-MS (thioglycerol+Na$^+$ matrix) m/e: ([M+Na]$^+$) 833.5331 (100%), calcd. 833.5332.

Compound 18: To a round-bottom flask were added 16 (3.30 g, 4.29 mmol) in $CH_2Cl_2$ (150 mL) and NEt$_3$ (2.09 mL, 15.01 mmol). The mixture was put in ice-bath under $N_2$ followed by addition of mesyl chloride (1.10 mL, 14.16 mmol). After 30 minutes, water (30 mL) and brine (200 mL) were added. The $CH_2Cl_2$ layer was washed with brine (2×50 mL) and dried over anhydrous $Na_2SO_4$. The combined aqueous mixture was extracted with EtOAc (3×100 mL). The combined extracts were washed with brine and dried over anhydrous $Na_2SO_4$. The desired product (3.35 g, 78% yield) was isolated as a pale yellow oil after $SiO_2$ chromatography (EtOAc/hexanes 1:1). IR (neat) 2937, 1448, 1352, 1174, 1120, 924 cm$^{-1}$; $^1$H NMR (CDCl$_3$, 200 MHz) δ 7.52-7.40 (m, 6 H), 7.34-7.20, (m, 9 H), 4.42-4.24 (m, 6 H), 3.90-3.64 (m, 4 H), 3.60-3.30 (m, 4 H), 3.24-3.00 (m, 3 H), 3.10 (s, 6 H), 3.05 (s, 3 H), 2.20-1.96 (m, 3 H) 1.96-1.60 (m, 8 H), 1.60-0.94 (series of multiplets, 13 H), 0.91 (bs, 6 H), 0.65 (s, 3 H); $^{13}$C NMR (CDCl$_3$, 50 MHz) δ 114.68, 128.85, 127.85, 126.96, 86.37, 81.37, 79.58, 76.58, 69.95, 69.43, 69.34, 66.52, 66.31, 65.59, 64.11, 46.80, 46.20, 42.65, 41.48, 39.35, 37.82, 37.48, 35.36, 34.92, 34.73, 32.37, 28.66, 28.01, 27.44, 27.03, 26.72, 23.17, 22.91, 22.72, 18.13, 12.50; HRFAB-MS (thioglycerol+Na$^+$ matrix) m/e: ([M+Na]$^+$) 1205.4176 (81.5%), calcd. 1205.4189.

Compound 19: To a round-bottom flask were added 17 (1.01 g, 1.25 mmol) in $CH_2Cl_2$ (50 mL) and NEt$_3$ (0.608 mL, 4.36 mmol). The mixture was put in ice-bath under $N_2$ followed by addition of mesyl chloride (0.318 mL, 4.11 mmol). After 30 minutes, water (10 mL) and then brine (80 mL) were added. The $CH_2Cl_2$ layer was washed with brine (2×20 mL) and dried over anhydrous $Na_2SO_4$. The combined aqueous mixture was extracted with EtOAc (3×40 mL). The combined extracts were washed with brine and dried over anhydrous $Na_2SO_4$. The desired product (1.07 g, 82%) was isolated as a pale yellowish oil after $SiO_2$ chromatography (EtOAc/hexanes 1:1). IR (neat) 2938, 1356, 1176, 1112 cm$^{-1}$; $^1$H NMR (CDCl$_3$, 300 MHz) δ 7.46-7.43, (m, 6 H), 7.32-7.22 (m, 9 H), 4.40-4.31 (m, 6 H), 3.72-3.64 (m, 2 H), 3.55 (dd, J=6.3, 5.8 Hz, 2 H), 3.51 (bs, 1 H), 3.32-3.14 (m, 3 H), 3.14-2.92 (m, 3 H), 3.01 (s, 3 H), 3.01 (s, 3 H), 3.00 (s, 3 H), 2.10-1.92 (m, 10 H), 1.92-1.58 (m, 8 H), 1.56-0.92 (series of multiplets, 12 H), 0.90 (s, 3 H), 0.89 (d, J=5.4 Hz, 3 H), 0.64 (s, 3 H); $^{13}$C NMR (CDCl$_3$, 75 MHz) δ 144.67, 128.85, 127.85, 126.96, 86.42, 81.06, 79.83, 76.81, 68.12, 68.06, 68.02, 64.26, 64.06, 63.42, 46.76, 46.38, 42.73, 41.87, 39.73, 37.44, 37.32, 37.29, 35.52, 35.48, 35.32, 35.06, 32.53, 30.55, 30.28, 30.02, 29.15, 27.96, 27.69, 27.61, 26.75, 23.52, 23.02, 18.17, 12.64; HRFAB-MS (thioglycerol+Na$^+$ matrix) m/e: ([M+Na]$^+$) 1067.4672 (100%), calcd. 1067.4659.

Compound 20: To a round-bottom flask were added 18 (1.50 g, 1.50 mmol) in dry DMSO (20 mL) and NaN$_3$ (0.976 g, 15 mmol). The mixture was heated to 80° C. and stirred under $N_2$ overnight then diluted with water (100 mL). The resulted aqueous mixture was extracted with EtOAc (3×50 mL), and the combined extracts washed with brine and dried over anhydrous $Na_2SO_4$. The desired product (0.83 g, 66% yield) was isolated as a clear glass after $SiO_2$ chromatography (EtOAc/hexanes 1:5). IR (neat) 2935, 2106, 1448, 1302, 1114 cm$^{-1}$; $^1$H NMR (CDCl$_3$, 200 MHz) δ 7.50-7.42 (m, 6 H), 7.36-7.20 (m, 9 H), 3.84-3.70 (m, 2 H), 3.65 (t, J=4.9 Hz, 2 H), 3.55 (bs, 1 H), 3.44-3.08 (m, 10 H), 3.02 (t, J=6.4 Hz, 2 H), 2.38-0.96 (series of multiplets, 24 H), 0.92 (d, J=5.6 Hz, 3 H), 0.91 (s, 3 H), 0.65 (s, 3 H); $^{13}$C NMR (CDCl$_3$, 50 MHz) δ 114.84, 128.97, 127.92, 126.99, 86.42, 81.24, 80.12, 76.59, 67.84, 67.29, 66.66, 64.36, 51.67, 51.44, 51.18, 46.53, 46.23, 42.21, 41.93, 39.73, 35.66, 35.36, 35.06, 34.78, 32.40, 28.95, 27.76, 27.39, 26.87, 23.45, 22.98, 22.92, 17.98, 12.53; HRFAB-MS (thioglycerol+Na$^+$ matrix) m/e: ([M+Na]$^+$) 866.5040 (100%), calcd. 866.5057.

Compound 22: To a round-bottom flask were added 20 (830 mg, 0.984 mmol) in MeOH (30 mL) and $CH_2Cl_2$ (30 mL) and p-toluenesulfonic acid (9.35 mg, 0.0492 mmol). The solution was stirred at room temperature for 2.5 hours then saturated aqueous NaHCO$_3$ (10 mL) was introduced. Brine (30 mL) was added, and the mixture was extracted with EtOAc (4×20 mL). The combined extracts were dried over anhydrous $Na_2SO_4$. The desired product (0.564 g, 95% yield) was isolated as a pale yellowish oil after $SiO_2$ chromatography (EtOAc/hexanes 1:2). IR (neat) 3410, 2934, 2106, 1301, 1112 cm$^{-1}$; $^1$H NMR (CDCl$_3$, 200 MHz) δ 3.80-3.54 (m, 7 H), 3.44-3.20 (m, 10 H), 2.35-0.96 (series of multiplets, 24 H), 0.95 (d, J=6.4 Hz, 3 H), 0.92 (s, 3 H), 0.68 (s, 3 H); $^{13}$C NMR (CDCl$_3$, 50 MHz) δ 81.10, 80.01, 76.60, 67.75, 67.16, 66.56, 63.63, 51.57, 51.34, 51.06, 46.29, 46.12, 42.12, 41.81, 39.60, 35.55, 35.23, 34.94, 34.66, 31.75, 29.48, 28.81, 27.72, 27.66, 27.29, 23.32, 22.86, 22.80, 17.85, 12.39; HRFAB-MS (thioglycerol+Na$^+$ matrix) m/e: ([M+Na]$^+$) 624.3965 (100%), calcd. 624.3962.

Compound 23: To a round-bottom flask were added 19 (1.07 g, 1.025 mmol) and NaN$_3$ (0.666 g, 10.25 mmol) followed the introduction of dry DMSO (15 mL). The mixture was heated up to 80° C. under $N_2$ overnight. After the addition of $H_2O$ (100 mL), the mixture was extracted with EtOAc (4×40 mL) and the combined extracts were washed with brine (2×50 mL) and dried over anhydrous $Na_2SO_4$. After removal of solvent, the residue was dissolved in MeOH (15 mL) and $CH_2Cl_2$ (15 mL) followed by the addition of catalytic amount of p-toluenesulfonic acid (9.75 mg, 0.051 mmol). The solution was stirred at room temperature for 2.5 hours before the addition of saturated NaHCO$_3$ solution (15 mL). After the addition of brine (60 mL), the mixture was extracted with EtOAc (5×30 mL). The combined extracts were washed with brine (50 mL) and dried over anhydrous $Na_2SO_4$. The desired product (0.617 g, 94% yield for two steps) was obtained as a yellowish oil after $SiO_2$ chromatography (EtOAc/hexanes 1:2). IR (neat) 3426, 2928, 2094, 1456, 1263, 1107 cm$^{-1}$; $^1$H NMR (CDCl$_3$, 300 MHz) δ 3.68-3.56 (m, 3 H), 3.56-3.34 (series of multiplets, 10 H), 3.28-3.00 (series of multiplets, 4 H), 2.20-2.00 (m, 3 H), 1.98-1.55 (series of multiplets, 15 H), 1.55-0.96 (series of multiplets, 13 H), 0.92 (d, J=6.6 Hz, 3 H), 0.89 (s, 3 H), 0.66 (s, 3 H); $^{13}$C NMR (CDCl$_3$, 75 MHz) δ 80.63, 79.79, 76.04, 64.99, 64.45, 64.30, 63.72, 49.01, 48.94, 48.74, 46.49, 46.39, 42.70, 41.98, 39.80, 35.65, 35.42, 35.28, 35.08, 31.99, 29.78, 29.75, 29.70, 29.49, 29.06, 27.87, 27.79, 27.65, 23.53, 23.04, 22.85, 18.05, 12.59; HRFAB-MS (thioglycerol+Na matrix) m/e: ([M+Na]$^+$) 666.4415 (100%), calcd. 666.4431.

Compound 24: To a round-bottom flask were added 22 (0.564 g, 0.938 mmol) in CH$_2$Cl$_2$ (30 mL) and NEt$_3$ (0.20 mL, 1.40 mmol). The mixture was put in ice-bath under N$_2$ followed by addition of mesyl chloride (0.087 mL, 1.13 mmol). After 30 minutes, water (20 mL) and brine (100 mL) were added. The CH$_2$Cl$_2$ layer was washed with brine (2×20 mL) and dried over anhydrous Na$_2$SO$_4$. The combined aqueous mixture was extracted with EtOAc (3×30 mL). The combined extracts were washed with brine and dried over anhydrous Na$_2$SO$_4$. The desired product (0.634 g, 99% yield) was isolated as a pale yellowish oil after SiO$_2$ chromatography (EtOAc/hexanes 1:2). IR (neat) 2935, 2106, 1356, 1175, 1113 cm$^{-1}$; $^1$H NMR (CDCl$_3$, 300 MHz) δ 4.20 (t, J=6.8 Hz, 2 H), 3.80-3.75 (m, 1 H), 3.70-3.64 (m, 3 H), 3.55 (bs, 1 H), 3.44-3.01 (m, 10 H), 3.00 (s, 3 H), 2.32-2.17 (m, 3 H), 2.06-2.03 (m, 1 H), 1.90-0.88 (series of multiplets, 20 H), 0.95 (d, J=6.6 Hz, 3 H), 0.91 (s, 3 H), 0.68 (s, 3 H); $^{13}$C NMR (CDCl$_3$, 75 MHz) δ 80.90, 79.86, 76.43, 70.78, 67.64, 66.99, 66.48, 51.50, 51.26, 50.97, 46.05, 45.96, 42.08, 41.71, 39.51, 37.33, 35.15, 34.86, 34.60, 31.34, 28.73, 27.62, 27.59, 27.51, 25.68, 23.22, 22.80, 22.70, 17.62, 12.33; HRFAB-MS (thioglycerol+Na$^+$ matrix) m/e: ([M+Na]$^+$) 702.3741 (100%), calcd. 702.3737.

Compound 25: To a round-bottom flask were added 23 (0.617 g, 0.96 mmol) in CH$_2$Cl$_2$ (30 mL) and NEt$_3$ (0.20 mL, 1.44 mmol). The mixture was put in ice-bath under N$_2$ followed by addition of mesyl chloride (0.089 mL, 1.15 mmol). After 30 minutes, water (20 mL) and brine (120 mL) were added. The CH$_2$Cl$_2$ layer was washed with brine (2×20 mL) and dried over anhydrous Na$_2$SO$_4$. The combined aqueous mixture was extracted with EtOAc (3×30 mL). The combined extracts were washed with brine and dried over anhydrous Na$_2$SO$_4$. The desired product (0.676 g, 97% yield) was isolated as a pale yellowish oil after removal of solvent. IR (neat) 2934, 2094, 1454, 1360, 1174, 1112 cm$^{-1}$; $^1$H NMR (CDCl$_3$, 300 MHz) δ 4.17 (t, J=6.6 Hz, 2 H), 3.65-3.28 (series of multiplets, 11 H), 3.64-3.00 (series of multiplets, 4 H), 2.97 (s, 3 H), 2.18-1.96 (series of multiplets, 16 H), 1.54-0.94 (series of multiplets, 11 H), 0.89 (d, J=6.6 Hz, 3 H), 0.86 (s, 3 H), 0.63 (s, 3 H); $^{13}$C NMR (CDCl$_3$, 75 MHz) δ 80.87, 79.67, 75.92, 70.84, 64.90, 64.37, 64.17, 48.90, 48.86, 48.66, 46.32, 46.26, 42.63, 41.87, 39.70, 37.39, 35.34, 35.28, 35.20, 34.99, 31.61, 29.68, 29.60, 28.96, 27.78, 27.68, 27.57, 25.79, 23.41, 22.95, 22.74, 17.82, 12.50; HRFAB-MS (thioglycerol matrix) m/e: ([M+H]$^+$) 722.4385 (22.1%), calcd. 722.4387.

Compound 26: To a 50 mL round-bottom flask was added 24 (0.634 g, 0.936 mmol) and N-benzylmethylamine (2 mL). The mixture was heated under N$_2$ at 80° C. overnight. Excess N-benzylmethylamine was removed under vacuum, and the residue was subjected to SiO$_2$ chromatography (EtOAc/hexanes 1:2). The desired product (0.6236 g, 95% yield) was isolated as a pale yellow oil. IR (neat) 2935, 2106, 1452, 1302, 1116 cm$^{-1}$; $^1$H NMR (CDCl$_3$, 200 MHz) δ 7.32-7.24 (m, 5 H), 3.80-3.76 (m, 1 H), 3.70-3.60 (m, 3 H), 3.54 (bs, 1 H), 3.47 (s, 2 H), 3.42-3.10 (m, 10 H), 2.38-2.05 (m, 5 H), 2.17 (s, 3 H), 2.02-0.88 (series of multiplet, 21 H), 0.93 (d, J=7.0 Hz, 3 H), 0.91 (s, 3 H), 0.66 (s, 3 H); $^{13}$C NMR (CDCl$_3$, 50 MHz) δ 139.60, 129.34, 128.38, 127.02, 81.22, 80.10, 76.71, 67.85, 67.29, 66.65, 62.45, 58.38, 51.65, 51.44, 51.16, 46.50, 46.21, 42.40, 42.20, 41.93, 39.72, 35.80, 35.34, 35.05, 34.76, 33.65, 28.93, 27082, 27.75, 27.38, 24.10, 23.45, 22.98, 22.91, 18.05, 12.50; HRFAB-MS (thioglycerol+Na$^+$ matrix) m/e: ([M−H]$^+$) 703.4748 (90.2%), calcd. 703.4772; ([M+H]$^+$) 705.4911 (100%), calcd. 705.4928; ([M+Na]$^+$) 727.4767 (1.5%), calcd. 727.4748.

Compound 27: To a 50 mL round-bottom flask was added 25 (0.676 g, 0.937 mmol) and N-benzylmethylamine (2 mL). The mixture was heated under N$_2$ at 80° C. overnight. Excess N-benzylmethylamine was removed under vacuum and the residue was subjected to SiO$_2$ chromatography (EtOAc/hexanes 1:2). The desired product (0.672 g, 96% yield) was isolated as a pale yellow oil. IR (neat) 2934, 2096, 1452, 1283, 1107 cm$^{-1}$; $^1$H NMR (CDCl$_3$, 300 MHz) δ 7.34-7.20 (m, 5 H), 3.68-3.37 (series of multiplets, 13 H), 3.28-3.04 (m, 4 H), 2.33 (t, J=7.0 Hz, 2 H), 2.18 (s, 3 H), 2.20-2.00 (m, 3 H), 1.96-1.56 (series of multiplets, 14 H), 1.54-1.12 (m, 10 H), 1.10-0.96 (m, 3 H), 0.91 (d, J=8.7 Hz, 3 H), 0.89 (s, 3 H), 0.65 (s, 3 H); $^{13}$C NMR (CDCl$_3$, 75 MHz) δ 139.48, 129.23, 128.30, 126.96, 80.66, 79.81, 76.08, 65.00, 64.46, 64.34, 62.50, 58.37, 49.02, 48.95, 48.75, 46.65, 46.40, 42.69, 42.43, 42.00, 39.83, 35.86, 35.45, 35.30, 35.10, 33.83, 29.81, 29.78, 29.72, 29.09, 27.88, 27.81, 27.66, 24.19, 23.57, 23.06, 22.87, 18.15, 12.62; HRFAB-MS (thioglycerol matrix) m/e: ([M+H]$^+$) 747.5406 (77.2%), calcd. 747.5398.

Compound 1: To a round-bottom flask were added 26 (0.684 g, 0.971 mmol) in dry THF (30 mL) and LiAlH$_4$ (113.7 mg, 3.0 mmol) under N$_2$. The mixture was stirred at room temperature for 12 hours, and then Na$_2$SO$_4$.10 H$_2$O powder (10 g) was added slowly. After the grey color disappeared, the mixture was filtered through Celite and washed with dry THF. The product (0.581 g, 95% yield) was obtained as a colorless glass. IR (neat) 3372, 2937, 1558, 1455, 1362, 1102 cm$^{-1}$; $^1$H NMR (CDCl$_3$, 300 MHz) δ 7.34-7.20 (m, 5 H), 3.68-3.48 (m, 5 H), 3.47 (s, 2 H), 3.29 (bs, 1 H), 3.22-3.00 (m, 3 H), 2.96-2.80 (m, 6 H), 2.32 (t, J=6.8, 5.4 Hz, 2 H), 2.17 (s, 3 H), 2.20-2.00 (m, 3 H), 1.96-0.96 (series of multiplets, 27 11), 0.93 (d, J=6.8 Hz, 3 H), 0.90, (s, 3 H), 0.67 (s, 3 H); $^{13}$C NMR (CDCl$_3$, 75 MHz) δ 139.50, 129.22, 128.31, 126.96, 80.76, 79.85, 76.10, 70.90, 70.33, 70.24, 62.48, 58.27, 46.55, 46.45, 42.72, 42.58, 42.33, 41.99, 39.77, 35.78, 35.37, 35.01, 33.73, 29.07, 27.95, 27.71, 24.06, 23.46, 22.99, 18.14, 12.55; HRFAB-MS (thioglycerol matrix) m/e: ([M+H]$^+$) 627.5211 (100%), calcd. 627.5213.

HCl salt of compound 1: Compound 1 was dissolved in a minimum amount of CH$_2$Cl$_2$ and excess HCl in ether was added. Solvent and excess HCl were removed in vacuo and a noncrystalline white powder was obtained. $^1$H NMR (methanol-d4/15% (CDCl$_3$, 300 MHz) δ 7.61-7.57 (m, 2 H), 7.50-7.48 (m, 3 H), 4.84 (bs, 10 H), 4.45 (bs, 1 H), 4.30 (bs, 1 H), 3.96-3.82 (m, 2 H), 3.78-3.69 (m, 2 H), 3.66 (bs, 1 H), 3.59-3.32 (series of multiplets, 4 H), 3.28-3.02 (m, 8 H), 2.81 (s, 3 H), 2.36-2.15 (m, 4 H), 2.02-1.68 (m, 8 H), 1.64-0.90 (series of multiplets, 12 H), 1.01 (d, J=6.35 Hz, 3 H), 0.96 (s, 3 H), 0.73 (s, 3 H); $^{13}$C NMR (methanol-d4/15% (CDCl$_3$, 75 MHz) δ 132.31, 131.20, 130.92, 130.40, 83.13, 81.09, 78.48, 65.54, 64.98, 64.11, 60.87, 57.66, 47.51, 46.91, 43.52, 43.00, 41.38, 41.19, 41.16, 40.75, 40.30, 36.37, 36.08, 36.00, 35.96, 33.77, 29.68, 29.34, 28.65, 28.37, 24.42, 24.25, 23.33, 21.51, 18.80, 13.04.

Compound 2: To a round-bottom flask were added 27 (0.82 g, 1.10 mmol) in dry THF (150 mL) and LiAlH$_4$ (125 mg, 3.30 mmol) under N$_2$. The mixture was stirred at room temperature for 12 hours and Na$_2$SO$_4$.10 H$_2$O powder (10 g) was added slowly. After the grey color disappeared, the mixture was filtered through a cotton plug and washed with dry THF. THF was removed in vacua and the residue dissolved in CH$_2$Cl$_2$ (50 mL). After filtration, the desired product was obtained as a colorless glass (0.73 g, 99% yield). IR (neat) 3362, 2936, 2862, 2786, 1576, 1466, 1363, 1103 cm$^{-1}$; $^1$H NMR (CDCl$_3$, 300 MHz) δ 7.32-7.23 (m, 5 H), 3.67-3.63 (m, 1 H), 3.60-3.57 (m, 1 H), 3.53 (t, J=6.4 Hz, 2 H), 3.47 (s, 2 H), 3.46 (bs, 1 H), 3.24-3.17(m, 2 H), 3.12-2.99 (m, 2 H), 2.83-2.74 (series of multiplets, 6 H), 2.30 (t, J=7.3 Hz, 2 H), 2.15 (s, 3 H), 2.20-2.00 (m, 3 H), 1.95-1.51 (series of multiplets, 20 H), 1.51-1.08, (series of multiplets, 10 H), 1.06-0.80 (m, 3H), 0.87 (d, J=8.1 Hz, 3 H), 0.86 (s, 3 H), 0.61 (s, 3 H); $^{13}$C NMR (CDCl$_3$, 75 MHz). 139.35, 129.16, 128.22, 126.88, 80.44, 79.29, 75.96, 66.70, 66.52, 66.12, 62.45, 58.26, 46.76, 46.27, 42.69, 42.41, 42.02, 40.68, 40.10, 40.02, 39.82, 35.84, 35.47, 35.30, 35.06, 34.15, 34.09, 34.03, 33.80, 28.96, 27.93, 27.75, 27.71, 24.32, 23.53, 23.03, 22.75, 18.17, 12.58; HRFAB-MS (thioglycerol+Na$^+$ matrix) m/e: ([M+Na]$^+$) 691.5504 (38.5%), calcd. 691.5502.

HCl salt of compound 2: Compound 2 was dissolved in a minimum amount of CH$_2$Cl$_2$ and excess HCl in ether was added. Removal of the solvent and excess HCl gave a noncrystalline white powder. $^1$H NMR (methanol-d$_4$/15% CDCl$_3$, 300 MHz) δ 7.60-7.59 (m, 2 H), 7.50-7.47 (m, 3 H), 4.82 (bs, 10 H), 4.43 (bs, 1 H), 4.32 (bs, 1 H), 3.85-3.79 (m, 1 H), 3.75-3.68 (m, 1 H), 3.64 (t, J=5.74 Hz, 2 H), 3.57 (bs, 1 H), 3.36-3.28 (m, 2 H), 3.25-3.00 (series of multiplets, 10 H), 2.82 (s, 3 H), 2.14-1.68 (series of multiplets, 19 H), 1.65-1.15 (series of multiplets, 11 H), 0.98 (d, J=6.6 Hz, 3 H), 0.95 (s, 3 H), 0.72 (s, 3 H); $^{13}$C NMR (methanol-d$_4$/15% CDCl$_3$, 75 MHz) δ 132.21, 131.10, 130.58, 130.28, 81.96, 80.72, 77.60, 66.84, 66.58, 66.12, 61.03, 57.60, 44.16, 42.77, 40.62, 39.57, 39.43, 36.28, 36.03, 35.96, 35.78, 33.65, 29.48, 29.27, 29.11, 29.01, 28.61, 28.56, 28.35, 24.25, 23.56, 23.30, 21.17, 18.64, 12.90.

Compound 4: A suspension of 1 (79.1 mg, 0.126 mmol) and aminoiminomethanesulfonic acid (50.15 mg, 0.404 mmol) in methanol and chloroform was stirred at room temperature for 24 hours, and the suspension became clear. An ether solution of HCl (1 M, 1 mL) was added followed by the removal of solvent with N$_2$ flow. The residue was dissolved in H$_2$O (5 mL) followed by the addition of 20% aqueous NaOH (0.5 mL). The resulting cloudy mixture was extracted with CH$_2$Cl$_2$ (4×5 mL). The combined extracts were dried over anhydrous Na$_2$SO$_4$. Removal of solvent gave the desired product (90 mg, 95%) as white powder. m.p. 111-112° C. IR (neat) 3316, 2937, 1667, 1650, 1556, 1454, 1348, 1102 cm$^{-1}$; $^1$H NMR (5% methanol-d4/CDCl$_3$, 300 MHz) δ 7.26-7.22 (m, 5 H), 4.37 (bs, 3 H), 3.71-3.51 (series of multiplets, 5 H), 3.44 (s, 2 H), 3.39-3.10 (series of multiplets, 10 H), 2.27 (t, J=6.83 Hz, 2 H), 2.13 (s, 3 H), 2.02-0.94 (series of multiplets, 33 H), 0.85 (d, J=5.62 Hz, 3 H), 0.84 (s, 3 H), 0.61 (s, 3 H); $^{13}$C NMR (5% methanol-d4/CDCl$_3$, 75 MHz) δ 158.54, 158.48, 158.43, 138.27, 129.47, 128.32, 127.19, 81.89, 80.30, 77.34, 69.02, 68.46, 67.21, 62.36, 58.00, 47.36, 46.18, 43.26, 43.00, 42.73, 42.18, 41.48, 39.32, 35.55, 34.97, 34.89, 34.67, 33.63, 28.93, 28.28, 27.53, 27.16, 23.96, 23.28, 23.16, 22.77, 18.36, 12.58; HRFAB-MS (thioglycerol+Na$^+$ matrix) m/e: ([M+H]$^+$) 753.5858 (100%), calcd. 753.5867.

HCl salt of compound 4: Compound 4 was dissolved in minimum amount of CH$_2$Cl$_2$ and MeOH followed by addition of excess HCl in ether. The solvent was removed by N$_2$ flow, and the residue was subjected to high vacuum overnight. The desired product was obtained as noncrystalline white powder. $^1$H NMR (methanol-d4/20% (CDCl$_3$, 300 MHz) δ 7.58 (bs, 2 H), 7.50-7.48 (m, 3 H), 4.76 (bs, 13 H), 4.45 (d, J=12.9 Hz, 1 H), 4.27 (dd, 1 H, J=12.9, 5.4 Hz), 3.82-3.00 (series of multiplets, 17 H), 2.81-2.80 (m, 3 H), 2.20-1.02 (series of multiplets, 27 H), 0.98 (d, J=6.59 Hz, 3 H), 0.95 (s, 3 H), 0.72 (s, 3 H); $^{13}$C NMR (methanol-d4/20% CDCl$_3$, 75 MHz) δ 158.88, 158.72, 132.00, 131.96, 130.98, 130.15, 82.51, 81.07, 78.05, 68.50, 68.02, 67.94, 67.10, 60.87, 60.53, 57.38, 47.16, 46.91, 43.91, 43.11, 43.01, 42.91, 42.55, 40.28, 39.88, 39.95, 35.90, 35.73, 35.64, 33.53, 29.18, 28.35, 27.99, 24.02, 23.30, 21.35, 18.52, 18.44, 13.06.

Compound 5: A suspension of 2 (113 mg, 0.169 mmol) and aminoiminomethanesulfonic acid (67.1 mg, 0.541 mmol) in methanol and chloroform was stirred at room temperature for 24 hours. HCl in ether (1 M, 1 mL) was added followed by the removal of solvent with N$_2$ flow. The residue was subject to high vacuum overnight and dissolved in H$_2$O (5 mL) followed by the addition of 20% NaOH solution (1.0 mL). The resulting mixture was extracted with CH$_2$Cl$_2$ (5×5 mL). The combined extracts were dried over anhydrous Na$_2$SO$_4$. Removal of solvent gave desired the product (90 mg, 95% yield) as a white solid. m.p. 102-104° C. IR (neat) 3332, 3155, 2939, 2863, 1667, 1651, 1558, 1456, 1350, 1100 cm$^{-1}$; $^1$H NMR (5% methanol-d4/CDCl$_3$, 300 MHz) δ 7.35-7.24 (m, 5 H), 3.75-3.64 (m, 1 H), 3.57 (bs, 5 H), 3.50 (s, 2 H), 3.53-3.46 (m, 1 H), 3.40-3.10 (series of multiplets, 14 H), 2.34 (t, J=7.31 Hz, 2 H), 2.19 (s, 3 H), 2.13-0.96 (series of multiplets, 36 H), 0.91 (bs, 6 H), 0.66 (s, 3 H); $^{13}$C NMR (5% methanol-d4/CDCl$_3$, 75 MHz) δ 157.49, 157.31, 157.23, 138.20, 129.52, 128.34, 127.23, 81.17, 79.19, 76.42, 65.63, 65.03, 64.70, 62.36, 58.02, 47.23, 46.24, 42.89, 42.18, 41.45, 39.45, 39.40, 39.30, 38.71, 35.61, 35.55, 35.02, 34.82, 33.69, 29.87, 29.59, 29.42, 28.84, 27.96, 27.56, 23.95, 23.40, 22.82, 22.64, 18.28, 12.54; HRFAB-MS (thioglycerol+Na$^+$ matrix) m/e: ([M+H]$^+$) 795.6356 (84.3%), calcd. 795.6337.

HCl salt of compound 5: Compound 5 was dissolved in minimum amount of CH$_2$Cl$_2$ and MeOH followed by the addition of excess HCl in ether. The solvent and excess HCl were removed by N$_2$ flow and the residue was subject to high vacuum overnight. The desired product was obtained as noncrystalline white powder. $^1$H NMR (methanol-d4/10% CDCl$_3$, 300 MHz) δ 7.62-7.54 (m, 2 H), 7.48-7.44 (m, 3 H), 4.84 (bs, 16 H), 4.46 (d, J=12.7 Hz, 1 H), 4.26 (dd, J=12.7, 3.42 Hz, 1 H), 3.78-3.56 (series of multiplets, 5 H), 3.38-3.05 (series of multiplets, 13 H), 2.80 (d, 3 H), 2.19-2.04 (m, 3 H), 2.02-1.04 (series of multiplets, 30 H), 0.98 (d, J=6.35 Hz, 3 H), 0.95 (s, 3 H), 0.72 (s, 3 H); $^{13}$C NMR (methanol-d4/10% CDCl$_3$, 75 MHz) δ 158.75, 158.67, 132.32, 131.24, 130.83, 130.43, 82.49, 81.02, 77.60, 66.47, 65.93, 61.19, 60.85, 57.69, 47.79, 47.60, 44.29, 43.07, 40.86, 40.42, 40.19, 40.09, 39.76, 36.68, 36.50, 36.15, 35.94, 33.91, 30.75, 30.46, 29.74, 29.33, 28.71, 24.41, 24.03, 23.38, 22.21, 22.16, 18.59, 18.52, 13.09.

Compound CSA-26 was synthesized according to Scheme 1 and Example 1 using 7-deoxycholic acid in place of cholic acid and methyl cholate.

Example 2

This example includes a description of one or more exemplary synthestic procedures for obtaining Compounds 3, 28 and 29.

Compound 28: A suspension of 19 (0.641 g, 0.614 mmol) and KCN (0.40 g, 6.14 mmol) in anhydrous DMSO (5 mL) was stirred under N$_2$ at 80° C. overnight followed by the addition of H$_2$O (50 mL). The aqueous mixture was extracted with EtOAc (4×20 mL). The combined extracts were washed with brine once, dried over anhydrous Na$_2$SO$_4$ and concentrated in vacuo. The residue was dissolved in CH$_2$Cl$_2$ (3 mL) and MeOH (3 mL) and catalytic amount of p-toluenesulfonic acid (5.84 mg, 0.03 mmol) was added. The solution was stirred at room temperature for 3 hours before the introduction of saturated NaHCO$_3$ solution (10 mL). After the addition of brine (60 mL), the mixture was extracted with EtOAc (4×30 mL). The combined extracts were washed with brine once and dried over anhydrous Na$_2$SO$_4$ and concentrated. The residue afforded the desired product (0.342 g, 92% yield) as pale yellowish oil after column chromatography (silica gel, EtOAc/hexanes 2:1). IR (neat) 3479, 2936, 2864, 2249, 1456, 1445, 1366, 1348, 1108 cm$^{-1}$; $^1$H NMR (CDCl$_3$, 300 MHz) δ 3.76-3.53 (m, 7 H), 3.32-3.06 (series of multiplets, 4 H), 2.57-2.46 (m, 6 H), 2.13-1.00 (series of multiplets, 31 H), 0.93 (d, J=6.35 Hz, 3 H), 0.90 (s, 3 H), 0.67 (s, 3 H); $^{13}$C NMR (CDCl$_3$, 75 MHz) δ 119.91, 119.89, 80.75, 79.65, 76.29, 65.83, 65.37, 65.19, 63.63, 46.57, 46.44, 42.77, 41.79, 39.71, 35.63, 35.26, 35.02, 32.00, 29.46, 29.03, 27.96, 27.74, 26.64, 26.42, 26.12, 23.56, 22.98, 22.95, 18.24, 14.65, 14.54, 14.30, 12.60; HRFAB-MS (thioglycerol+Na$^+$ matrix) m/e: ([M+Na]$^+$) 618.4247 (67.8%), calcd. 618.4247.

Compound 29: To a solution of 28 (0.34 g, 0.57 mmol) in dry CH$_2$Cl$_2$ (15 mL) under N$_2$ at 0° C. was added NEt$_3$ (119.5 µL, 0.857 mmol) followed by the addition of mesyl chloride (53.1 .mu.L, 0.686 mmol). The mixture was allowed to stir at 0° C. for 30 minutes before the addition of H$_2$O (6 mL). After the introduction of brine (60 mL), the aqueous mixture was extracted with EtOAc (4×20 mL). The combined extracts were washed with brine once, dried over anhydrous Na$_2$SO$_4$ and concentrated. To the residue was added N-benzylmethyl amine (0.5 mL) and the mixture was stirred under N$_2$ at 80° C. overnight. Excess N-benzylmethylamine was removed in vacuo and the residue was subject to column chromatography (silica gel, EtOAc/hexanes 2:1 followed by EtOAc) to afford product (0.35 g, 88% yield) as a pale yellow oil. IR (neat) 2940, 2863, 2785, 2249, 1469, 1453, 1366, 1348, 1108 cm$^{-1}$; $^1$H NMR (CDCl$_3$, 300 MHz) δ 7.34-7.21 (m, 5 H), 3.76-3.69 (m, 1 H), 3.64-3.50 (m, 4 H), 3.48 (s, 2 H), 3.31-3.05 (series of multiplets, 4 H), 2.52-2.46 (m, 6 H), 2.33 (t, J=7.32 H, 2 Hz), 2.18 (s, 3 H), 2.13-0.95 (series of multiplets, 30 H), 0.91 (d, J=6.80 H, 3 Hz), 0.90 (s, 3 H), 0.66 (s, 3 H); $^{13}$C NMR (CDCl$_3$, 75 MHz) δ 139.37, 129.17, 128.26, 126.93, 119.96, 119.91, 80.73, 79.59, 76.26, 65.79, 65.35, 65.13, 62.47, 58.25, 46.74, 46.40, 42.72, 42.38, 41.76, 39.68, 35.78, 35.22, 34.98, 33.79, 28.99, 27.92, 27.71, 26.63, 26.38, 26.09, 24.21, 23.54, 22.96, 22.90, 18.28, 14.62, 14.51, 14.26, 12.58; HRFAB-MS (thioglycerol+Na$^+$ matrix) m/e: ([M+H]$^+$) 699.5226 (100%), calcd. 699.5213.

Compound 3: A solution of 29 (0.074 g, 0.106 mmol) in anhydrous THF (10 mL) was added dropwise to a mixture of AlCl$_3$ (0.1414 g, 1.06 mmol) and LiAlH$_4$ (0.041 g, 1.06 mmol) in dry THF (10 mL): The suspension was stirred for 24 hours followed by the addition of 20% NaOH aqueous solution (2 mL) at ice-bath temperature. Anhydrous Na$_2$SO$_4$ was added to the aqueous slurry. The solution was filtered and the precipitate washed twice with THF. After removal of solvent, the residue was subject to column chromatography (silica gel, MeOH/CH$_2$Cl$_2$ 1:1 followed by MeOH/CH$_2$Cl$_2$/NH$_3$.H$_2$O 4:4:1) to afford the desired product (0.038 g, 50% yield) as a clear oil. IR (neat) 3362, 2935, 2863, 2782, 1651, 1574, 1568, 1557, 1471, 1455, 1103 cm$^{-1}$; $^1$H NMR (CDCl$_3$, 300 MHz) δ 7.32-7.22 (m, 5 H), 3.60-3.02 (series of broad multiplets, 18 H), 2.90-2.70 (m, 5 H), 2.33 (t, J=7.20 Hz, 2 H), 2.24-2.04 (m, 3 H), 2.18 (s, 3 H), 1.96-0.96 (series of multiplets, 30 H), 0.90 (d, J=7.57 Hz, 3 H), 0.89 (s, 3 H), 0.64 (s, 3 H); $^{13}$C NMR (CDCl$_3$, 75 MHz) δ 139.44, 129.24, 128.31, 126.97, 80.63, 79.65, 75.97, 68.44, 68.00, 67.96, 62.54, 58.40, 46.77, 46.30, 42.73, 42.43, 42.07, 41.92, 41.74, 41.72, 39.81, 35.82, 35.48, 35.07, 33.84, 31.04, 30.30, 30.10, 29.03, 28.11, 27.82, 27.81, 27.74, 27.67, 27.64, 24.31, 23.50, 23.04, 22.93, 18.22, 12.63; HRFAB-MS (thioglycerol+Na$^+$ matrix) m/e: ([M+H]$^+$) 711.6139 (100%), calcd. 711.6152; ([M+Na]$^+$) 733.5974 (46.1%), calcd. 733.5972.

Example 3

This example includes a description of one or more exemplary synthestic procedures for obtaining Compounds 6, 7 and 30-33.

Compound 30: Cholic acid (3.0 g, 7.3 mmol) was dissolved in CH$_2$Cl$_2$ (50 mL) and methanol (5 mL). Dicyclohexylcarbodiimide (DCC) (1.8 g, 8.8 mmol) was added followed by N-hydroxysuccinimide (about 100 mg) and benzylmethylamine (1.1 g, 8.8 mmol). The mixture was stirred for 2 hours, then filtered. The filtrate was concentrated and chromatographed (SiO$_2$, 3% MeOH in CH$_2$Cl$_2$) to give 3.0 g of a white solid (81% yield). m.p. 184-186° C.; IR (neat) 3325, 2984, 1678 cm$^{-1}$; $^1$H NMR (CDCl$_3$, 200 MHz) δ 7.21 (m, 5 H), 4.51 (m, 2 H), 3.87 (m, 1 H), 3.74 (m, 2 H), 3.36 (m, 2 H), 2.84 (s, 3 H), 2.48-0.92 (series of multiplets, 28 H), 0.80 (s, 3 H), 0.58 (d, J=6.5 Hz, 3 H); $^{13}$C NMR (CDCl$_3$, 50 MHz) δ 174.30, 173.94, 137.36, 136.63, 128.81, 128.46, 127.85, 127.50, 127.18, 126.28, 72.96, 71.76, 68.35, 53.39, 50.65, 48.77, 46.91, 46.33, 41.44, 39.36, 39.18, 35.76, 35.27, 34.76, 33.87, 31.54, 34.19, 31.07, 30.45, 28.11, 27.63, 26.14, 25.59, 24.92, 23.26, 17.51, 12.41; FAB-MS (thioglycerol+Na$^+$ matrix) m/e: ([M+H]$^+$) 512 (100%), calcd. 512.

Compound 31: Compound 30 (2.4 g, 4.7 mmol) was added to a suspension of LiAlH$_4$ (0.18 g, 4.7 mmol) in THF (50 mL). The mixture was refluxed for 24 hours, then cooled to 0° C. An aqueous solution of Na$_2$SO$_4$ was carefully added until the grey color of the mixture dissipated. The salts were filtered out, and the filtrate was concentrated in vacuo to yield 2.1 g of a white solid (88%). The product proved to be of sufficient purity for further reactions. m.p. 70-73° C.; IR (neat) 3380, 2983, 1502 cm$^{-1}$; $^1$H NMR (CDCl$_3$, 300 MHz) δ 7.23 (m, 5 H), 3.98 (bs, 2 H), 3.81 (m, 3 H), 3.43 (m, 3H), 2.74 (m, 2 H), 2.33 (m, 3 H), 2.25 (s, 3 H), 2.10-0.90 (series of multiplets, 24 H), 0.98 (s, 3 H), 0.78 (s, 3 H); $^{13}$C NMR (CDCl$_3$, 75 MHz) δ 135.72, 129.63, 128.21, 128.13, 125.28, 72.91, 71.63, 62.05, 60.80, 56.79, 47.00, 46.23, 41.44, 40.81, 39.41, 35.42, 35.24, 34.63, 34.02, 33.22, 31.73, 30.17, 29.33, 29.16, 28.02, 27.49, 26.17, 25.55, 23.10, 22.48, 22.33, 17.54, 12.65; FAB-MS (thioglycerol matrix) m/e: ([M+H]$^+$) 498 (100%), calcd. 498.

Compound 32: Compound 31 (0.36 g, 0.72 mmol) was dissolved in CH$_2$Cl$_2$ (15 mL) and Bocglycine (0.51 g, 2.89 mmol), DCC (0.67 g, 3.24 mmol) and dimethylaminopyridine (DMAP) (about 100 mg) were added. The mixture was stirred under N$_2$ for 4 hours then filtered. After concentration and chromatography (SiO$_2$, 5% MeOH in CH$_2$Cl$_2$), the product was obtained as a 0.47 g of a clear glass (68%). $^1$H NMR (CDCl$_3$, 300 MHz) δ 7.30 (m, 5 H), 5.19 (bs, 1 H), 5.09 (bs, 3 H), 5.01 (bs, 1 H), 4.75 (m, 1 H), 4.06-3.89 (m, 6 H), 2.33 (m, 2 H), 2.19 (s, 3 H) 2.05-1.01 (series of multiplets, 26 H), 1.47 (s, 9 H), 1.45 (s, 18 H), 0.92 (s, 3 H), 0.80 (d, J=6.4 Hz, 3 H), 0.72 (s, 3H). $^{13}$C NMR (CDCl$_3$, 75 MHz) δ 170.01, 169.86, 169.69, 155.72, 155.55, 139.90, 129.05, 128.17, 126.88, 79.86, 76.53, 75.09, 72.09, 62, 35, 57.88, 47.78, 45.23, 43.12, 42.79, 42.16, 40.81, 37.94, 35.51, 34.69, 34.57, 34.36, 33.30, 31.31, 29.66, 28.80, 28.34, 27.22, 26.76, 25.61, 24.02, 22.83, 22.47, 17.93, 12.19; FAB-MS (thioglycerol matrix) m/e: ([M+H]$^+$) 970 (100%), calcd. 970.

Compound 33: Compound 31 (0.39 g, 0.79 mmol) was dissolved in CH$_2$Cl$_2$ (15 mL) and Boc-β-alanine (0.60 g, 3.17 mmol), DCC (0.73 g, 3.56 mmol) and dimethylaminopyridine (DMAP) (about 100 mg) were added. The mixture was stirred under N$_2$ for 6 hours then filtered. After concentration and chromatography (SiO$_2$, 5% MeOH in CH$_2$Cl$_2$), the product was obtained as a 0.58 g of a clear glass (72%). IR (neat) 3400, 2980, 1705, 1510 cm$^{-1}$; $^1$H NMR (CDCl$_3$, 300 MHz) δ 7.27 (m, 5 H), 5.12 (bs, 4 H), 4.93 (bs, 1 H), 4.71 (m, 1 H), 3.40 (m, 12 H), 2.59-2.48 (m, 6 H), 2.28 (m, 2 H), 2.17 (s, 3 H), 2.05-1.01 (series of multiplets, 26 H), 1.40 (s, 27 H), 0.90 (s, 3 H), 0.77 (d, J=6.1 Hz, 3 H), 0.70 (s, 3 H). $^{13}$C NMR (CDCl$_3$, 75 MHz) δ 171.85, 171.50, 171.44, 155.73, 138.62, 129.02, 128.09, 126.87, 79.18, 75.53, 74.00, 70.91, 62.20, 57.67, 47.84, 44.99, 43.28, 41.98, 40.73, 37.67, 36.12, 34.94, 34.65, 34.47, 34.20, 33.29, 31.23, 29.57, 28.74, 28.31, 28.02, 27.86, 27.12, 26.73, 25.46, 24.86, 23.95, 22.77, 22.39, 17.91, 12.14; HRFAB-MS (thioglycerol+Na$^+$ matrix) m/e: ([M+H]$^+$) 1011.6619 (100%), calcd. 1011.6634.

Compound 6: Compound 32 (0.15 g, 0.15 mmol) was stirred with excess 4 N HCl in dioxane for 40 minutes. The dioxane and HCl were removed in vacuo leaving 0.12 g of a clear glass (about 100%). $^1$H NMR (CD$_3$OD, 300 MHz) δ 7.62 (bs, 2 H), 7.48 (bs, 3 H), 5.30 (bs, 1 H), 5.11 (bs, 1 H), 4.72 (bs (1 H), 4.46 (m, 1 H), 4.32 (m, 1 H) 4.05-3.91 (m, 4 H), 3.10 (m, 2 H), 2.81 (s, 3 H), 2.15-1.13 (series of multiplets, 25 H), 1.00 (s, 3 H), 0.91 (bs, 3 H), 0.82 (s, 3 H). $^{13}$C NMR (CD$_3$OD, 125 MHz) δ 166.86, 166.50, 131.09, 130.18, 129.17, 128.55, 76.60, 75.43, 72.61, 72.04, 70.40, 66.22, 60.07, 58.00, 57.90, 54.89, 54.76, 46.44, 44.64, 43.39, 42.22, 38.56, 36.78, 34.14, 33.92, 33.84, 31.82, 30.54, 29.67, 28.79, 27.96, 26.79, 26.00, 24.99, 23.14, 22.05, 21.82, 19.91, 17.27, 11.60; HRFAB-MS (thioglycerol+Na$^+$ matrix) m/e: ([M-4 Cl-3 H]$^+$) 669.4576 (100%), calcd. 669.4591.

Compound 7: Compound 33 (0.20 g, 0.20 mmol) was stirred with excess 4 N HCl in dioxane for 40 minutes. The dioxane and HCl were removed in vacuo leaving 0.12 g of a clear glass (about 100%). $^1$H NMR (CD$_3$OD, 500 MHz) δ 7.58 (bs, 2 H), 7.49 (bs, 3 H), 5.21 (bs, 1 H), 5.02 (bs, 1 H), 4.64 (m, 1 H), 4.44 (m, 1 H), 4.28 (m, 1 H), 3.30-2.84 (m, 14 H), 2.80 (s, 3 H), 2.11-1.09 (series of multiplets, 25 H), 0.99 (s, 3 H), 0.89 (d, J=4.1 Hz, 3 H), 0.80 (s, 3 H); $^{13}$C NMR (CD$_3$OD, 125 MHz) δ 171.92, 171.56, 171.49, 132.44, 131.32, 131.02, 130.51, 78.13, 76.61, 61.45, 57.94, 46.67, 44.80, 42.36, 40.85, 39.33, 37.03, 36.89, 36.12, 36.09, 35.79, 35.63, 33.81, 33.10, 32.92, 32.43, 30.28, 28.43, 28.04, 26.65, 24.02, 22.86, 21.98, 18.70, 12.68; HRFAB-MS (thioglycerol+Na$^+$ matrix) m/e: ([M-4 Cl-3 H]$^+$) 711.5069 (43%), calcd. 711.5061.

Example 4

This example includes a description of one or more exemplary synthetic procedures for obtaining Compounds 8, CSA-7, CSA-8 and 34-40.

Compound 34: Diisopropyl azodicarboxylate (DIAD) (1.20 mL, 6.08 mmol) was added to triphenylphosphine (1.60 g, 6.08 mmol) in THF (100 mL) at 0° C. and was stirred for half an hour during which time the yellow solution became a paste. Compound 14 (2.58 g, 4.06 mmol) and p-nitrobenzoic acid (0.81 g, 4.87 mmol) were dissolved in THF (50 mL) and added to the paste. The resulted mixture was stirred at ambient temperature overnight. Water (100 mL) was added and the mixture was made slightly basic by adding NaHCO$_3$ solution followed by extraction with EtOAc (3×50 mL). The combined extracts were washed with brine once and dried over anhydrous Na$_2$SO$_4$. The desired product (2.72 g, 85% yield) was obtained as white powder after SiO$_2$ chromatography (Et$_2$O/hexanes 1:2). m.p. 207-209° C.; IR (KBr) 3434, 3056, 2940, 2868, 1722, 1608, 1529, 1489, 1448, 1345 cm$^{-1}$; $^1$H NMR (CDCl$_3$, 300 MHz) δ 8.30-8.26 (m, 2 H), 8.21-8.16 (m, 2 H), 7.46-7.42 (m, 6 H), 7.31-7.18 (m, 9 H) 5.33 (bs, 1 H), 4.02 (bs, 1 H), 3.90 (bs, 1 H), 3.09-2.97 (m, 2 H), 2.68 (td, J=14.95, 2.56 Hz, 1 H), 2.29-2.19 (m, 1 H), 2.07-1.06 (series of multiplets, 24 H), 1.01 (s, 3 H), 0.98 (d, J=6.6 Hz, 3 H), 0.70 (s, 3 H); $^{13}$C NMR (CDCl$_3$, 75 MHz) δ 164.21, 150.56, 144.70, 136.79, 130.77, 128.88, 127.86, 126.98, 123.70, 86.47, 73.24, 73.00, 68.70, 64.22, 47.79, 46.79, 42.15, 39.76, 37.47, 35.52, 35.34, 34.23, 33.79, 32.46, 31.12, 28.74, 27.71, 26.85, 26.30, 25.16, 23.41, 17.98, 12.77; HRFAB-MS (thioglycerol+Na$^+$ matrix) m/e: ([M+Na]$^+$) 808.4203 (53.8%), calcd. 808.4189. Nitrobenzoate (2.75 g, 3.5 mmol) was dissolved in CH$_2$Cl$_2$ (40 mL) and MeOH (20 mL) and 20% aqueous NaOH (5 mL) were added. The mixture was heated up to 60° C. for 24 hours. Water (100 mL) was introduced and extracted with EtOAc. The combined extracts were washed with brine and dried over anhydrous Na$_2$SO$_4$. The desired product (1.89 g, 85% yield) was obtained as white solid after SiO$_2$ chromatography (3% MeOH in CH$_2$Cl$_2$ as eluent). m.p. 105-106° C.; IR (KBr) 3429, 3057, 2936, 1596, 1489, 1447, 1376, 1265, 1034, 704 cm$^{-1}$; $^1$H NMR (CDCl$_3$, 300 MHz) δ 7.46-7.42 (m, 6 H), 7.32-7.19 (m, 9 H), 4.06 (bs, 1 H), 3.99 (bs, 1 H), 3.86 (bd, J=2.44 Hz, 1 H), 3.09-2.97 (m, 2 H), 2.47 (td, J=14.03, 2.44 Hz, 1 H), 2.20-2.11 (m, 1 H), 2.04-1.04 (series of multiplets, 25 H), 0.97 (d, J=6.59 Hz, 3 H), 0.94 (s, 3 H), 0.68 (s, 3 H); $^{13}$C NMR (CDCl$_3$, 75 MHz) δ 144.70, 128.88, 127.86, 126.97, 86.45, 73.31, 68.84, 67.10, 64.23, 47.71, 46.74, 42.10, 39.70, 36.73, 36.73, 36.15, 35.53, 35.45, 34.45, 32.46, 29.93, 28.67, 27.86, 27.71, 26.87, 26.04, 23.43, 23.16, 17.94, 12.75; HRFAB-MS (thioglycerol+Na$^+$ matrix) m/e: ([M+Na]$^+$) 659.4064 (100%), calcd. 659.4076.

Compound 35: To a round-bottom flask were added 34 (2.0 g, 3.14 mmol), NaH (60% in mineral oil, 3.8 g, 31.4 mmol) and THF (150 mL). The suspension was refluxed for 2 hours followed by the addition of allyl bromide (2.72 mL, 31.4 mL). After refluxing for 28 hours, another 10 eq. of NaH and allyl bromide were added. After 72 hours, another 10 eq. of NaH and allyl bromide were added. After 115 hours, TLC showed almost no starting material or intermediates. Water (100 mL) was added to the suspension carefully, followed by extraction with EtOAc (5×50 mL). The combined extracts were washed with brine and dried over anhydrous Na$_2$SO$_4$. The desired product (1.81 g, 79% yield) was obtained as a yellowish glass after SiO$_2$ chromatography (5% EtOAc/hexanes). IR (neat) 3060, 3020, 2938, 2865, 1645, 1596, 1490, 1448, 1376, 1076, 705 cm$^{-1}$; $^1$H NMR (CDCl$_3$, 300 MHz) δ 7.46-7.42 (m, 6 H), 7.31-7.18 (m, 9 H), 6.06-5.85 (m, 3 H), 5.35-5.20 (m, 3 H), 5.15-5.06 (m, 3 H), 4.10-4.00 (m, 2 H), 3.93-3.90 (m, 2 H), 3.85-3.79 (ddt, J=13.01, 4.88, 1.59 Hz, 1 H), 3.73-3.66 (ddt, J=13.01, 5.38, 1.46 Hz, 1 H), 3.58 (bs, 1 H), 3.54 (bs, 1 H), 3.32 (d, J=2.93 Hz, 1 H), 3.07-2.96 (m, 2 H), 2.36 (td, J=13.67, 2.68 Hz, 1 H), 2.24-2.10 (m, 2 H), 2.03-1.94 (m, 1 H), 1.87-0.86 (series of multiplets, 20 H), 0.91 (s, 3 H), 0.90 (d, J=6.83 Hz, 3 H), 0.64 (s, 3 H); $^{13}$C NMR (CDCl$_3$, 75 MHz) δ 144.77, 136.29, 136.21, 136.13, 128.90, 127.86, 126.94, 116.13, 115.51, 115.42, 86.44, 81.11, 75.65, 73.92, 69.40, 68.81, 64.43, 46.68, 46.54, 42.93, 39.93, 36.98, 35.66, 35.14, 35.14, 32.83, 32.54, 30.48, 28.51, 27.72, 27.64, 26.82, 24.79, 23.65, 23.43, 23.40, 18.07, 12.80; HRFAB-MS (thioglycerol+Na$^+$ matrix) m/e: ([M+H]$^+$) 757.5185 (12.9%), calcd. 757.5196.

Compound 36: Ozone was bubbled through a solution of 35 (0.551 g, 0.729 mmol) in CH$_2$Cl$_2$ (40 mL) and MeOH (20 mL) at −78° C. until the solution turned a deep blue. Excess ozone was blown off with oxygen. Methylsulfide (1 mL) was added followed by the addition of NaBH$_4$ (0.22 g, 5.80 mmol) in 5% NaOH solution and methanol. The resulted mixture was stirred overnight at room temperature and washed with brine. The brine was then extracted with EtOAc (3×20 mL). The combined extracts were dried over Na$_2$SO$_4$. The desired product (0.36 g, 65% yield) was obtained as a colorless glass after SiO$_2$ chromatography (5% MeOH/CH$_2$Cl$_2$). IR (neat) 3396, 3056, 2927, 1596, 1492, 1462, 1448, 1379, 1347, 1264, 1071 cm$^{-1}$; $^1$H NMR (CDCl$_3$, 300 MHz) δ 7.46-7.42 (m, 6 H), 7.32-7.18 (m, 9 H), 3.77-3.57 (series of multiplets, 10 H), 3.48-3.44 (m, 2 H), 3.36-3.30 (m, 2 H), 3.26-3.20 (m, 1 H), 3.04-2.99 (m, 2 H), 2.37-0.95 (series of multiplets, 27 H), 0.92 (s, 3 H), 0.91 (d, J=6.59 Hz, 3 H), 0.67 (s, 3 H); $^{13}$C NMR (CDCl$_3$, 75 MHz) δ 144.69, 128.87, 127.84, 126.94, 86.44, 81.05, 76.86, 74.65, 69.91, 69.22, 68.77, 64.24, 62.44, 62.42, 62.26, 46.92, 46.54, 42.87, 39.73, 36.86, 35.52, 35.13, 32.82, 32.54, 30.36, 28.71, 27.61, 27.44, 26.79, 24.82, 23.51, 23.38, 23.31, 18.28, 12.74; HRFAB-MS (thioglycerol+Na$^+$ matrix) m/e: ([M+Na]$^+$) 791.4844 (96.4%), calcd. 791.4863.

Compound 37: NEt$_3$ (0.23 mL, 1.66 mmol) was added to a solution of 36 (0.364 g, 0.47 mmol) in dry CH$_2$Cl$_2$ (30 mL) at 0° C. under N$_2$ followed by the introduction of mesyl chloride (0.12 mL, 1.56 mmol). The mixture was stirred for 10 minutes and H$_2$O (10 mL) added to quench the reaction, followed by extraction with EtOAc (3×30 mL). The combined extracts were washed with brine and dried over anhydrous Na$_2$SO$_4$. SiO$_2$ chromatography (EtOAc/hexanes 1:1) gave the desired product (0.411 g, 86% yield) as white glass. IR (neat) 3058, 3029, 2939, 2868, 1491, 1461, 1448, 1349, 1175, 1109, 1019 cm$^{-1}$; $^1$H NMR (CDCl$_3$, 300 MHz) δ 7.46-7.42 (m, 6 H), 7.31-7.19 (m, 9 H), 4.35-4.26 (m, 6 H), 3.84-3.74 (m, 2 H), 3.64-3.56 (m, 4 H), 3.49-3.34 (m, 3 H), 3.06 (s, 3 H), 3.04 (s, 3 H), 3.02 (s, 3 H), 3.09-2.95 (m, 2 H), 2.28 (bt, J=14.89 Hz, 1 H), 2.09-0.86 (series of multiplets, 21 H), 0.92 (s, 3 H), 0.90 (d, J=6.78 Hz, 3 H), 0.66 (s, 3 H); $^{13}$C NMR (CDCl$_3$, 75 MHz) δ 144.66, 128.86, 127.86, 126.97, 86.46, 81.28, 77.18, 75.00, 70.14, 69.89, 69.13, 66.49, 65.85, 65.72, 64.22, 47.06, 46.35, 42.77, 39.58, 37.81, 37.64, 37.55, 36.75, 35.48, 35.02, 32.59, 32.52, 30.27, 28.43, 27.56, 27.52, 26.92, 24.62, 23.34, 23.25, 23.10, 18.24, 12.64; HRFAB-MS (thioglycerol+Na$^+$ matrix) m/e: ([M+Na]$^+$) 1025.4207 (100%), calcd. 1025.4189.

Compound 38: The suspension of 37 (0.227 g, 0.227 mmol) and NaN$_3$ (0.147 g, 2.27 mmol) in dry DMSO (5 mL) was stirred at 80° C. overnight, diluted with H$_2$O (50 mL) and extracted with EtOAc (3×20 mL). The extracts were washed with brine once and dried over anhydrous Na$_2$SO$_4$. SiO$_2$ chromatography (EtOAc/hexanes 1:8) afforded the desired product (0.153 g, 80% yield) as a yellow oil. IR (neat) 2929, 2866, 2105, 1490, 1466, 1448, 1107, 705 cm$^{-1}$; $^1$H NMR (CDCl$_3$, 300 MHz) δ 7.46-7.42 (m, 6 H), 7.32-7.19 (m, 9 H), 3.80-3.74 (m, 1 H), 3.70-3.55 (series of multiplets, 5 H), 3.41-3.19 (series of multiplets, 9 H), 3.04-2.98 (m, 2 H), 2.41 (td, J=13.1, 2.44 Hz, 1 H), 2.29-2.14 (m, 2 H), 2.04-0.86 (series of multiplets, 20 H), 0.93 (s, 3 H), 0.91 (d, J=6.60 Hz, 3 H), 0.66 (s, 3 H); $^{13}$C NMR (CDCl$_3$, 75 MHz) δ 144.78, 128.93, 127.87, 126.96, 86.46, 81.30, 77.16, 75.21, 67.99, 67.44, 67.03, 64.41, 51.64, 51.57, 51,33, 46.71, 46.30, 42.35, 39.75, 36.72, 35.64, 35.20, 32.52, 32.42, 30.17, 28.63, 27.80, 27.22, 26.90, 24.80, 23.55, 23.30, 23.24, 18.23, 12.65; HRFAB-MS (thioglycerol+Na$^+$ matrix) m/e: ([M+Na]$^+$) 866.5049 (96.9%), calcd. 866.5057.

Compound 39: p-Toluenesulfonic acid (1.72 mg) was added into the solution of 38 (0.153 g, 0.18 mmol) in CH$_2$Cl$_2$ (5 mL) and MeOH (5 mL), and the mixture was stirred for 2.5 hours. Saturated NaHCO$_3$ solution (5 mL) was introduced followed by the introduction of brine (30 mL). The aqueous mixture was extracted with EtOAc and the combined extracts washed with brine and dried over Na$_2$SO$_4$. The desired product (0.10 g, 92% yield) was obtained as a pale yellowish oil after SiO$_2$ chromatography (EtOAc/hexanes 1:3). IR (neat) 3426, 2926, 2104, 1467, 1441, 1347, 1107 cm$^{-1}$; $^1$H NMR (CDCl$_3$, 300 MHz) δ 3.81-3.74 (m, 1 H), 3.71-3.54 (m, 7 H), 3.41-3.19 (m, 9 H), 2.41 (td, J=13.61, 2.32 Hz, 1 H), 2.30-2.14 (m, 2 H), 2.07-1.98 (m, 1H), 1.94-0.95 (series of multiplets, 21 H), 0.95 (d, J=6.35 Hz, 3 H), 0.93 (s, 3 H), 0.69 (s, 3 H); $^{13}$C NMR (CDCl$_3$, 75 MHz) δ 81.22, 77.08, 75.13, 67.94, 67.36, 66.97, 63.76, 51.59, 51.51, 51.26, 46.51, 46.24, 42.31, 39.68, 36.64, 35.58, 35.12, 32.34, 31.92, 30.11, 29.55, 28.54, 27.82, 27.16, 24.75, 23.47, 23.23, 23.18, 18.15, 12.56; HRFAB-MS (thioglycerol+Na$^+$ matrix) m/e: ([M+Na]$^+$) 624.3966 (54.9%), calcd. 624.3962.

Compound 40: To a solution of 39 (0.10 g, 0.166 mmol) in CH$_2$Cl$_2$ (8 mL) at 0° C. was added NEt$_3$ (34.8 µL, 0.25 mmol) under N$_2$ followed by the introduction of mesyl chloride (15.5 .mu.L, 0.199 mmol). The mixture was stirred 15 minutes. Addition of H$_2$O (3 mL) and brine (20 mL) was followed by extraction with EtOAc (4×10 mL). The combined extracts were washed with brine once and dried over Na$_2$SO$_4$. After removal of solvent, the residue was mixed with N-benzylmethylamine (0.5 mL) and heated to 80° C. under N$_2$ overnight. Excess N-benzyl methylamine was removed in vacuo and the residue was subjected to SiO$_2$ chromatography (EtOAc/hexanes 1:4) to give the product (0.109 g, 93% yield) as a yellow oil. IR (neat) 2936, 2784, 2103, 1467, 1442, 1346, 1302, 1106, 1027 cm$^{-1}$; $^1$H NMR (CDCl$_3$, 300 MHz) δ 7.32-7.23 (m, 5 H), 3.81-3.74 (m, 1 H), 3.71-3.55 (m, 5 H), 3.47 (s, 2 H), 3.41-3.19 (m, 9 H), 2.46-2.11 (m, 5 H), 2.18 (s, 3 H), 2.03-0.85 (series of multiplets, 20 H), 0.93 (s, 3 H), 0.93 (d, J=6.35 Hz, 3 H), 0.67 (s, 3 H); $^{13}$C NMR (CDCl$_3$, 75 MHz) δ 139.54, 129.26, 128.32, 126.97, 81.26, 77.12, 75.17, 67.98, 67.42, 67.00, 62.50, 58.41, 51.61, 51.54, 51.29, 46.66, 46.28, 42.46, 42.32, 39.72, 36.68, 35.76, 35.16, 33.75, 32.38, 30.15, 28.59, 27.85, 27.19, 24.77, 24.15, 23.53, 23.28, 23.22, 18.28, 12.60; HRFAB-MS (thioglycerol+Na$^+$ matrix) m/e: ([M+H]$^+$) 705.4929 (100%), calcd. 705.4928.

Compound 8: A suspension of 40 (0.109 g, 0.155 mmol) and LiAlH$_4$ (23.5 mg, 0.62 mmol) in THF (20 mL) was stirred under N$_2$ overnight. Na$_2$SO$_4$.10H$_2$O was carefully added and stirred until no grey color persisted. Anhydrous Na$_2$SO$_4$ was added and the white precipitate was filtered out and rinsed with dry THF. After removal of solvent, the residue was dissolved in minimum CH$_2$Cl$_2$ and filtered. The desired product (0.091 g, 94% yield) was obtained as a colorless oil after the solvent was removed. IR (neat) 3371, 3290, 3027, 2938, 2862, 2785, 1586, 1493, 1453, 1377, 1347, 1098 cm$^{-1}$; $^1$H NMR (CDCl$_3$, 300 MHz) δ 7.31-7.21 (m, 5 H), 3.65-3.53 (m, 4 H), 3.47 (s, 2 H), 3.42-3.34 (m, 2 H), 3.30 (bs, 1 H), 3.26-3.20 (m, 1H), 3.14-3.09 (m, 1 H), 2.89-2.81 (m, 6 H), 2.39-2.27 (m, 3 H), 2.17 (s, 3 H), 2.15-0.88 (series of multiplets, 29 H), 0.93 (d, J=6.59 Hz, 3 H), 0.92 (s, 3 H), 0.67 (s, 3 H); $^{13}$C NMR (CDCl$_3$, 75 MHz)

δ 139.34, 129.16, 128.24, 126.90, 80.75, 76.44, 74.29, 70.58, 69.88, 69.75, 62.47, 58.27, 46.66, 46.47, 42.75, 42.63, 42.51, 42.35, 39.77, 36.87, 35.73, 35.04, 33.77, 32.90, 30.38, 28.71, 27.70, 27.32, 24.89, 24.09, 23.53, 23.36, 23.25, 18.24, 12.62; HRFAB-MS (thioglycerol+Na$^+$ matrix) m/e: ([M+H]$^+$) 627.5199 (23.3%), calcd. 627.5213.

Compound CSA-7: To a solution of 23 (0.18 g, 0.28 mmol) in dry DMF (4 mL) were added NaH (0.224 g, 60% in mineral oil, 5.60 mmol) and 1-bromo octane (0.48 mL, 2.80 mmol). The suspension was stirred under N$_2$ at 65° C. overnight followed by the introduction of H$_2$O (60 mL) and extraction with ether (4×20 mL). The combined extracts were washed with brine and dried over Na$_2$SO$_4$. SiO$_2$ chromatography (hexanes and 5% EtOAc in hexanes) afforded the desired product (0.169 g, 80% yield) as a pale yellowish oil. IR (neat) 2927, 2865, 2099, 1478, 1462, 1451, 1350, 1264, 1105 cm$^{-1}$; $^1$H NMR (CDCl$_3$, 300 MHz) δ 3.69-3.35 (series of multiplets, 15 H), 3.26-3.02 (series of multiplets, 4 H), 2.19-2.02 (m, 3 H), 1.97-1.16 (series of multiplets, 37 H), 1.12-0.99 (m, 2 H), 0.92-0.86 (m, 9 H), 0.65 (s, 3 H); $^{13}$C NMR (CDCl$_3$, 75 MHz) δ 80.69, 79.84, 76.13, 71.57, 71.15, 65.07, 64.49, 64.39, 49.08, 48.99, 48.80, 46.68, 46.45, 42.72, 42.05, 39.88, 35.74, 35.49, 35.36, 35.14, 32.42, 32.03, 30.01, 29.85, 29.81, 29.76, 29.67, 29.48, 29.14, 27.92, 27.80, 27.70, 26.58, 26.42, 23.59, 23.09, 22.92, 22.86, 18.11, 14.31, 12.65; HRFAB-MS (thioglycerol+Na$^+$ matrix) m/e: ([M+Na]$^+$) 778.5685 (22.1%), calcd. 778.5683. The triazide (0.169 g, 0.224 mmol) and LiAlH$_4$ (0.025 g, 0.67 mmol) were suspended in anhydrous THF (10 mL) and stirred under N$_2$ at room temperature overnight followed by careful introduction of Na$_2$SO$_4$ hydrate. After the grey color disappeared, anhydrous Na$_2$SO$_4$ was added and stirred. The white precipitate was removed by filtration and washed with THF. After removal of solvent, the residue was dissolved in 1 M hydrochloric acid and the aqueous solution was extracted with ether (5 mL) once. The aqueous solution was then made basic by adding 20% aqueous NaOH solution followed by extraction with Et$_2$O (4×5 mL). The combined extracts were washed, dried and concentrated. The residue was then subject to SiO$_2$ chromatography (MeOH/CH$_2$Cl$_2$ (1:1) followed by MeOH/CH$_2$Cl$_2$/NH$_3$·H$_2$O (4:4:1)) to afford the desired product (0.091 g, 60% yield) as a colorless oil. IR (neat) 3361, 2927, 2855, 1576, 1465, 1351, 1105 cm$^{-1}$; $^1$H NMR (CD$_3$OD, 300 MHz) δ 4.86 (bs, 6 H), 3.77-3.72 (m, 1 H), 3.70-3.61 (m, 1 H), 3.57-3.53 (m, 3 H), 3.43-3.38 (m, 4 H), 3.34-3.27 (m, 2 H), 3.18-3.10 (m, 2 H), 2.84-2.71 (m, 6 H), 2.22-2.07 (m, 3 H), 2.00-1.02 (series of multiplets, 39 H), 0.97-0.88 (m, 9 H), 0.71 (s, 3 H); $^{13}$C NMR (CD$_3$OD, 75 MHz) δ 82.20, 81.00, 77.62, 72.52, 72.06, 68.00, 67.92, 67.39, 48.20, 47.53, 44.26, 43.40, 41.42, 41.15, 40.84, 40.35, 36.88, 36.73, 36.42, 36.11, 34.24, 34.05, 33.94, 33.67, 33.17, 30.95, 30.72, 30.62, 29.81, 29.35, 28.87, 28.79, 27.51, 24.57, 23.90, 23.83, 23.44, 18.76, 14.62, 13.07; HRFAB-MS (thioglycerol matrix) m/e: ([M+H]$^+$) 678.6133 (100%), calcd. 678.6149.

Compound CSA-8: A suspension of 23 (0.126 g, 0.196 mmol) and LiAlH$_4$ (0.037 g, 0.98 mmol) in THF (40 mL) was stirred at room temperature under N$_2$ overnight followed by careful addition of Na$_2$SO$_4$·10H$_2$O. After the grey color in the suspension disappeared, anhydrous Na$_2$SO$_4$ was added and stirred until organic layer became clear. The white precipitate was removed by filtration and washed with twice THF. The THF was removed in vacuo, and the residue was subject to SiO$_2$ chromatography (MeOH/CH$_2$Cl$_2$/NH$_3$/H$_2$O (4:4:1)) to afford the desired product (0.066 g, 60% yield) as a colorless oil. IR (neat) 3365, 2933, 2865, 1651, 1471, 1455, 1339, 1103 cm$^{-1}$; $^1$H NMR (CDCl$_3$/30% CD$_3$OD, 300 MHz) δ 4.43 (bs, 7 H), 3.74-3.68 (m, 1 H), 3.66-3.60 (m, 1 H), 3.57-3.50 (m, 5 H), 3.34-3.25 (M, 2 H), 3.17-3.06 (M, 2 H), 2.84-2.74 (M, 6 H), 2.19-2.01 (M, 3 H), 1.97-0.96 (series of multiplets, 27 H), 0.94 (d, J=7.2 Hz, 3 H), 0.92 (s, 3 H), 0.69 (s, 3 H); $^{13}$C NMR (CDCl$_3$, 75 MHz) δ 80.44, 79.27, 75.77, 66.59, 66.53, 65.86, 62.51, 46.21, 45.84, 42.55, 41.53, 40.09, 39.43, 39.31, 39.02, 35.16, 34.93, 34.86, 34.57, 32.93, 32.71, 31.57, 28.66, 28.33, 27.64, 27.22, 23.04, 22.40, 22.29, 17.60, 11.98; HRFAB-MS (thioglycerol+Na$^+$ matrix) m/e: ([M+H]$^+$) 566.4889 (8.9%), calcd. 566.4897.

Example 5

This example includes a description of one or more exemplary synthestic procedures for obtaining Compounds CSA-11 and 43-47.

Compound 43: Precursor compound 41 was prepared following the method reported by D. H. R. Barton, J. Wozniak, S. Z. Zard, Tetrahedron, 1989, vol. 45, 37:41-3754. A mixture of 41 (1.00 g, 2.10 mmol), ethylene glycol (3.52 mL, 63 mmol) and p-TsOH (20 mg, 0.105 mmol) was refluxed in benzene under N$_2$ for 16 hours. Water formed during the reaction was removed by a Dean-Stark moisture trap. The cooled mixture was washed with NaHCO$_3$ solution (50 mL) and extracted with Et$_2$O (50 mL, 2×30 mL). The combined extracts were washed with brine and dried over anhydrous Na$_2$SO$_4$. Removal of the solvent gave the product (1.09 g, 100%) as a white glass. IR (neat) 2939, 2876, 1735, 1447, 1377, 1247, 1074, 1057, 1039 cm$^{-1}$; $^1$H NMR (CDCl$_3$, 300 MHz) δ 5.10 (t, J=2.70 Hz, 1 H), 4.92 (d, J=2.69 Hz, 1 H), 4.63-4.52 (m, 1 H), 3.98-3.80 (m, 4 H), 2.32 (t, J=9.51 Hz, 1 H), 2.13 (s, 3 H), 2.08 (s, 3 H), 2.05 (s, 3 H), 2.00-1.40 (series of multiplets, 15 H), 1.34-0.98 (m, 3 H), 1.20 (s, 3 H), 0.92 (s, 3 H), 0.82 (s, 3 H); $^{13}$C NMR (CDCl$_3$, 75 MHz) δ 170.69, 170.63, 170.47, 111.38, 75.07, 74.23, 70.85, 64.95, 63.43, 49.85, 44.73, 43.39, 41.11, 37.37, 34.84, 34.80, 34.52, 31.42, 29.18, 27.02, 25.41, 24.16, 22.72, 22.57, 22.44, 21.73, 21.63, 13.40; HRFAB-MS (thioglycerol+Na$^+$ matrix) m/e: ([M+H]$^+$) 521.3106 (38.6%), calcd. 521.3114. The triacetate (1.09 g, 2.10 mmol) was dissolved in MeOH (50 mL). NaOH (0.84 g, 21 mmol) was added to the solution. The suspension was then refluxed under N$_2$ for 24 hours. MeOH was then removed in vacuo and the residue was dissolved in Et$_2$O (100 mL) and washed with H$_2$O, brine, and then dried over anhydrous Na$_2$SO$_4$. The desired product (0.80 g, 96% yield) was obtained as white solid after removal of solvent. m.p. 199-200° C. IR (neat) 3396, 2932, 1462, 1446, 1371, 1265, 1078, 1055 cm$^{-1}$; $^1$H NMR (10% CD$_3$OD in CDCl$_3$, 300 MHz) δ 4.08-3.83 (series of multiplets, 9 H), 3.44-3.34 (m, 1 H), 2.41 (t, J=9.28 Hz, 1 H), 2.22-2.10 (m, 2 H), 1.96-1.50 (series of multiplets, 12 H), 1.45-0.96 (series of multiplets, 4 H), 1.32 (s, 3 H), 0.89 (s, 3 H), 0.78 (s, 3 H); $^{13}$C NMR (10% CD$_3$OD in CDCl$_3$, 75 MHz) δ 112.11, 72.35, 71.57, 68.09, 64.54, 63.24, 49.36, 45.90, 41.48, 41.45, 39.18, 38.79, 35.29, 34.71, 34.45, 29.90, 27.26, 26.60, 23.65, 22.54, 22.44, 22.35, 13.46; HRFAB-MS (thioglycerol+Na$^+$ matrix) m/e: ([M+Na]$^+$) 417.2622 (87.3%), calcd. 417.2617.

Compound 44: To a round-bottom flask were added 43 (0.80 g, 2.03 mmol) and dry THF (100 mL) followed by the addition of NaH (60% in mineral oil, 0.81 g, 20.3 mmol). The suspension was refluxed under N$_2$ for 30 minutes before the addition of allyl bromide (1.75 mL, 20.3 mmol). After 48 hours of reflux, another 10 eq. of NaH and allyl bromide were added. After another 48 hours, TLC showed no intermediates left. Cold water (50 mL) was added to the cooled suspension. The resulted mixture was extracted with Et$_2$O (60 mL, 2×30 mL). The combined extracts were washed with brine and dried over anhydrous Na$_2$SO$_4$. SiO$_2$ column chromatography (6% EtOAc in hexanes) gave the desired product (0.94 g, 90% yield) as a pale yellow oil. IR (neat) 3076, 2933, 2866, 1645, 1446, 1423, 1408, 1368, 1289, 1252, 1226, 1206, 1130, 1080, 1057 cm$^{-1}$; $^1$H NMR (CDCl$_3$, 300 MHz) δ 6.02-5.84 (m, 3 H), 5.31-5.04 (m, 6 H), 4.12-4.05 (m, 2 H), 4.01-3.81 (m, 7 H), 3.70 (dd, J=12.94, 5.62 Hz, 1 H), 3.55 (t, J=2.56 Hz, 1 H), 3.33 (d, J=2.93 Hz, 1 H), 3.18-3.08 (m, 1 H), 2.65 (t, J=10.01 Hz, 1 H), 2.32-2.14 (m, 3 H), 1.84-1.45 (series of multiplets, 10 H), 1.41-1.22 (m, 3 H), 1.27 (s, 3 H), 1.14-0.92 (m, 2 H), 0.89 (s, 3 H), 0.75 (s, 3 H); $^{13}$C NMR (CDCl$_3$, 75 MHz) δ 136.38, 136.07, 136.00, 116.31, 115.54, 115.38, 112.34, 80.07, 79.22, 75.05, 69.83, 69.34, 68.82, 65.14, 63.24, 48.80, 45.96, 42.47, 42.15, 39.40, 35.55, 35.16, 35.15, 29.04, 28.22, 27.52, 24.21, 23.38, 23.11, 22.95, 22.58, 13.79; HRFAB-MS (thioglycerol+Na$^+$ matrix) m/e: ([M+Na]$^+$) 537.3549 (100%), calcd. 537.3556.

Compound 45: To the solution of 44 (0.94 g, 1.83 mmol) in dry THF (50 mL) was added 9-BBN (0.5 M solution in THF, 14.7 mL, 7.34 mmol) and the mixture was stirred under N$_2$ at room temperature for 12 hours before the addition of 20% NaOH solution (4 mL) and 30% H$_2$O$_2$ solution (4 mL). The resulted mixture was then refluxed for an hour followed by the addition of brine (100 mL) and extracted with EtOAc (4×30 mL). The combined extracts were dried over anhydrous Na$_2$SO$_4$. After the removal of solvent, the residue was purified by SiO$_2$ column chromatography (EtOAc followed by 10% MeOH in CH$_2$Cl$_2$) to give the product (0.559 g, 54% yield) as a colorless oil. IR (neat) 3410, 2933, 2872, 1471, 1446, 1367, 1252, 1086 cm$^{-1}$; $^1$H NMR (CDCl$_3$, 300 MHz) δ 4.02-3.52 (series of multiplets, 17 H), 3.41-3.35 (m, 1 H), 3.29 (d, J=2.44 Hz, 1 H), 3.22-3.15 (m, 3 H), 2.58 (t, J=10.01 Hz, 1 H), 2.27-1.95 (m, 3 H), 1.83-1.48 (series of multiplets, 16 H), 1.40-0.93 (series of multiplets, 5 H), 1.27 (s, 3 H), 0.90 (s, 3 H), 0.75 (s, 3 H); $^{13}$C NMR (CDCl$_3$, 75 MHz) δ 112.41, 80.09, 79.09, 76.31, 66.70, 66.02, 65.93, 64.80, 63.26, 61.53, 61.25, 60.86, 48.59, 45.80, 42.51, 41.72, 39.10, 35.36, 35.02, 34.98, 32.87, 32.52, 32.40, 28.88, 27.94, 27.21, 24.33, 23.02, 22.84 (2 C's), 22.44, 13.69; HRFAB-MS (thioglycerol+Na$^+$ matrix) m/e: ([M+Na]$^+$) 591.3881 (100%), calcd. 591.3873.

Compound 46: To a solution of 45 (0.559 g, 0.98 mmol) in acetone (40 mL) and water (4 mL) was added PPTS (0.124 g, 0.49 mmol) and the solution was refluxed under N$_2$ for 16 hours. The solvent was removed under reduced pressure. Water (40 mL) was then added to the residue and the mixture was extracted with EtOAc (40 mL, 2×20 mL). The combined extracts were washed with brine, dried and evaporated to dryness. SiO$_2$ column chromatography (8% MeOH in CH$_2$Cl$_2$) of the residue afforded the desired product (0.509 g, 98% yield) as clear oil. IR (neat) 3382, 2941, 2876, 1699, 1449, 1366, 1099 cm$^{-1}$; $^1$H NMR (CDCl$_3$, 300 MHz) δ 3.83-3.72 (m, 8 H), 3.66 (t, J=5.62 Hz, 2 H), 3.54 (bs, 2 H), 3.43-3.28 (m, 4 H), 3.24-3.12 (m, 2 H), 2.26-2.00 (m, 4 H), 2.08 (s, 3 H), 1.98-1.50 (series of multiplets, 15 H), 1.42-0.96 (series of multiplets, 6 H), 0.90 (s, 3 H), 0.62 (s, 3 H); $^{13}$C NMR (CDCl$_3$, 75 MHz) δ 210.49, 78.87 (2 C's), 76.30, 66.86, 66.18, 65.69, 61.74, 61.43, 60.71, 55.31, 48.05, 43.02, 41.58, 39.53, 35.28, 35.09, 34.96, 32.77, 32.70, 32.31, 31.12, 28.72, 27.88, 27.14, 23.47, 22.75, 22.47, 22.34, 13.86; HRFAB-MS (thioglycerol+Na$^+$ matrix) m/e: ([M+Na]$^+$) 547.3624 (100%), calcd. 547.3611.

Compound 47: To a solution of 46 (0.18 g, 0.344 mmol) in dry CH$_2$Cl$_2$ (10 mL) at 0° C. was added Et$_3$N (0.168 mL, 1.20 mmol) followed by the addition of mesyl chloride (0.088 mL, 1.13 mmol). After 10 minutes, H$_2$O (3 mL) and brine (30 mL) were added. The mixture was extracted with EtOAc (30 mL, 2×10 mL) and the extracts were washed with brine and dried over anhydrous Na$_2$SO$_4$. After removal of solvent, the residue was dissolved in DMSO (5 mL) and NaN$_3$ (0.233 g, 3.44 mmol). The suspension was heated up to 50° C. under N$_2$ for 12 hours. H$_2$O (50 mL) was added to the cool suspension and the mixture was extracted with EtOAc (30 mL, 2×10 mL) and the extracts were washed with brine and dried over anhydrous Na$_2$SO$_4$. SiO$_2$ column chromatography (EtOAc/hexanes 1:5) afforded the product (0.191 g, 88% yield for two steps) as a pale yellow oil. IR (neat) 2933, 2872, 2096, 1702, 1451, 1363, 1263, 1102 cm$^{-1}$; $^1$H NMR (CDCl$_3$, 300 MHz) δ 3.72-3.64 (m, 2 H), 3.55-3.24 (series of multiplets, 11 H), 3.18-3.02 (m, 2 H), 2.22-2.02 (m, 4 H), 2.08 (s, 3 H), 1.95-1.46 (series of multiplets, 15 H), 1.38-0.96 (series of multiplets, 6 H), 0.89 (s, 3H), 0.62 (s, 3 H); $^{13}$C NMR (CDCl$_3$, 75 MHz) δ 210.36, 79.69, 79.22, 75.98, 65.08, 64.80, 64.53, 55.31, 48.93, 48.86, 48.76, 48.06, 43.03, 41.91, 39.66, 35.44, 35.31, 35.12, 31.04, 29.77, 29.69, 29.67, 28.99, 28.10, 27.65, 23.60, 22.99, 22.95, 22.50, 14.00; HRFAB-MS (thioglycerol+Na$^+$ matrix) m/e: ([M+Na]$^+$) 622.3820 (100%), calcd. 622.3805.

Compound CSA-11: Compound 47 (0.191 g, 0.319 mmol) was dissolved in dry THF (20 mL) followed by the addition of LiAlH$_4$ (60.4 mg, 1.59 mmol). The grey suspension was stirred under N$_2$ at room temperature for 12 hours. Na$_2$SO$_4$.10H$_2$O powder was carefully added. After the grey color in the suspension disappeared, anhydrous Na$_2$SO$_4$ was added and the precipitate was filtered out. After the removal of solvent, the residue was purified by column chromatography (silica gel, MeOH/CH$_2$Cl$_2$/28% NH$_3$.H$_2$O 3:3:1). After most of the solvent was rotavapped off from the fractions collected, 5% HCl solution (2 mL) was added to dissolve the milky residue. The resulted clear solution was then extracted with Et$_2$O (2×10 mL). 20% NaOH solution was then added until the solution became strongly basic. CH$_2$Cl$_2$ (20 mL, 2×10 mL) was used to extract the basic solution. The combined extracts were dried over anhydrous Na$_2$SO$_4$ and removal of solvent gave the desired product (0.115 g, 69% yield) as a colorless oil. From $^1$H NMR it appears that this compound was a mixture of two stereoisomers at C$_{20}$ with a ratio of approximately 9:1. The stereoisomers were not separated, but used as recovered. Spectra for the most abundant isomer: IR (neat) 3353, 2926, 2858, 1574, 1470, 1366, 1102 cm$^{-1}$; $^1$H NMR (20% CDCl$_3$ in CD$_3$OD, 300 MHz) δ 4.69 (bs, 7 H), 3.76-3.69 (m, 1 H), 3.63-3.53 (m, 5 H), 3.50-3.40 (m, 1 H), 3.29 (bs, 1 H), 3.18-3.07 (m, 2 H), 2.94-2.83 (m, 1 H), 2.81-2.66 (m, 5 H), 2.23-2.06 (m, 4 H), 1.87-1.50 (series of multiplets, 15 H), 1.39-0.96 (series of multiplets, 6 H), 1.11 (d, J=6.10 Hz, 3 H), 0.93 (s, 3 H), 0.75 (s, 3 H); $^{13}$C NMR (20% CDCl$_3$ in CD$_3$OD, 75 MHz) δ 81.46, 80.67, 77.32, 70.68, 67.90, 67.66, 67.18, 50.32, 47.17, 43.30, 43.06, 40.74, 40.64, 40.38, 40.26, 36.31, 36.28, 35.93, 34.30, 34.02, 33.29, 29.63, 29.31, 28.43, 26.10, 24.67, 24.09, 23.96, 23.50, 13.30 for the major isomer; HRFAB-MS (thioglycerol+Na$^+$ matrix) m/e: ([M+H]$^+$) 524.4431 (64.2%), calcd. 524.4427.

Example 6

This example includes a description of one or more exemplary synthetic procedures for obtaining Compounds CSA-10 and 48-49.

Compound 48: To a solution of 23 (0.15 g, 0.233 mmol) in dry $CH_2Cl_2$ (15 mL) at 0° C. was added $Et_3N$ (48.8 µL, 0.35 mmol) followed by the addition of $CH_3SO_2Cl$ (21.7 µL, 0.28 mmol). The mixture was stirred for 15 minutes before $H_2O$ (3 mL) was added. Saturated NaCl solution (20 mL) was then added, and the mixture was extracted with EtOAc (40 mL, 2×20 mL). The combined extracts were washed with brine and dried over anhydrous $Na_2SO_4$. The solvent was rotovapped off and to the residue were added NaBr (0.12 g, 1.17 mmol) and DMF (10 mL). The suspension was heated up to 80° C. under $N_2$ for 2 hours. DMF was removed under vacuum and the residue was chromatographed on silica (EtOAc/hexanes 1:10) to give the desired product (0.191 g, 97% yield) as a pale yellow oil. $^1$H NMR ($CDCl_3$, 300 MHz) δ 3.69-3.35 (series of multiplets, 13 H), 3.28-3.02 (series of multiplets, 4 H), 2.18-2.04 (m, 3 H), 2.00-1.60 (series of multiplets, 16 H), 1.58-0.96 (series of multiplets, 11 H), 0.92 (d, J=6.34 Hz, 3 H), 0.89 (s, 3 H), 0.66 (s, 3 H); $^{13}$C NMR ($CDCl_3$, 75 MHz) δ 80.62, 79.81, 76.08, 65.07, 64.50, 64.34, 49.03, 48.98, 48.79, 46.49, 46.46, 42.73, 42.02, 39.85, 35.47, 35.34, 35.12, 34.79, 34.72, 29.82, 29.80, 29.74, 29.11, 27.91, 27.78, 27.69, 23.55, 23.07, 22.88, 18.10, 12.62; HRFAB-MS (thioglycerol+$Na^+$ matrix) m/e: ([M−H]$^+$) 706.3609 (63.1%), calcd. 706.3591; 704.3616 (52.8%), calcd. 704.3611.

Compound 49: Compound 48 (0.191 g, 0.269 mmol) and 23 (0.295 g, 0.459 mmol) was dissolved in DMF (3 mL, distilled over BaO at 6 mm Hg before use) followed by the addition of NaH (0.054 g, 60% in mineral oil). The suspension was stirred under $N_2$ at room temperature for 24 hours. $H_2O$ (100 mL) was added to quench excess NaH and the mixture was then extracted with $Et_2O$ (40 mL, 3×20 mL) and the combined extracts were washed with brine and dried over anhydrous $Na_2SO_4$. The desired product (0.177 g, 52% yield based on compound 23) was obtained as a pale yellow oil after $SiO_2$ chromatography (EtOAc/hexanes 1:6, then 1:2). IR (neat) 2940, 2862, 2095, 1472, 1456, 1362, 1263, 1113 cm$^{-1}$; $^1$H NMR ($CDCl_3$, 300 MHz) δ 3.68-3.35 (series of multiplets, 26 H), 3.28-3.02 (series of multiplets, 8 H), 2.20-2.04 (m, 6 H), 1.96-1.60 (series of multiplets, 30 H), 1.52-0.98 (series of multiplets, 12 H), 0.91 (d, J=6.59 Hz, 6 H), 0.89 (s, 6 H), 0.65 (s, 6 H); $^{13}$C NMR ($CDCl_3$, 75 MHz) δ 80.68, 79.83, 76.13, 71.71, 65.06, 64.48, 64.39, 49.08, 48.98, 48.80, 46.64, 46.44, 42.71, 42.04, 39.88, 35.73, 35.49, 35.36, 35.14, 32.41, 29.84, 29.81, 29.76, 29.14, 27.92, 27.78, 27.69, 26.58, 23.59, 23.08, 22.92, 18.12, 12.64.

Compound CSA-10: Compound 49 (0.219 g, 0.173 mmol) was dissolved in dry THF (10 mL) followed by the addition of LiAlH$_4$ (65 mg, 1.73 mmol). The grey suspension was stirred under $N_2$ at room temperature for 12 hours. $Na_2SO_4 \cdot 10H_2O$ powder was carefully added. After the grey color in the suspension disappeared, anhydrous $Na_2SO_4$ was added and the precipitate was filtered out. After the removal of solvent, the residue was purified by column chromatography (silica gel, MeOH/$CH_2Cl_2$/28% $NH_3 \cdot H_2O$ 2.5:2.5:1). After most of the solvent was rotavapped off from the fractions collected, 5% HCl solution (2 mL) was added to dissolve the milky residue. The resulted clear solution was then extracted with $Et_2O$ (2×10 mL). 20% NaOH solution was then added until the solution became strongly basic. $CH_2Cl_2$ (20 mL, 2×10 mL) was used to extract the basic solution. The combined extracts were dried over anhydrous $Na_2SO_4$ and removal of solvent gave the desired product (0.147 g, 76% yield) as a white glass. IR (neat) 3364, 3287, 2934, 2861, 1596, 1464, 1363, 1105 cm$^{-1}$; $^1$H NMR (20% $CDCl_3$ in $CD_3OD$, 500 MHz) δ 4.74 (bs, 12 H), 3.75-3.70 (m, 2 H), 3.65-3.61 (m, 2 H), 3.57-3.52 (m, 6 H), 3.40 (t, J=3.60 Hz, 4 H), 3.30 (bs, 4 H), 3.16-3.10 (m, 4 H), 2.84-2.73 (m, 12 H), 2.18-2.07 (m, 6 H), 1.97-1.61 (series of multiplets, 30 H), 1.58-0.98 (series of multiplets, 24 H), 0.95 (d, J=6.84 Hz, 6 H), 0.94 (s, 6 H), 0.70 (s, 6 H); $^{13}$C NMR (20% $CDCl_3$ in $CD_3OD$, 125 MHz) δ 81.70, 80.52, 77.09, 72.34, 67.75 (2 C's), 67.07, 47.80, 47.13, 43.76, 42.87, 41.20, 40.65, 40.58, 40.14, 36.43, 36.25, 36.08, 35.77, 34.15, 33.87 (2 C's), 33.18, 29.55, 28.92, 28.47, 28.42, 27.25, 24.27, 23.54, 23.41, 18.70, 13.07; HRFAB-MS (thioglycerol+$Na^+$ matrix) m/e: ([M+H]$^+$) 1113.9625 (68.8%), calcd. 1113.9610.

Example 7

This example includes a description of one or more exemplary synthetic procedures for obtaining Compounds 111-113 and 116a-d.

Compounds 116a-d: Representative procedure: preparation of 116b. NaH (0.06 g, 60% in mineral oil, 1.49 mmol) and propyl bromide (0.136 mL, 1.49 mmol) were added to a DMF solution of compound 23 (described in Li et al., J. Am. Chem. Soc. 1998, 120, 2961) (0.096 g, 0.149 mmol). The suspension was stirred under $N_2$ for 24 hr. $H_2O$ (20 mL) was added, and the mixture was extracted with hexanes (3×10 mL). The combined extracts were dried over $Na_2SO_4$ and concentrated in vacuo. Silica gel chromatography (10% EtOAc in hexanes) afforded the desired product (92 mg, 90% yield) as a pale yellow oil. $^1$H NMR ($CDCl_3$, 500 MHz) δ 3.68-3.64 (m, 1 H), 3.61-3.57 (m, 1 H), 3.52 (t, J=6.1 Hz, 2 H), 3.49 (bs, 1 H), 3.46-3.35 (m, 10 H), 3.25 (d, J=2.4 Hz, 1 H), 3.23-3.19 (m, 1 H), 3.16-3.11 (m, 1 H), 3.09-3.03 (m, 1 H), 2.17-2.03 (m, 3 H), 1.95-1.55 (m, 17 H), 1.51-1.40 (m, 4 H), 1.38-1.17 (m, 5 H), 1.11-0.96 (m, 3 H), 0.93-0.89 (m, 9 H), 0.65 (s, 3 H); $^{13}$C NMR ($CDCl_3$, 75 MHz) δ 80.64, 79.79, 76.08, 72.67, 71.59, 65.01, 64.44, 64.33, 49.04, 48.94, 48.75, 46.61, 46.40, 42.68, 42.00, 39.83, 35.72, 35.45, 35.30, 35.10, 32.38, 29.81, 29.77, 29.72, 29.09, 27.88, 27.76, 27.65, 26.52, 23.55, 23.12, 23.04, 22.87, 18.06, 12.60, 10.79; HRFAB-MS (thioglycerol+$Na^+$ matrix) m/e: ([M+Na]$^+$) 708.4910 (23.5%), calcd. 708.4920.

Compounds 111, CSA-17, and 113: Representative procedure: preparation of CSA-17. Compound 116b (0.092 g, 0.134 mmol) was dissolved in THF (10 mL) followed by the addition of LiAlH$_4$ (0.031 g, 0.81 mmol). The suspension was stirred under $N_2$ for 12 hr. $Na_2SO_4 \cdot 10H_2O$ (about 1 g) was then carefully added. After the gray color in the suspension dissipated, anhydrous $Na_2SO_4$ was added, and the precipitate was removed by filtration. Concentration and silica gel chromatography ($CH_2Cl_2$/MeOH/28% $NH_3 \cdot H_2O$ 12:6:1, then 10:5:1) yielded a glass which was dissolved in 1 M HCl (2 mL). The resulting clear solution was washed with $Et_2O$ (2×10 mL). 20% NaOH solution was added to the aqueous phase until the solution became strongly basic. $CH_2Cl_2$ (3×10 mL) was used to extract the basic solution. The combined extracts were dried over anhydrous $Na_2SO_4$ and concentrated in vacuo to give the desired product (0.045 g, 55% yield) as a white glass. $^1$H NMR (about 20% $CDCl_3$ in $CD_3OD$, 500 MHz) δ 4.73 (bs, 6 H), 3.74-3.70 (m, 1 H), 3.65-3.61 (m, 1 H), 3.55 (t, J=6.3 Hz, 2 H), 3.42-3.38 (m, 4 H), 3.33-3.30 (m, 2 H), 3.16-3.10 (m, 2 H), 2.83-2.73 (m, 6 H), 2.18-2.06 (m, 3 H), 1.96-1.20 (series of multiplets, 26

H), 1.12-0.98 (m, 3 H), 0.95-0.92 (m, 9H), 0.70 (s, 3 H); $^{13}$C NMR (about 20% CDCl$_3$ in CD$_3$OD, 75 MHz) δ 81.67, 80.49, 77.04, 73.44, 72.28, 67.77, 67.71, 67.06, 47.74, 47.08, 43.75, 42.82, 41.21, 40.60, 40.56, 40.12, 36.47, 36.19, 36.04, 35.74, 34.09, 33.82, 33.78, 33.16, 29.49, 28.87, 28.43, 27.18, 24.22, 23.66, 23.49, 23.40, 18.64, 13.04, 11.03; HRFAB-MS (thioglycerol+Na$^+$ matrix) m/e: ([M+H]$^+$) 608.5348 (100%), calcd. 608.5330. 111: $^1$H NMR (about 20% CDCl$_3$ in CD$_3$OD, 500 MHz) δ 4.79 (bs, 6H), 3.74-3.71 (m, 1 H), 3.66-3.62 (m, 1 H), 3.55 (t, J=6.1 Hz, 2 H), 3.52 (bs, 1 H), 3.38-3.28 (series of multiplets, 4 H), 3.33 (s, 3 H), 3.16-3.10 (m, 2H), 2.83-2.72 (m, 6 H), 2.19-2.07 (m, 3 H), 1.97-1.62 (series of multiplets, 15 H), 1.58-1.20 (series of multiplets, 9 H), 1.13-0.98 (m, 3 H), 0.95 (d, J=6.3 Hz, 3 H), 0.93 (s, 3 H), 0.70 (s, 3 H); $^{13}$C NMR (about 20% CDCl$_3$ in CD$_3$OD, 75 MHz) δ 81.82, 80.65, 77.20, 74.43, 67.85, 67.18, 58.90, 47.80, 47.22, 43.91, 43.01, 41.31, 40.78, 40.69, 40.22, 36.63, 36.35, 36.18, 35.86, 34.27, 33.97, 33.26, 29.60, 29.03, 28.58, 28.53, 27.14, 24.33, 23.61, 23.45, 18.68, 13.06; HRFAB-MS (thioglycerol+Na$^+$ matrix) m/e: ([M+Na]$^+$) 602.4855 (100%), calcd. 602.4873. 113: $^1$H NMR (about 50% CDCl$_3$ in CD$_3$OD, 500 MHz) δ 4.08 (bs, 6 H), 3.71-3.67 (m, 1 H), 3.62-3.58 (m, 1 H), 3.53 (t, J=6.3 Hz, 2 H), 3.49 (bs, 1 H), 3.43-3.38 (m, 4 H), 3.31-3.27 (m, 2 H), 3.14-3.07 (m, 2 H), 2.83-2.73 (m, 6 H), 2.16-2.03 (m, 3 H), 1.93-1.17 (series of multiplets, 30 H), 1.10-0.96 (m, 3 H), 0.93-0.89 (m, 9 H), 0.67 (s, 3 H); $^{13}$C NMR (about 50% CDCl$_3$ in CD$_3$OD, 75 MHz) δ 80.51, 79.35, 75.85, 71.29, 70.83, 66.73, 66.62, 65.96, 46.68, 45.98, 42.59, 41.63, 40.20, 39.53, 39.43, 39.21, 35.34, 35.04, 35.00, 34.71, 33.11, 32.90, 32.82, 32.00, 29.15, 28.49, 28.15, 27.75, 27.35, 26.22, 23.18, 22.60, 22.45, 22.34, 17.77, 13.75, 12.22; HRFAB-MS (thioglycerol+Na$^+$ matrix) m/e: ([M+H]$^+$) 636.5679 (100%), calcd. 636.5669.

Example 8

This example includes a description of one or more exemplary synthetic procedures for obtaining Compounds 106 and 124.

Compound 124: Compound 47 (0.256 g, 0.489 mmol) was dissolved in CH$_2$Cl$_2$ (10 mL), and cooled to 0° C. followed by the addition of Na$_2$HPO$_4$ (0.69 g, 4.89 mmol) and urea-hydrogen peroxide complex (UHP) (0.069 g, 0.733 mmol). Trifluoroacetic anhydride (TFAA) (0.138 mL, 0.977 mmol) was then added dropwise. The suspension was stirred for 12 hr, and additional UHP (23 mg, 0.25 mmol) and TFAA (0.069 mL, 0.49 mmol) were added. After another 12 hr, H$_2$O (30 mL) was added, and the resulting mixture was extracted with EtOAc (3×20 mL). The combined extracts were washed with brine (50 mL), dried over anhydrous Na$_2$SO$_4$, and concentrated in vacuo. SiO$_2$ chromatography (EtOAc/hexanes 1:5) afforded the desired product (0.145 g, 55% yield) as a colorless oil. $^1$H NMR (CDCl$_3$, 300 MHz) δ 5.21 (dd, J=9.3 and 7.3 Hz, 1 H), 3.70-3.57 (m, 2 H), 3.55 (t, J=6.0 Hz, 2 H), 3.43-3.37 (m, 6 H), 3.32-3.25 (m, 3 H), 3.17-3.02 (m, 2 H), 2.28-2.05 (m, 4 H), 2.03 (s, 3 H), 1.86-1.19 (series of multiplets, 19 H), 0.97 (dd, J=14.5 and 3.3 Hz, 1 H), 0.90 (s, 3 H), 0.78 (s, 3 H); $^{13}$C NMR (CDCl$_3$, 75 MHz) δ 171.08, 79.71, 78.03, 75.72, 75.53, 65.41, 65.04, 64.53, 48.79, 48.70, 46.49, 41.92, 39.44, 37.81, 35.45, 35.22, 35.10, 29.73, 29.63, 28.89, 28.33, 27.50, 27.34, 23.39, 22.97, 22.92, 21.28, 12.72; HRFAB-MS (thioglycerol+Na$^+$ matrix) m/e: ([M+H]$^+$) 614.3798 (24.5%), calcd. 614.3778.

Compound 106: Compound 124 (0.145 g, 0.236 mmol) was dissolved in CH$_2$Cl$_2$ (2 mL) and MeOH (1 mL). 20% NaOH solution (0.2 mL) was added. The mixture was stirred for 12 hr, and anhydrous Na$_2$SO$_4$ was used to remove water. After concentration in vacuo, the residue was purified by silica gel chromatography (EtOAc/hexanes 1:3) to afford the desired product (0.124 g, 92% yield) as a colorless oil. $^1$H NMR (CDCl$_3$, 300 MHz) δ 4.29 (bs, 1 H), 3.69-3.60 (m, 2 H), 3.52 (t, J=6.0 Hz, 2 H), 3.45-3.32 (m, 8 H), 3.26 (d, J=2.7 Hz, 1 H), 3.17-3.02 (m, 2 H), 2.19-1.94 (m, 4 H), 1.90-1.62 (series of multiplets, 13 H), 1.57-1.20 (series of multiplets, 7 H), 0.97 (dd, J=14.3 and 3.1 Hz, 1 H), 0.90 (s, 3 H), 0.73 (s, 3 H); $^{13}$C NMR (CDCl$_3$, 75 MHz) δ 79.69, 78.03, 75.47, 73.38, 65.46, 65.00, 64.47, 48.87, 48.68, 46.83, 41.93, 39.71, 37.87, 35.43, 35.20, 35.09, 29.96, 29.69, 29.59, 29.53, 28.89, 28.44, 27.48, 23.72, 22.91, 22.71, 11.77. The alcohol (0.124 g, 0.216 mmol) was dissolved in dry THF (20 mL) followed by the addition of LiAlH$_4$ (33 mg, 0.866 mmol). The gray suspension was stirred under N$_2$ for 12 hr. Na$_2$SO$_4$.10 H$_2$O (about 2 g) was carefully added. After the gray color in the suspension dissipated, anhydrous Na$_2$SO$_4$ was added and the precipitate was removed by filtration. After the removal of solvent, the residue was purified by column chromatography (SiO$_2$, MeOH/CH$_2$Cl$_2$/28% NH$_3$.H$_2$O 2.5:2.5:1). After concentration of the relevant fractions, 1 M HCl (2 mL) was added to dissolve the milky residue. The resulting clear solution was washed with Et$_2$O (2×10 mL). To the aqueous phase, 20% NaOH solution was added until the solution became strongly basic. CH$_2$Cl$_2$ (20 mL, 2×10 mL) was used to extract the basic solution. The combined extracts were dried over anhydrous Na$_2$SO$_4$ and removal of solvent gave the desired product (0.050 g, 47% yield) as a colorless oil. $^1$H NMR (20% CDCl$_3$ in CD$_3$OD, 300 MHz) δ 4.77 (s, 7 H), 4.25 (t, J=8.5 Hz, 1 H), 3.75-3.68 (m, 1 H), 3.66-3.58 (m, 1 H), 3.55 (t, J=6.1 Hz, 2 H), 3.48-3.41 (m, 1 H), 3.34 (bs, 1 H), 3.30 (d, J=3.6 Hz, 1 H), 3.17-3.08 (m, 2 H), 2.86-2.70 (m, 6 H), 2.20-1.91 (m, 4 H), 1.88-1.16 (series of multiplets, 19 H), 1.00 (dd, J=14.2 and 3.0 Hz, 1 H), 0.93 (s, 3 H), 0.73 (s, 3 H); $^{13}$C NMR (20% CDCl$_3$ in CD$_3$OD, 75 MHz) δ 80.62, 79.12, 76.74, 73.77, 68.50, 67.79, 67.17, 47.69, 43.04, 40.76, 40.64, 40.62, 40.22, 39.01, 36.32, 36.25, 35.94, 34.27, 33.97, 33.72, 30.13, 29.53, 28.43, 24.48, 23.58, 23.40, 12.38; HRFAB-MS (thioglycerol+Na$^+$ matrix) m/e: ([M+H]$^+$) 496.4108 (100%), calcd. 496.4114.

Example 9

This example includes a description of one or more exemplary synthestic procedures for obtaining Compounds 109 and 126-129.

Compound 126: Compound 125 (2.30 g, 3.52 mmol) was dissolved in MeOH (50 mL) and CH$_2$Cl$_2$ (100 mL). A small amount of Et$_3$N was added, and the solution was cooled to −78° C. Ozone was bubbled through the solution until a blue color persisted. Me$_2$S (4 mL) was introduced followed by the addition of NaBH$_4$ (0.266 g, 0.703 mmol) in MeOH (10 mL). The resulting solution was allowed to warm and stir overnight. The solution was concentrated in vacuo, and brine (60 mL) was added. The mixture was extracted with EtOAc (40 ml, 2×30 mL), and the combined extracts were washed with brine and dried over anhydrous Na$_2$SO$_4$. Silica gel chromatography (EtOAc) afforded the product (1.24 g, 76% yield) as a white solid. m.p. 219-220 C.; $^1$H NMR (CDCl$_3$, 300 MHz) δ 5.10 (t, J=2.8 Hz, 1 H), 4.90 (d, J=2.7 Hz, 1 H), 3.73-3.59 (m, 2 H), 3.56-3.44 (m, 1 H), 2.13 (s, 3 H), 2.09 (s, 3 H), 2.07-0.95 (series of multiplets, 23 H), 0.91 (s, 3 H), 0.83 (d, J=6.3 Hz, 3 H), 0.74 (s, 3 H); $^{13}$C NMR (CDCl$_3$, 75 MHz) δ 170.84, 170.82, 75.63, 71.77, 71.03, 60.73, 48.10, 45.26, 43.54, 41.16, 38.78, 37.89, 35.00, 34.43, 32.26, 31.50, 30.60, 29.07, 27.50, 25.70, 22.96, 22.71, 21.81, 21.63, 18.18, 12.35; HRFAB-MS (thioglycerol+Na$^+$ matrix) m/e: ([M+H]+) 465.3197 (20%), calcd. 465.3216.

Compound 127: Compound 126 (1.24 g, 2.67 mmol) was dissolved in MeOH (30 mL), and NaOH (0.54 g, 13.4 mmol) was added. The suspension was refluxed under $N_2$ for 24 hr. The MeOH was removed in vacuo followed by the addition of $H_2O$ (50 mL). The precipitate was filtered, washed with $H_2O$ and then dried in vacuo to give a white solid (1.02 g). This solid was dissolved in DMF (40 mL) followed by the sequential addition of $NEt_3$ (1.12 mL, 8.02 mmol), DMAP (16.3 mg, 0.13 mmol) and trityl chloride (1.49 g, 5.34 mmol). The suspension was stirred under $N_2$ for 12 hr and then heated up to 50° C. for 24 hr. $H_2O$ (100 mL) was added to the cooled suspension, and the mixture was extracted with EtOAc (3×50 mL). The combined extracts were washed with brine (100 mL), dried over anhydrous $Na_2SO_4$, and concentrated in vacuo. Silica gel chromatography (EtOAc) afforded the product (1.20 g, 72% yield) as a pale yellow glass. To this glass was added dry THF (80 mL) and NaH (60% in mineral oil, 0.77 g, 19.3 mmol). The suspension was refluxed under $N_2$ for half an hour before the introduction of allylbromide (1.67 mL, 19.3 mmol). After 48 hr at reflux, another 10 eq. of NaH and allylbromide were introduced. After another 48 hr, the reaction mixture was cooled and $H_2O$ (100 mL) was slowly added. The resulting mixture was extracted with hexanes (3×50 mL), and the combined extracts were washed with brine (100 mL) and dried over anhydrous $Na_2SO_4$. Silica gel chromatography (5% EtOAc in hexanes) afforded the product (1.27 g, 64% yield for all three steps) as a clear glass. $^1$H NMR ($CDCl_3$, 300 MHz) δ 7.46-7.43 (m, 6 H), 7.29-7.16 (m, 9 H), 5.98-5.81 (m, 3 H), 5.29-5.18 (m, 3 H), 5.14-5.03 (m, 3 H), 4.11-3.97 (m, 4 H), 3.75-3.67 (m, 2 H), 3.49 (bs, 1 H), 3.32-3.13 (d, J=2.4 Hz, 1 H), 3.20-3.13 (m, 2 H), 3.00 (m, 1 H), 2.33-2.12 (m, 3 H), 2.03-0.92 (series of multiplets, 19 H), 0.88 (s, 3 H), 0.78 (d, J=6.6 Hz, 3 H), 0.65 (s, 3 H); $^{13}$C NMR ($CDCl_3$, 75 MHz) δ 144.71, 136.08, 136.04, 135.94, 128.80, 127.76, 126.86, 116.30, 115.57, 86.53, 80.77, 79.20, 74.96, 69.42, 69.34, 68.81, 62.00, 46.87, 46.48, 42.67, 42.11, 39.90, 36.15, 35.50, 35.14, 35.10, 33.23, 28.99, 28.09, 27.75, 27.56, 23.36, 23.32, 23.12, 18.24, 12.66; HRFAB-MS (thioglycerol+Na$^+$ matrix) m/e: ([M+Na]$^+$) 765.4875 (100%), calcd. 765.4859.

Compound 128: To a THF (40 mL) solution of 127 (1.27 g, 1.71 mmol) was added 9-BBN (0.5 M solution in THF, 17.1 mL). The mixture was stirred for 12 hr before the addition of NaOH (20% solution, 10 mL) and $H_2O_2$ (30% solution, 10 mL). The resulted mixture was refluxed for 1 hr followed by the addition of brine (100 mL) and extraction with EtOAc (4×30 mL). The combined extracts were dried over anhydrous $Na_2SO_4$ and concentrated in vacuo. Silica gel chromatography (5% MeOH in $CH_2Cl_2$) afforded the product (1.26 g, 93% yield) as a clear glass. $^1$H NMR (5% $CD_3OD$ in $CDCl_3$, 300 MHz) □ 7.46-7.43 (m, 6 H), 7.32-7.20 (m, 9 H), 3.94 (s, 3 H), 3.78-3.56 (m, 10 H), 3.48 (bs, 1 H), 3.32-3.26 (m, 2 H), 3.24-3.12 (m, 3 H), 3.00 (dd, J=8.2 and 6.1 Hz, 1 H), 2.23-1.96 (m, 3 H), 1.90-0.95 (series of multiplets, 25 H), 0.90 (s, 3 H), 0.77 (d, J=6.6 Hz, 3 H), 0.66 (s, 3 H); $^{13}$C NMR (5% $CD_3OD$ in $CDCl_3$, 75 MHz) δ 144.52, 128.64, 127.64, 126.76, 86.43, 80.55, 79.31, 77.65, 77.23, 76.80, 76.06, 66.17, 66.01, 65.41, 61.93, 61.20, 60.73, 60.39, 47.29, 46.08, 42.65, 41.62, 39.49, 36.02, 35.10, 34.89, 34.77, 32.89, 32.71, 32.41, 32.26, 28.68, 27.70, 27.51, 27.19, 23.26, 22.66, 22.50, 18.23, 12.34; HRFAB-MS (thioglycerol+Na$^+$ matrix) m/e: ([M+Na]$^+$) 819.5169 (100%), calcd. 819.5099.

Compound 129: To a $CH_2Cl_2$ (50 mL) solution of compound 128 (1.26 g, 1.58 mmol) at 0° C. was added $Et_3N$ (0.92 mL, 6.60 mmol) followed by mesyl chloride (0.47 mL, 6.05 mmol). After 15 minutes, $H_2O$ (10 mL) was followed by brine (80 mL). The mixture was extracted with EtOAc (60 mL, 2×30 mL) and the combined extracts were dried over anhydrous $Na_2SO_4$. After removal of solvent in vacuo, the residue was dissolved in DMSO (10 mL) and $NaN_3$ (1.192 g, 18.3 mmol) was added. The suspension was heated to 60° C. under $N_2$ overnight. $H_2O$ (100 mL) was added, and the mixture was extracted with EtOAc (3×40 mL). The combined extracts were washed with brine and dried over anhydrous $Na_2SO_4$. Removal of the solvent in vacuo afforded a pale yellow oil. The oil was dissolved in MeOH (10 mL) and $CH_2Cl_2$ (20 mL) and TsOH (17.4 mg, 0.092 mmol) was added. After 12 hr, saturated aqueous $NaHCO_3$ (20 mL) and brine (50 mL) were added and the mixture was extracted with EtOAc (3×40 mL). The combined extracts were washed with brine (50 mL) and dried over anhydrous $Na_2SO_4$. Silica gel chromatography (EtOAc/hexanes 1:3) afforded the desired product (0.934, 94%) as a pale yellow oil. $^1$H NMR ($CDCl_3$, 500 MHz) δ 3.75-3.70 (m, 1 H), 3.68-3.63 (m, 2 H), 3.62-3.57 (m, 1 H), 3.53 (t, J=6.1 Hz, 2 H), 3.50 (bs, 1 H), 3.46-3.38 (m, 6 H), 3.26 (d, J=2.4 Hz, 1 H), 3.24-3.20 (m, 1 H), 3.16-3.12 (m, 1 H), 3.10-3.04 (m, 1 H), 2.17-2.04 (m, 3 H), 1.96-1.63 (m, 14 H), 1.53-1.45 (m, 3 H), 1.35-1.20 (m, 7 H), 1.08-1.00 (m, 1 H), 0.97-0.88 (m, 1 H), 0.94 (d, J=6.8 Hz, 3 H), 0.89 (s, 3 H), 0.67 (s, 3 H); $^{13}$C NMR ($CDCl_3$, 75 MHz) δ 80.64, 79.81, 76.06, 65.05, 64.49, 64.34, 61.03, 49.02, 48.98, 48.78, 46.93, 46.53, 42.76, 42.01, 39.83, 39.14, 35.46, 35.33, 35.12, 32.97, 29.79, 29.73, 29.10, 27.90, 27.68, 23.56, 23.06, 22.88, 18.24, 12.60; HRFAB-MS (thioglycerol+Na$^+$ matrix) m/e: ([M+Na]$^+$) 652.4285 (100%), calcd. 652.4295.

Compound 109: Compound 129 (0.245 g, 0.391 mmol) was dissolved in THF (30 mL) followed by the addition of $LiAlH_4$ (59 mg, 1.56 mmol). The gray suspension was stirred under $N_2$ 12 hr. $Na_2SO_4.10H_2O$ powder (about 1 g) was carefully added. After the gray color in the suspension dissipated, anhydrous $Na_2SO_4$ was added and the precipitate was removed by filtration. After the removal of solvent, the residue was purified by silica gel chromatography ($CH_2Cl_2$/MeOH/28% $NH_3.H_2O$ 10:5:1 then 10:5:1.5). The solvent was removed from relevant fractions, and 1 M HCl (4 mL) was added to dissolve the residue. The resulting clear solution was extracted with $Et_2O$ (3×10 mL). 20% NaOH solution was added until the solution became strongly basic. $CH_2Cl_2$ (4×10 mL) was used to extract the basic solution. The combined extracts were dried over anhydrous $Na_2SO_4$, and removal of solvent in vacuo gave the desired product (0.15 g, 71% yield) as a colorless oil. $^1$H NMR (about 20% $CD_3OD$ in $CDCl_3$, 500 MHz) δ 4.73 (bs, 7 H), 3.74-3.70 (m, 1 H), 3.65-3.60 (m, 2 H), 3.56-3.52 (m, 4 H), 3.31-3.28 (m, 2 H), 3.16-3.09 (m, 2 H), 2.82-2.71 (m, 6 H), 2.19-2.06 (m, 3 H), 1.97-1.66 (series of multiplets, 15 H), 1.58-1.48 (m, 3 H), 1.38-0.98 (m, 7 H), 0.96 (d, J=6.8 Hz, 3 H), 0.93 (s, 3 H), 0.71 (s, 3 H); $^{13}$C NMR (about 20% $CD_3OD$ in $CDCl_3$, 75 MHz) δ 81.80, 80.60, 77.17, 67.88, 67.86, 67.18, 60.73, 48.11, 47.28, 43.93, 42.99, 41.34, 40.76, 40.72, 40.24, 39.70, 36.33, 36.18, 35.86, 34.29, 33.99, 33.96, 33.83, 29.60, 29.00, 28.57, 28.54, 24.33, 23.59, 23.48, 18.86, 13.04; HRFAB-MS (thioglycerol+Na$^+$ matrix) m/e: ([M+H]$^+$) 552.4756 (100%), calcd. 552.4772.

Example 10

This example includes a description of one or more exemplary synthetic procedures for obtaining Compounds 108 and 130.

Compound 130: o-$NO_2C_6H_4SeCN$ (0.094 g, 0.21 mmol) and $Bu_3P$ (0.095 mL, 0.38 mmol) were stirred in dry THF (5 mL) at 0° C. for ½ hr followed by the addition of compound 129 (0.10 g, 0.159 mmol) in THF (2 mL). The suspension was stirred for 1 hr followed by the addition of $H_2O_2$ (30% aqueous solution, 2 mL). The mixture was stirred for 12 hr followed by extraction with hexanes (4×10 mL). The combined extracts were dried over anhydrous $Na_2SO_4$. The desired product (0.035 g, 36% yield) was obtained as pale yellowish oil after silical gel chromatography (10% EtOAc/hexanes). $^1$H NMR ($CDCl_3$, 500 MHz) δ 5.73-5.66 (ddd, J=17.1, 10.2, 8.3 Hz, 1H), 4.90 (dd, J=17.1, 2.0 Hz, 1 H), 4.82 (dd, J=10.2 Hz, 1.96 Hz, 1 H), 3.68-3.64 (m, 1 H), 3.62-3.58 (m, 1 H), 3.54-3.26 (m, 9 H), 3.25-3.22 (m, 2 H), 3.15-3.11 (m, 1 H), 3.10-3.04 (m, 1 H), 2.17-1.62 (series of multiplets, 18 H), 1.51-1.43 (m, 2 H), 1.35-1.18 (m, 4 H), 1.06-0.91 (m, 2 H), 1.02 (d, J=6.3 Hz, 3 H), 0.90 (s, 3 H), 0.68 (s, 3 H); $^{13}$C NMR ($CDCl_3$, 75 MHz) δ 145.50, 111.72, 80.60, 79.82, 76.09, 65.06, 64.50, 64.45, 49.05, 48.97, 48.79, 46.43, 46.13, 42.76, 42.03, 41.30, 39.84, 35.49, 35.34, 35.15, 29.82, 29.80, 29.75, 29.11, 28.00, 27.84, 27.68, 23.56, 23.08, 22.95, 19.79, 12.87; HRFAB-MS (thioglycerol+$Na^+$ matrix) m/e: ([M+Na]$^+$) 634.4167 (90.6%), calcd. 634.4169.

Compound 108: Compound 130 (0.105 g, 0.172 mmol) was dissolved in $CH_2Cl_2$ (5 mL) and MeOH (5 mL) at −78° C. $O_3$ was bubbled into the solution for ca. 20 min. $Me_2S$ (1 mL) was added followed, and the solvent was removed in vacuo. The residue was dissolved in THF (15 mL), and $LiAlH_4$ (0.033 g, 0.86 mmol) was added. The suspension was stirred for 12 hr. $Na_2SO_4 \cdot 10H_2O$ (about 2 g) was carefully added. After the gray color of the suspension dissipated, anhydrous $Na_2SO_4$ was added and the precipitate was removed by filtration. Concentration and silica gel chromatography ($CH_2Cl_2$/MeOH/28% $NH_3 \cdot H_2O$ 10:5:1.5 then 9:6:1.8) yielded a white glass. To this material was added 1 M HCl (4 mL). The resulting clear solution was washed with $Et_2O$ (3×10 mL). 20% NaOH solution was added to the aqueous phase until the solution became strongly basic. $CH_2Cl_2$ (4×10 mL) was used to extract the basic solution. The combined extracts were dried over anhydrous $Na_2SO_4$ and removal of solvent gave the desired product (0.063 g, 68% yield) as a colorless oil. $^1$H NMR (about 10% $CD_3OD$ in $CDCl_3$, 500 MHz) δ 4.76 (bs, 7 H), 3.75-3.71 (m, 1 H), 3.66-3.62 (m, 1 H), 3.58-3.52 (m, 4 H), 3.33-3.29 (m, 2 H), 3.22 (dd, J=10.5 and 7.6 Hz, 1 H), 3.15-3.09 (m, 2 H), 2.81 (t, J=6.8 Hz, 2 H), 2.76-2.71 (m, 4 H), 2.19-2.08 (m, 3 H), 2.00-1.66 (series of multiplets, 14 H), 1.58-1.45 (m, 3 H), 1.40-1.08 (m, 5 H), 1.03 (d, J=6.8 Hz, 3 H), 1.02-0.96 (m, 1 H), 0.93 (s, 3 H), 0.72 (s, 3 H); $^{13}$C NMR (about 10% $CD_3OD$ in $CDCl_3$, 75 MHz) δ 81.74, 80.64, 77.23, 67.95, 67.87, 67.18, 47.32, 44.59, 43.72, 43.01, 41.26, 40.80, 40.71, 40.23, 40.02, 36.36, 36.20, 35.87, 34.27, 33.99, 33.90, 29.60, 29.05, 28.58, 28.08, 24.49, 23.62, 23.46, 16.84, 13.12; HRFAB-MS (thioglycerol+$Na^+$ matrix) m/e: ([M+H]$^+$) 538.4578 (4.7%), calcd. 538.4584.

Example 11

This example includes a description of one or more exemplary synthetic procedures for obtaining Compounds CSA-21, 133-134 and CSA-15.

Compound CSA-21: Compound 115 (0.118 g, 0.183 mmol) was dissolved in dry $CH_2Cl_2$ (10 mL), and $SO_3$ pyridine complex (0.035 g, 0.22 mmol) was added. The suspension was stirred for 12 hr. The solvent was removed in vacuo to give white powder. To the white powder was added 1 M HCl (10 mL) and the resulting mixture was extracted with $CH_2Cl_2$ (4×10 mL). The combined extracts were dried over anhydrous $Na_2SO_4$. The desired product (0.11 g, 84%) was obtained as a pale yellow oil after silica gel chromatography (10% MeOH in $CH_2Cl_2$). $^1$H NMR (about 10% $CD_3OD$ in $CDCl_3$, 500 MHz) δ 4.03 (t, J=6.8 Hz, 2 H), 3.69-3.65 (m, 1 H), 3.62-3.58 (m, 1 H), 3.55 (t, J=6.1 Hz, 2 H), 3.51 (bs, 1 H), 3.46-3.38 (m, 6 H), 3.27 (d, J=2.4 Hz, 1 H), 3.26-3.21 (m, 1 H), 3.18-3.07 (m, 2 H), 2.18-2.03 (m, 3 H), 1.95-1.47 (series of multiplets, 19 H), 1.40-0.96 (series of multiplets, 9 H), 0.92 (d, J=6.8 Hz, 3 H), 0.91 (s, 3 H), 0.66 (s, 3 H); $^{13}$C NMR (about 10% $CD_3OD$ in $CDCl_3$, 75 MHz) δ 80.43, 79.68, 75.87, 69.30, 64.82, 64.32, 64.14, 48.78, 48.73, 48.50, 46.44, 46.21, 42.49, 41.76, 39.61, 35.36, 35.17, 35.06, 34.85, 31.73, 29.53, 29.46, 29.44, 28.84, 27.68, 27.48, 27.38, 25.91, 23.30, 22.75, 22.66, 17.70, 1232; HRFAB-MS (thioglycerol+$Na^+$ matrix) m/e: ([M−H+2Na]$^+$) 768.3831 (100%), calcd. 768.3843. The azides were reduced by treating the triazide (0.11 g, 0.15 mmol) with $Ph_3P$ (0.20 g, 0.77 mmol) in THF (10 mL) and $H_2O$ (1 mL). The mixture was stirred for 3 days. The solvent was removed in vacuo, and the residue was purified by silica gel chromatography ($CH_2Cl_2$/MeOH/28% $NH_3 \cdot H_2O$ 12:6:1 then 10:5:1.5) to afford the desired product (0.077 g, 78% yield) as a glass. HCl in $Et_2O$ (1 M, 0.5 mL) was added to the glass to give the corresponding HCl salt. $^1$H NMR (about 10% CDCl3 in $CD_3OD$, 500 MHz) δ 4.81 (s, 10 H), 4.07-3.97 (m, 2 H), 3.82 (bs, 1H), 3.71 (bs, 1 H), 3.65 (t, J=5.2 Hz, 2 H), 3.57 (bs, 1 H), 3.37-3.30 (m, 2 H), 3.22-3.02 (m, 8 H), 2.12-1.71 (series of multiplets, 17 H), 1.65-1.01 (series of multiplets, 13 H), 0.97 (d, J=6.8 Hz, 3 H), 0.94 (s, 3 H), 0.73 (s, 3 H); $^{13}$C NMR (about 10% $CDCl_3$ in $CD_3OD$, 75 MHz) δ 81.89, 80.58, 77.50, 70.04, 66.71, 66.56, 66.02, 47.11, 46.76, 44.20, 42.66, 40.50, 39.60, 39.40, 36.24, 36.11, 35.89, 35.67, 32.28, 29.38, 29.23, 29.10, 28.94, 28.49, 26.06, 24.21, 23.46, 23.30, 18.50, 12.86; HRFAB-MS (thioglycerol+$Na^+$ matrix) m/e: ([M+Na]$^+$) 668.4271 (100%), calcd. 668.4258.

Compound CSA-13: The mesylate derived from 23 (0.19 g, 0.264 mmol) was stirred with excess octyl amine (2 mL) at 80° C. for 12 hr. After removal of octylamine in vacuo, the residue was chromatographed (silica gel, EtOAc/hexanes 1:4 with 2% $Et_3N$) to afford the desired product (0.19 g, 95% yield) as a pale yellow oil. $^1$H NMR ($CDCl_3$, 300 MHz) δ 3.69-3.37 (series of multiplets, 11 H), 3.26-3.00 (m, 4 H), 2.61-2.53 (m, 4 H), 2.20-2.02 (m, 3 H), 1.98-0.99 (series of multiplets, 40 H), 0.92-0.85 (m, 9 H), 0.65 (s, 3H); $^{13}$C NMR ($CDCl_3$, 75 MHz) δ 80.60, 79.74, 76.05, 64.97, 64.40, 64.28, 50.79, 50.25, 49.00, 48.90, 48.71, 46.47, 46.34, 42.65, 41.96, 39.80, 35.77, 35.41, 35.27, 35.05, 33.73, 31.96, 30.25, 29.76, 29.74, 29.67, 29.39, 29.05, 27.84, 27.61, 27.55, 26.70, 23.50, 23.00, 22.82, 22.79, 18.06, 14.23, 12.54; HRFAB-MS (thioglycerol+$Na^+$ matrix) m/e: ([M+H]$^+$) 755.6012 (100%), calcd. 755.6024. The triazide (0.18 g, 0.239 mmol) was dissolved in THF (10 mL) and EtOH (10 mL). Lindlar catalyst (44 mg) was added, and the suspension was shaken under $H_2$ (50 psi) for 12 hr. After removal of the solvent in vacuo, the residue was purified by silica gel chromatography ($CH_2Cl_2$/MeOH/28% $NH_3 \cdot H_2O$ 10:5:1, then 10:5:1.5). To the product, 1 M HCl (2 mL) and the resulting clear solution was extracted with $Et_2O$ (2×10 mL). 20% NaOH solution was added until the solution became strongly basic. CH$_2$Cl$_2$ (20 mL, 2×10 mL) was used to extract the basic solution. The combined extracts were dried over anhydrous Na$_2$SO$_4$, and removal of solvent in vacuo gave the desired product (0.114 g, 68% yield) as a clear oil. $^1$H NMR (about 20% CDCl$_3$ in CD$_3$OD, 500 MHz) δ 4.79 (bs, 7 H), 3.74-3.70 (m, 1 H), 3.66-3.61 (m, 1 H), 3.56-3.51 (m, 3 H), 3.31-3.29 (m, 2 H), 3.16-3.09 (m, 2 H), 2.88-2.72 (m, 6 H), 2.59-2.51 (m, 4 H), 2.18-2.07 (m, 3 H), 1.97-1.66 (series of multiplets, 14 H), 1.62-0.97 (series of multiplets, 25 H), 0.95 (d, J=6.3 Hz, 3 H), 0.93 (s, 3 H), 0.89 (t, J=6.8 Hz, 3 H), 0.70 (s, 3 H); $^{13}$C NMR (about 20% CDCl$_3$ in CD$_3$OD, 75 MHz) δ 81.82, 80.63, 77.23, 67.85, 67.19, 51.20, 50.69, 47.82, 47.24, 43.92, 43.01, 41.30, 40.80, 40.68, 40.22 36.74, 36.38, 36.20, 35.87, 34.66, 34.15, 33.87, 32.90, 30.54, 30.39, 30.30, 29.64, 29.03, 28.59, 28.41, 26.96, 24.37, 23.65, 23.48, 18.75, 14.63, 13.09; HRFAB-MS (thioglycerol+Na$^+$ matrix) m/e: ([M+H]$^+$) 677.6309 (46.6%), calcd. 677.6309.

Compound CSA-46: Compound CSA-46 was prepared using the methods of CSA-13, substituting 7-deoxycholic steroid backbone precursor in place of cholic acid.

Compound 134: Compound CSA-13 (0.08 g, 0.12 mmol) was dissolved in CHCl$_3$ (5 mL) and MeOH (5 mL), aminoiminosulfonic acid (0.045 g, 0.36 mmol) was added, and the suspension was stirred for 12 hr. The solvent was removed in vacuo, and the residue was dissolved in 1 M HCl (6 mL) and H$_2$O (10 mL). The solution was washed with Et$_2$O (3×5 mL), and 20% NaOH solution was then added dropwise until the solution became strongly basic. The basic mixture was extracted with CH$_2$Cl$_2$ (4×5 mL). The combined extracts were dried over anhydrous Na$_2$SO$_4$ and concentrated in vacuo to give the desired product (0.087 g, 91% yield) as a white glass. $^1$H NMR (about 20% CDCl$_3$ in CD$_3$OD, 500 MHz) δ 4.96 (bs, 13 H), 3.74-3.68 (m, 1 H), 3.65-3.50 (m, 4 H), 3.38-3.18 (series of multiplets, 10 H), 2.60-2.50 (m, 4 H), 2.15-1.99 (m, 3 H), 1.88-1.72 (m, 14 H), 1.60-0.99 (series of multiplets, 25 H), 0.94 (bs, 6 H), 0.89 (t, J=6.6 Hz, 3 H), 0.71 (s, 3 H); $^{13}$C NMR (about 20% CDCl$_3$ in CD$_3$OD, 75 MHz) δ 159.00, 158.87, 158.72, 81.68, 79.93, 76.95, 66.59, 65.93, 65.45, 50.82, 50.40, 47.64, 46.94, 43.67, 42.27, 40.18, 39.25, 36.19, 35.66, 35.40, 34.21, 32.45, 30.51, 30.26, 30.18, 30.10, 29.86, 29.35, 28.71, 28.15, 28.00, 26.87, 23.94, 23.44, 23.23, 23.12, 18.61, 14.42, 12.98; HRFAB-MS (thioglycerol+Na$^+$ matrix) m/e: ([M+H]$^+$) 803.6958 (18.4%), calcd. 803.6953.

Compound CSA-15: The mesylate derived from 23 (0.092 g, 0.128 mmol) was dissolved in DMSO (2 mL) followed by the addition of NaN$_3$ (0.0167 g, 0.256 mmol). The suspension was heated to 70° C. for 12 hr. H$_2$O (20 mL) was added to the cooled suspension, and the mixture was extracted with EtOAc/hexanes (1:1) (20 mL, 3×10 mL). The combined extracts were washed with brine (30 mL), dried over anhydrous Na$_2$SO$_4$, and concentrated in vacuo to give the product (0.081 g, 95% yield) as a pale yellow oil. $^1$H NMR (CDCl$_3$, 300 MHz) δ 3.69-3.36 (m, 11 H), 3.25-3.02 (m, 6 H), 2.20-2.02 (m, 3 H), 1.97-1.60 (m, 15 H), 1.55-0.98 (m, 13 H), 0.92 (d, J=6.3 Hz. 3 H), 0.89 (s, 3 H ), 0.66 (s, 3 H); $^{13}$C NMR (CDCl$_3$, 75 MHz) δ 80.59, 79.77, 76.03, 65.01, 64.46, 64.30, 52.12, 48.99, 48.95, 48.76, 46.44, 46.42, 42.70, 41.99, 39.82, 35.56, 35.44, 35.31, 35.09, 33.09, 29.79, 29.77, 29.71, 29.08, 27.88, 27.78, 27.66, 25.65, 23.53, 23.03, 22.85, 18.00, 12.58; HRFAB-MS (thioglycerol+Na$^+$ matrix) m/e: ([M+Na]$^+$) 691.4512 (100%), calcd. 691.4496. The tetraazide (0.081 g, 0.12 mmol) was dissolved in THF (5 mL) and EtOH (10 mL). Lindlar catalyst (30 mg) was added, and the suspension was shaken under H$_2$ (50 psi) for 12 hr. After removal of the solvent in vacuo, the residue was purified by silica gel chromatography (CH$_2$Cl$_2$/MeOH/28% NH$_3$.H$_2$O 5:3:1, then 2:2:1). To the product, 1M HCl (2 mL) was added, and the resulting solution was washed with Et$_2$O (2×10 mL). 20% NaOH solution was added to the aqueous phase until the solution became strongly basic. CH$_2$Cl$_2$ (10 mL, 2×5 mL) was used to extract the basic solution. The combined extracts were dried over anhydrous Na$_2$SO$_4$, and concentration in vacuo gave the desired product (0.044 g, 64% yield) as a colorless oil. $^1$H NMR (about 20% CDCl$_3$ in CD$_3$OD, 500 MHz) δ 4.79 (bs, 8 H), 3.74-3.70 (m, 1H), 3.66-3.62 (m, 1 H), 3.56-3.52 (m, 3 H), 3.31-3.27 (m, 2 H), 3.16-3.10 (m, 2 H), 2.82-2.70 (m, 6 H), 2.64-2.54 (m, 2 H), 2.19-2.07 (m, 3 H), 1.99-1.66 (series of multiplets, 14 H), 1.58-0.96 (series of multiplets, 13 H), 0.96 (d, J=6.6 Hz, 3 H), 0.93 (s, 3 H), 0.70 (s, 3 H); $^{13}$C NMR (about 20% CDCl$_3$ in CD$_3$OD, 75 MHz) δ 81.96, 90.76, 77.33, 67.92, 67.26, 47.84, 47.33, 44.04, 43.24, 43.15, 41.40, 40.91, 40.78, 40.29, 36.82, 36.48, 36.28, 35.96, 34.39, 34.11, 30.59, 29.69, 29.13, 28.68, 28.64, 24.43, 23.69, 23.48, 18.77, 13.06; HRFAB-MS (thioglycerol+Na$^+$ matrix) m/e: ([M+H]$^+$) 565.5041 (100%), calcd. 565.5057.

Example 12

This example includes a description of one or more exemplary synthestic procedures for obtaining Compounds 203a-b, 207a-c, 209a-c, 210a-b and CSA-31.

Compounds 203a-b, 207a-c, 208a-c, 209a-c, and 210a-b: BOC-glycine was reacted with DCC, DMAP and cholic acid derivative 201 (Scheme 11) to give triester 202a in good yield. A similar reaction incorporating BOC-β-alanine was also successful, giving 202b. Deprotection of 202a and 202b with HCl in dioxane, followed by purification (SiO$_2$ chromatography with a CH$_2$Cl$_2$ MeOH/NH$_4$OH eluent), gave triesters 203a and 203b in good yield.

Triamides of glycine and β-alanine (207a and 207b, respectively) were formed using the same reaction conditions (Scheme 12). Triamides with α-branched amino acids could also be formed. For example, under the conditions described, a triamide with bis-BOC-lysine side chains was formed (compound 207c). The C24 esters of 207a-c were hydrolyzed with LiOH in THF and methanol to give alcohols 208a-c. Deprotection using HCl in dioxane (208a-c) gave triamides 209a-c in good yield. In addition, alcohols 208a and 208b were mesylated and reacted with benzylmethyl amine. Deprotection of the resulting compounds with HCl in dioxane gave triamides 210a and 210b (Scheme 12). Compound CSA-31 was prepared by analogy to compounds 210a and 210b.

Example 13

This example includes a description of one or more exemplary synthetic procedures for obtaining Compounds 302, 312-321, 324-326, 328-331 and 341-343.

Compound 302: Compound 308 (5β-cholanic acid 3,7,12-trione methyl ester) was prepared from methyl cholate and pyridinium dichromate in near quantitative yield from methyl cholate. Compound 308 can also be prepared as described in Pearson et al., J. Chem. Soc. Perkins Trans. 1 1985, 267; Mitra et al., J. Org. Chem. 1968, 33, 175; and Takeda et al., J. Biochem. (Tokyo) 1959, 46, 1313. Compound 308 was treated with hydroxyl amine hydrochloride and sodium acetate in refluxing ethanol for 12 hr (as described in Hsieh et al., Bioorg. Med. Chem. 1995, 3, 823), giving 309 in 97% yield.

A 250 ml three neck flask was charged with glyme (100 ml); to this was added 309 (1.00 g, 2.16 mmol) and sodium borohydride (2.11 g, 55.7 mmol). TiCl$_4$ (4.0 mL, 36.4 mmol) was added to the mixture slowly under nitrogen at 0° C. The resulting green mixture was stirred at room temperature for 24 hours and then refluxed for another 12 h. The flask was cooled in an ice bath, and ammonium hydroxide (100 mL) was added. The resulting mixture was stirred for 6 hours at room temperature. Conc. HCl (60 mL) was added slowly, and the acidic mixture was stirred for 8 hours. The resulting suspension was made alkaline by adding solid KOH. The suspension was filtered and the solids were washed with MeOH. The combined filtrate and washings were combined and concentrated in vacuo. The resulting solid was suspended in 6% aqueous KOH (100 mL) and extracted with CH$_2$Cl$_2$ (4×75 mL). The combined extracts were dried over Na$_2$SO$_4$ and solvent was removed in vacuo to give 1.14 g of a white solid. The mixture was chromatographed on silica gel (CH$_2$Cl$_2$/MeOH/NH$_4$OH 12:6:1) giving 302 (0.282 g, 33% yield), 3 (0.066 g, 8% yield), 4 (0.118 g, 14% yield).

Compound 302: m.p. 200-202° C.; $^1$H NMR (about 10% CDCl$_3$ in CD$_3$OD, 300 MHz) δ 4.81 (bs, 7 H), 3.57-3.49 (m, 2 H), 3.14 (t, J=3.2 Hz, 1 H), 2.97 (bs, 1 H), 2.55-2.50 (m, 1 H), 2.15-2.10 (m, 1 H), 1.95-1.83 (m, 3 H), 1.74-0.99 (series of multiplets, 20 H), 1.01 (d, J.6.4 Hz, 3 H), 0.95 (s, 3 H), 0.79 (s, 3 H); $^{13}$C NMR (10% CDCl$_3$ in CD$_3$OD, 75 MHz) δ 63.28, 55.01, 52.39, 49.20, 48.69, 47.00, 43.24, 42.77, 41.03, 40.27, 36.82, 36.35, 35.75, 35.12, 32.77, 31.36, 30.10, 28.54, 27.88, 26.96, 24.35, 23.38, 18.18, 14.23, HRFAB-MS (thioglycerol+Na$^+$ matrix) m/e: ([M+H]$^+$) 392.3627 (100%); calcd. 392.3641.

Octanyl cholate (328): Cholic acid (3.14 g, 7.43 mmol) and 10-camphorsulfonic acid (0.52 g, 2.23 mmol) were dissolved in octanol (3.5 mL, 23.44 mmol). The solution was warmed to 40-50° C. in oil bath under vacuum (about 13 mm/Hg). After 14 h, the remaining octanol was evaporated under high vacuum. The crude product was purified via chromatography (silica gel, 5% MeOH in CH$_2$Cl$_2$) to afford the desired product (2.81 g, 73% yield) as a white powder. $^1$H NMR (CDCl$_3$, 500 MHz) δ 4.06 (t, J=6.7 Hz, 2 H), 3.98 (s, 1 H), 3.86 (s, 1 H), 3.48-3.44 (m, 1 H), 2.41-2.34 (m, 1 H), 2.28-2.18 (m, 3 H), 1.98-1.28 (series of multiplets, 35 H), 0.99 (d, J=3.3 Hz, 3 H), 0.90 (s, 3 H), 0.89 (t, J=7 Hz, 3 H), 0.69 (s, 3 H); $^{13}$C NMR (CDCl$_3$, 75 MHz) δ 154.38, 73.18, 72.14, 68.63, 56.07, 50.02, 49.32, 47.07, 46.74, 41.96, 41.67, 39.84, 39.76, 35.66, 35.45, 34.95, 34.86, 34.15, 32.97, 32.91, 31.65, 31.11, 30.68, 28.39, 27.78, 26.66, 26.52, 25.82, 25.70, 25.54, 25.15, 24.95, 23.45, 22.69, 17.77, 12.71; HRFAB-MS (thioglycerol+Na$^+$ matrix) m/e: ([M+Na]$^+$) 543.4015 (100%), calcd. 543.4026.

Representative synthesis of compounds 329-331: Octanyl cholate (328) (0.266 g, 0.511 mmol), N-t-Boc-glycine (0.403 g, 2.298 mmol), DCC (0.474 g, 2.298 mmol) and DMAP (0.0624 g, 0.051 mmol) were mixed in CH$_2$Cl$_2$ (15 mL) for 3 h. The resulting white precipitate was removed by filtration. The filtrate was concentrated, and the product was purified by chromatography (silica gel, EtOAc/Hexane 1:2) to afford the desired product (0.481 g, 95% yield) as a white powder. Compound 329 $^1$H NMR (CDCl$_3$, 300 MHz) δ 5.18 (br, 3 H), 5.01 (s, 1 H), 4.61 (m, 1 H), 4.04 (t, J=6.5 Hz, 2 H), 3.97-3.88 (series of multiplets, 6 H), 2.39-2.15 (series of multiplets, 2 H), 2.06-1.02 (series of multiplets, 35 H), 1.46 (s, 18 H), 1.45 (s, 9 H), 0.93 (s, 3 H), 0.88 (t, J=6.7 Hz, 3 H), 0.81 (d, J=6 Hz, 3 H), 0.74 (s, 3 H); $^{13}$C NMR (CDCl$_3$, 75 MHz) δ 174.26, 170.19, 169.9, 169.78, 155.87, 155.67, 79.95, 76.47, 75.167, 72.11, 64.55, 47.40, 45.28, 43.17, 42.86, 40.82, 37.94, 34.71, 34.63, 34.43, 31.86, 31.340, 31.20, 30.76, 29.29, 29.25, 28.80, 28.72, 28.42, 28.06, 27.96, 27.19, 26.81, 26.29, 26.012, 25.66, 22.87, 22.71, 22.57, 17.55, 14.18, 12.27; HRFAB-MS (thioglycerol+Na$^+$ matrix) m/e: ([M+Na]$^+$) 1014.6261 (100%), calcd. 1014.6242. Compound 330: $^1$H NMR (CDCl$_3$, 500 MHz) δ 5.10 (s, 1 H), 4.92 (d, J=2.44 Hz, 1 H), 4.55 (m, 1 H), 4.00 (t, J=6.8 Hz, 2 H), 3.39-3.33 (series of multiplets, 6 H), 2.595-2.467 (series of multiplets, 6 H), 2.31-2.12 (series of multiplets, 2 H), 2.01-1.00 (series of multiplets, 37 H), 1.39 (s, 27 H), 0.88 (s, 3 H), 0.84 (t, J=6.8 Hz, 3 H), 0.76 (d, J=6.3 Hz, 3 H), 0.69 (s, 3 H); $^{13}$C NMR (CDCl$_3$, 75 MHz) δ 174.16, 172.10, 171.78, 171.67, 155.95, 79.45, 75.67, 74.21, 71.10, 64.63, 47.79, 45.27, 43.52, 40.97, 37.92, 36.35, 35.14, 35.05, 34.90, 34.71, 34.46, 31.91, 31.45, 30.95, 29.35, 29.31, 28.96, 28.78, 28.56, 28.55, 27.22, 26.98, 26.269, 25.71, 23.00, 22.77, 22.64, 17.75, 14.24, 12.39; HRFAB-MS (thioglycerol+Na$^+$ matrix) m/e: ([M+Na]$^+$) 1056.6702 (100%), calcd. 1056.6712. Compound 331 $^{13}$C NMR (CDCl$_3$, 125 MHz) δ 174.00, 172.75, 172.41, 172.30, 156.03, 79.00, 75.28, 73.79, 70.77, 64.39, 47.43, 45.04, 43.21, 40.76, 40.00, 39.93, 37.78, 34.74, 34.62, 34.23, 32.19, 32.01, 31.70, 31.24, 30.77, 29.13, 29.10, 28.67, 38.58, 28.38, 25.86, 25.37, 22.56, 22.38, 17.51, 14.05, 12.13; HRFAB-MS (thioglycerol+Na$^+$ matrix) m/e: ([M+Na]$^+$) 1098.7181 (100%), calcd. 1098.7181.

Representative synthesis of compounds 341-343: To compound 329 (0.463 g, 0.467 mmol) was added HCl in dioxane (0.3 mL, 4.0 M). After stirring the mixture for 30 min, the excess HCl and solvent were removed in vacuo. The product was isolated, after chromatography (silica gel, CH$_2$Cl$_2$/MeOH/NH$_3$.H$_2$O 10:1.2:0.1) as a (0.271 g, 84%) pale oil. The trihydrochloride salt of 341 was prepared by addition of HCl in dioxane and evaporation of excess HCl and dioxane in vacuo giving a white powder. Compound 341: $^1$HNMR (CDCl$_3$ with about 10% CD$_3$OD, 500 MHz) δ 5.16 (s, 1 H), 4.99 (t, J=3.6 Hz, 1 H), 4.61 (m, 1 H), 4.04 (t, J=6.8 Hz, 2 H), 3.51-3.36 (m, 6 H), 2.34-2.15 (m, 2 H), 2.00-1.05 (series of multiplets, 40 H), 0.93 (s, 3 H), 0.88 (t, J=7.1 Hz, 3 H), 0.80 (d, J=3.2 Hz, 3 H), 0.74 (s, 3 H); $^{13}$C NMR (CDCl$_3$ and about 10% CD$_3$OD, 75 MHz) δ 174.32, 173.92, 173.81, 76.08, 74.67, 71.61, 64.73, 47.64, 45.39, 44.41, 43.49, 40.97, 37.99, 34.99, 34.77, 34.71, 34.52, 31.96, 31.54, 31.35, 30.96, 29.39, 29.36, 29.02, 28.82, 27.32, 27.11, 26.11, 25.83, 23.01, 22.82, 22.69, 17.79, 14.28, 12.41; HRFAB-MS (thioglycerol+Na$^+$ matrix) m/e: ([M+Na]$^+$) 714.4651 (100%), calcd. 714.4669. Compound 342: $^1$H NMR (CDCl$_3$ and about 10% CD$_3$OD, 300 MHz) δ 5.142 (s, 1 H), 4.96 (d, J=2.7 Hz, 1 H), 4.60, (m, 1 H), 4.04 (t, J=6.6 Hz, 2 H), 3.07-2.95 (series of multiplets, 6 H), 2.56-2.43 (series of multiplets, 6 H), 2.38-2.13 (series of multiplets, 2 H), 2.07-1.02 (series of multiplets, 36 H), 0.92 (s, 3 H), 0.88 (t, J=6.6 Hz, 3 H), 0.82 (d, J=6.6 Hz, 3 H), 0.73 (s, 3 H); $^{13}$C NMR (CDCl$_3$ and CD$_3$OD, 75 MHz) δ 174.29, 172.29, 171.98, 171.92, 75.52, 74.09, 70.98, 64.67, 47.78, 45.26, 43.52, 40.98, 38.73, 38.62, 38.35, 38.07, 38.03, 37.99, 35.01, 34.81, 34.77, 34.49, 31.92, 31.50, 31.40, 30.99, 29.36, 29.33, 28.93, 28.80, 27.43, 26.96, 26.08, 25.56, 23.07, 22.79, 22.62, 17.73, 14.25, 12.34; HRFAB-MS (thioglycerol+Na$^+$ matrix) m/e: ([M+Na]$^+$) 714.4651 (100%), calcd. 714.4669. Compound 343: $^1$H NMR (CDCl$_3$ and CD$_3$OD, 500 MHz) δ 5.12 (s, 1H) 4.93 (s, 1 H), 4.59 (m, 1 H), 4.04 (t, J=7 Hz, 2 H), 2.79-2.69 (series of multiplets, 6 H), 2.4621-2.2999 (series of multiplets, 6 H), 2.2033-1.0854 (series of multiplets, 42 H), 0.94 (s, 2 H), 0.91 (s, 1 H), 0.88 (t, J=7 Hz, 3 H), 0.82 (d, J=6.4 Hz, 3 H), 0.75 (s, 3 H); $^{13}$C NMR (CDCl$_3$ and CD$_3$OD, 75 MHz) δ 174.70, 171.97, 171.86, 171.75, 76.10, 74.55, 71.56, 64.85, 47.96, 45.31, 43.37, 40.87, 38.09, 34.86, 34.80, 34.73, 34.46, 32.84, 32.62, 32.27, 31.87, 31.75, 31.42, 31.08, 29.31, 29.28, 29.26, 28.78, 28.73, 27.38, 26.91, 26.05, 25.37, 23.24, 23.15, 22.95, 22.74, 22.71, 22.43, 17.78, 14.11, 12.28;

HRFAB-MS (thioglycerol+Na$^+$ matrix) m/e: ([M+Na]$^+$) 798.5624 (100%), calcd. 798.5609.

Benzyl cholate (312): Cholic acid (4.33 g, 10.62 mmol) and 10-caphorsulfonic acid (0.493 g, 2.21 mmol) were dissolved in benzyl alcohol (1.97 mL, 19.3 mmol). The suspension was heated to 50° C. in oil bath and stirred under vacuum (about 13 mm/Hg) for 16 h. Excess benzyl alcohol was removed in vacuo, and the crude product was chromatographed (silica gel, 5% MeOH in CH$_2$Cl$_2$) to give the desire product as a white powder (4.23 g, 81% yield). $^1$H NMR (CDCl$_3$, 500 MHz) δ 7.34-7.33 (m, 5 H), 5.10 (d, J=1.5 Hz, 2 H), 3.92 (s, 1 H), 3.81 (s, 1 H), 3.42 (s, 1 H), 3.40 (br, m, 3 H), 2.44-2.38 (m, 1 H), 2.31-2.25 (m, 1 H), 2.219 (t, J=12 Hz, 2 H), 0.96 (d, J=5.5 Hz, 3 H), 0.86 (s, 3 H), 0.63 (s, 3 H); $^{13}$C NMR (CDCl$_3$, 125 MHz) δ 174.25, 136.30, 128.66, 128.63, 128.32, 128.28, 128.24, 73.18, 71.98, 68.54, 66.18, 47.14, 46.56, 41.69, 39.65, 35.51, 35.37, 34.91, 34.84, 31.49, 31.08, 30.50, 28.31, 27.62, 26.47, 23.35, 22.65, 22.60, 17.42, 12.63, 12.57; HRFAB-MS (thioglycerol+Na$^+$ matrix) m/e: ([M+Na]$^+$) 521.3235 (100%), calcd. 521.3242.

Representative synthesis of compounds 313-315: Benzyl cholate (312) (0.248 g, 0.499 mmol), N-t-Boc-glycine (0.404 g, 2.30 mmol), DCC (0.338 g, 1.49 mmol) and DMAP (0.051 g, 0.399 mmol) were added to CH$_2$Cl$_2$ (15 mL), and the suspension was stirred for 16 h. The resulting white precipitate was removed by filtration, and the filtrate was concentrated. The product was obtained after chromatography (silica gel, EtOAc/Hexane 0.6:1) as a white powder (0.329 g, 68%). Compound 313: $^1$H NMR (CDCl$_3$, 300 MHz) δ 7.34-7.33 (m, 5 H), 5.16 (s, 1 H), 5.08 (dd, J=22.5 Hz, 12.3 Hz, 4 H), 5.00 (s, 1 H), 4.60 (m, 1 H), 4.04-3.81 (series of multiplets, 6 H), 2.43-1.01 (series of multiplets, 25 H), 1.46 (s, 9 H), 1.44 (s, 18 H), 0.92 (s, 3 H), 0.797 (d, J=5.7 Hz, 3 H), 0.69 (s, 1 H); $^{13}$C NMR (CDCl$_3$, 75 MHz) δ 173.99, 170.25, 170.05, 169.85, 155.73, 136.19, 128.69, 128.45, 128.35, 80.06, 77.65, 77.23, 76.80, 76.53, 75.24, 72.19, 66.29, 47.46, 45.35, 43.24, 42.91, 40.89, 38.00, 34.79, 34.66, 34.49, 31.43, 31.25, 30.77, 28.88, 28.40, 27.23, 26.89, 25.74, 22.94, 22.65, 17.61, 12.32; FAB-MS (thioglycerol+Na$^+$ matrix) m/e: ([M+Na]$^+$) 992.5468 (100%), calcd. 992.5460.

Representative synthesis of compounds 316-318: Compound 313 (0.505 g, 0.520 mmol) and Pd (5 wt. % on active carbon, 0.111 g, 0.0521 mmol) were added to MeOH (5 mL). The suspension was stirred under H$_2$ (50 psi) for 20 hours. The solids were removed by filtration and the filtrate was concentrated. Purification of the product via chromatography (silica gel, 5% MeOH in CH$_2$Cl$_2$) gave a white powder (0.450 g, 98% yield). Compound 316: $^1$H NMR (CDCl$_3$, 500 MHz) δ 5.20 (s, 1 H), 5.12 (br., 2 H), 4.92 (s, 1 H), 4.55 (m, 1 H), 3.98-3.83 (series of multiplets, 6 H), 2.30-2.13 (series of multiplets, 2 H), 1.96-0.98 (series of multiplets, 30 H), 1.40 (s, 9 H), 1.39 (s, 18 H), 0.87 (s, 3 H), 0.76 (d, J=6.3 Hz, 3 H), 0.68 (s, 3 H); $^{13}$C NMR (CDCl$_3$ 75 MHz) δ 174.11, 165.60, 165.41, 165.22, 151.28, 151.14, 75.48, 75.26, 71.81, 70.57, 67.50, 45.95, 42.58, 40.65, 38.52, 38.16, 36.17, 33.28, 30.01, 29.78, 26.71, 26.42, 25.95, 24.16, 23.78, 23.40, 23.31, 22.55, 22.16, 21.03, 18.23, 17.93, 12.91, 7.61; FAB-MS (thioglycerol+Na$^+$ matrix) m/e: ([M+Na]$^+$) 902.4997 (21%), calcd. 902.4990.

Representative synthesis of compounds 319-321: Compound 316 (0.375 g, 0.427 mmol), DCC (0.105 g, 0.512 mmol) and DMAP (0.062 g, 0.512 mmol) and N,N-dimethylethanolamine (0.09 ml, 0.896 mmol) were added to CH$_2$Cl$_2$ (15 mL). The mixture for 16 h, and solvent and excess N,N-dimethylethanolamine were removed in vacuo. The product was purified via chromatography (silica gel EtOAc/hexane/Et3N, 12:10:0.6) giving a white powder (0.330 g, 82% yield). $^1$H NMR (CDCl$_3$ and about 10% CD$_3$OD, 500 MHz) δ 5.18 (s, 1 H), 5.00 (s, 1 1-1), 4.19 (t, J=5.0 Hz, 2 H), 3.92 (s, 3 H), 3.81 (s, 3 H), 2.62 (t, J=10 Hz, 2 H), 2.30 (s, 6 H), 1.47 (s, 9 H), 1.47 (s, 1 H), 1.45 (s, 1 H), 2.12-1.05 (series of multiplets, 27 H), 0.96 (s, 3 H), 0.84 (d, J=10.5 Hz, 3 H), 0.78 (s, 3 H); $^{13}$C NMR (CDCl$_3$ and about 10% CD$_3$OD, 125 MHz) δ 174.19, 170.05, 169.87, 156.21, 79.36, 79.27, 76.06, 76.90, 71.80, 61.19, 57.04, 46.88, 44.87, 44.67, 44.53, 42.78, 42.15, 42.01, 40.43, 37.47, 34.32, 34.11, 33.92, 33.35, 33.25, 30.74, 30.56, 30.16, 28.40, 27.67, 27.62, 26.73, 26.19, 25.18, 25.10, 24.72, 24.49, 22.29, 21.81, 16.76, 11.56; FAB-MS (thioglycerol+Na$^+$ matrix) m/e: ([M+Na]$^+$) 973.5723 (100%), calcd. 973.5725. The white solid from the previous reaction (0.680 g, 0.714 mmol) and MeI (1 M in CH$_2$Cl$_2$, 1.5 mL) were stirred together for 2 h. The solvent and excess MeI were removed in vacuo giving a white solid (0.812 g about 100%). The product was carried on without further purification.

Representative synthesis of compounds 324-326: Compound 319 (0.812 g, 0.714 mmol) was dissolved in CH$_2$Cl$_2$ (5 mL) and trifluoroacetic acid (0.5 mL) was added. The mixture was stirred for 16 min. The solvent and excess acid were removed in vacuo, and the resulting oil was chromatographed (silica gel, CH$_2$Cl$_2$/MeOH/NH$_3$.H$_2$O 4:4:1) to give the desired product as a pale glass (0.437 g, 90% yield). Addition of HCl (2 M in ethyl ether, 2.5 mL) gave the trihydrochloride salt of 324 as a pale yellow powder. Compound 324: $^1$H NMR (50% CDCl$_3$, 50% CD$_3$OD, 300 MHz) δ 5.43 (s, 1 H), 5.24 (s, 1 H), 4.84 (m, 1 H), 4.66 (m, 2 H), 4.16-3.96 (series of multiplets, 6 H), 3.88 (m, 2 H), 3.37 (s, 9 H), 0.67 (s, 3 H), 0.59 (d, J=6.3 Hz, 3 H), 0.56 (s, 3 H); $^{13}$C NMR (50% CDCl$_3$, 50% CD$_3$OD, 75 MHz) □173.47, 167.06, 167.01, 166.70, 78.01, 76.49, 73.78, 64.98, 57.67, 53.36, 47.49, 46.99, 45.61, 43.28, 40.83, 40.23, 40.10, 37.69, 34.80, 34.48, 34.28, 31.03, 30.63, 30.44, 28.94, 27.05, 26.56, 25.50, 22.53, 21.56, 16.95, 11.37; FAB-MS (thioglycerol+Na$^+$ matrix) m/e: ([M-I]$^+$) 665.4475 (85.6%), cacld 665.4489. Compounds 325 and 326 proved too unstable to chromatograph using the basic eluent used for the purification of 324. Consequently, 325 and 326 were prepared by deprotection of 320 and 321 using HCl (2 M in diethyl ether), followed by tituration with ethyl acetate. The compounds were then used without further purification. $^1$H NMR spectroscopy indicated that compounds 325 and 326 were >95% pure. Compound 325: $^1$H NMR (50% CDCl$_3$, 50% CD$_3$OD, 500 MHz) δ 5.21 (s, 1 H), 5.02 (d, J=4 Hz, 1 H), 4.64 (m, 1 H), 4.53 (m, 2 H), 3.74 (m, 2 H), 3.31-3.01 (series of multiplets, 6 H), 3.23 (s, 9 H), 2.96-2.73 (series of multiples, 6 H), 2.51-2.44 (m, 1 H), 2.35-2.29 (m, 1 H), 2.14-1.09 (series of multiplets, 26 H), 0.99 (s, 3 H), 0.85 (d, J=6.5 Hz, 3 H), 0.80 (s, 3 H); $^{13}$C NMR (50% CDCl$_3$, 50% CD$_3$OD, 125 MHz) δ 172.77, 169.88, 169.56, 169.50, 75.94, 74.44, 71.57, 64.31, 56.94, 52.92, 46.78, 44.59, 42.70, 40.21, 37.16, 34.80, 34.72, 34.66, 34.05, 34.00, 33.78, 33.62, 30.95, 30.91, 30.81, 30.41, 29.96, 29.81, 28.20, 26.37, 26.06, 24.74, 24.24, 22.04, 21.13, 16.54, 10.97; FAB-MS (thioglycerol+Na$^+$ matrix) m/e: ([M-I]$^+$) 707.4958 (25.6%), cacld 707.4958. Compound 326: $^1$H NMR (50% CDCl$_3$, 50% CD$_3$OD, 500 MHz) δ 5.12 (s, 1H), 4.94 (d, J=2.5 Hz, 1 H), 4.56 (m. 1 H), 4.51 (t, J=2.3 Hz, 2 H), 3.74 (m, 2 H), 3.23 (s, 9 H), 3.05-3.01 (m, 4 H), 2.98 (t, J=7.5 Hz, 2 H), 2.63-2.43 (series of multiplets, 6 H), 2.31-2.24 (series of multiplets, 2 H), 2.07-1.87 (series of multiplets, 12 H), 1.17-1.05 (series of multiplets, 23 H), 0.94 (s, 3 H), 0.82 (d, J=6.0 Hz, 3 H), 0.76 (s, 3 H); $^{13}$C NMR (50% CDCl$_3$, 50% CD$_3$OD, 125 MHz) δ 171.87, 169.79, 169.59, 169.50, 76.12, 74.70, 71.65, 65.57, 65.08, 64.40, 57.68, 53.74, 52.78, 45.33, 43.54, 41.04, 39.12, 37.92, 43.85, 34.72, 34.56, 34.34, 32.30, 31.47, 31.27, 30.87, 30.58, 29.03, 27.053, 26.84, 25.51, 24.95, 24.91, 22.87, 22.82, 22.65, 21.93, 17.31, 11.81; FAB-MS (thioglycerol+Na⁺ matrix) m/e: ([M−I]⁺) 749.5432 (100%), cacld 749.5436.

Example 14

This example includes data indicating the stability of Compounds 352-354 under acidic, neutral and basic conditions.

Figure 9:
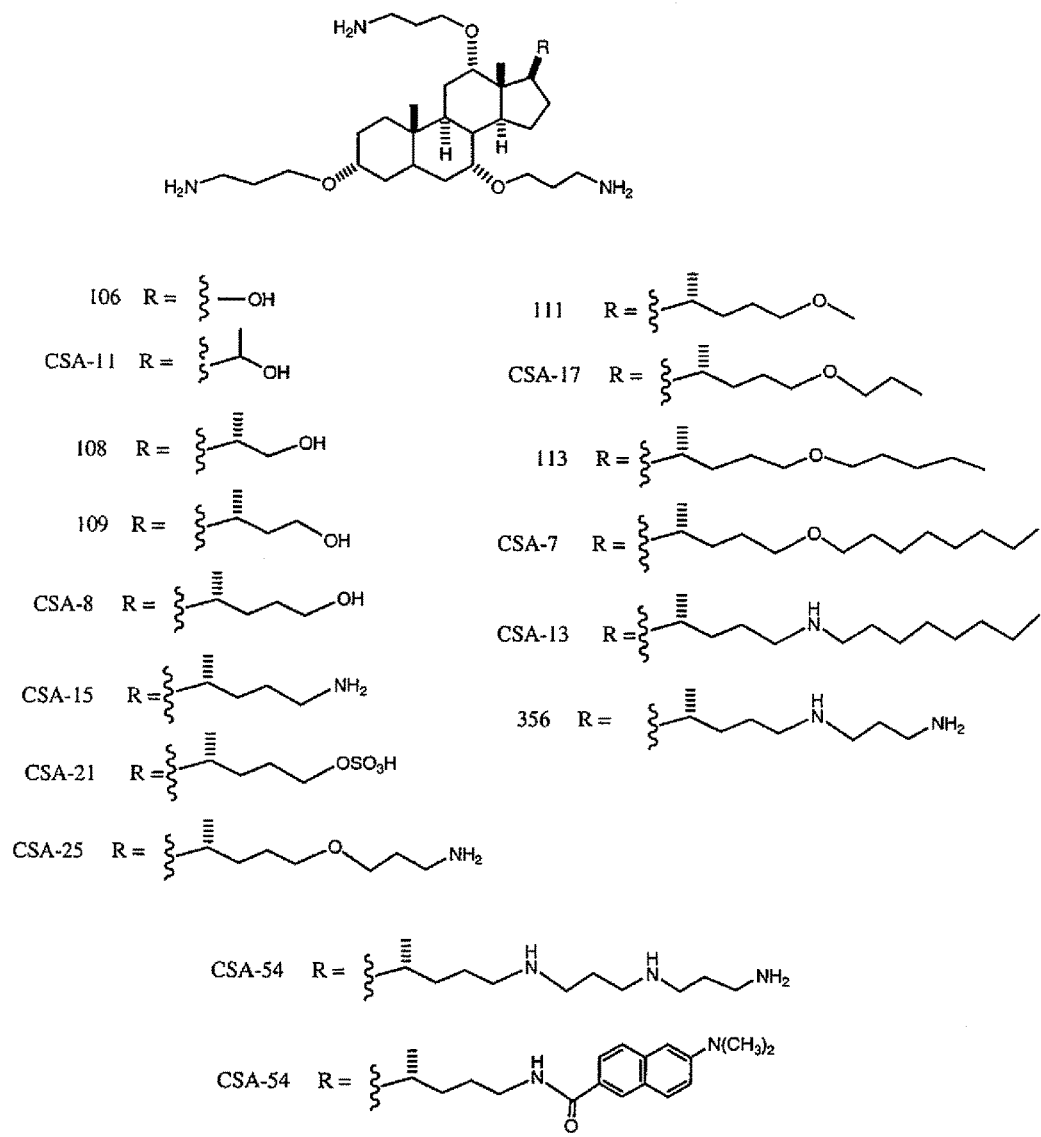
FIG. 9: shows structures of additional CSAs.
Figure 10:
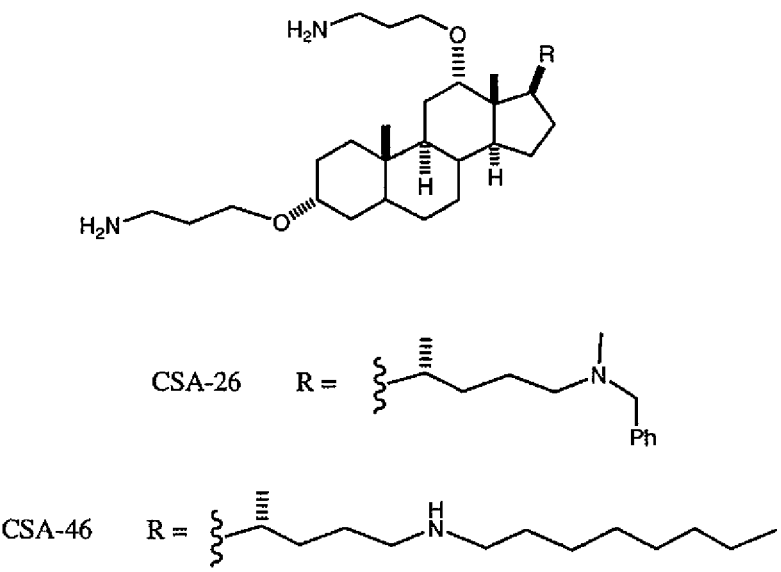
FIG. 10: shows structures of CSA-26 and CSA-46.
Figure 11:
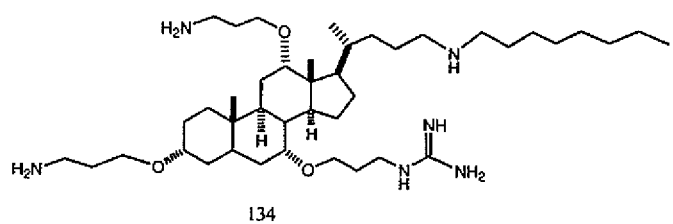
FIG. 11: shows structure of CSA-134.
Figure 12:
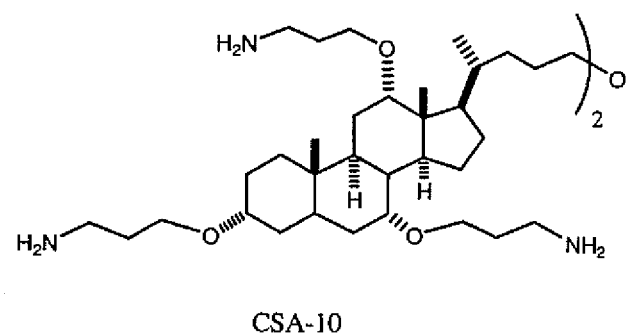
FIG. 12: shows structure of CSA-10.
Figure 13:
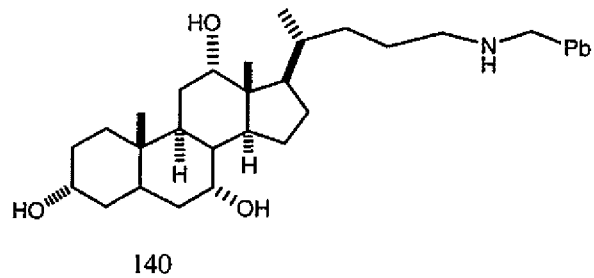
FIG. 13: shows structure of CSA-140.
Figure 14:
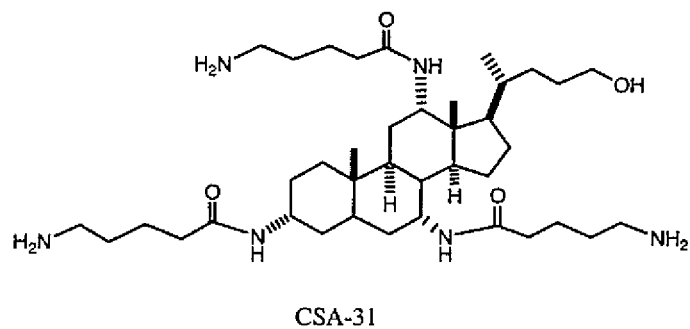
FIG. 14: shows structure of CSA-31.
Figure 15:
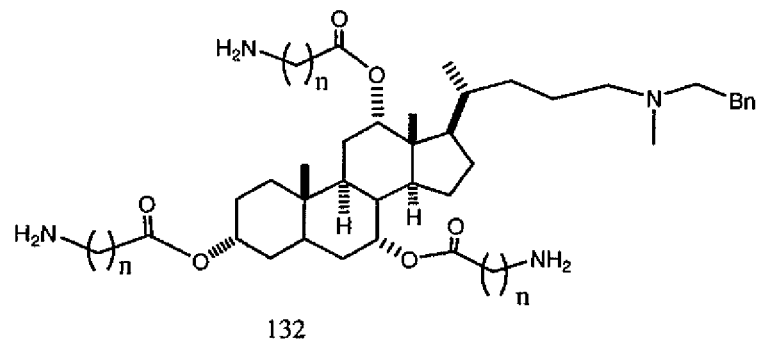
FIG. 15: shows structures of CSAs 352-354.
Figure 16:
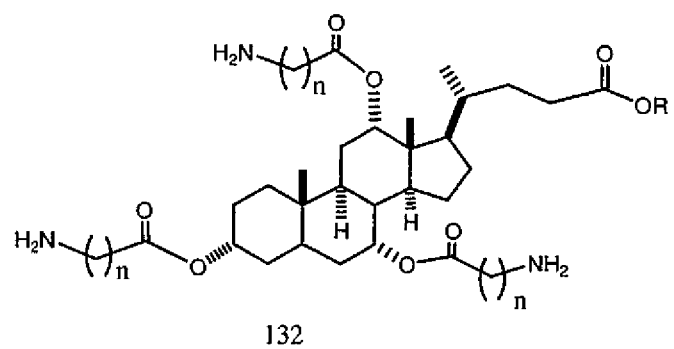
FIG. 16: shows structures of CSAs 341-343 and 324-327.
Figure 17:
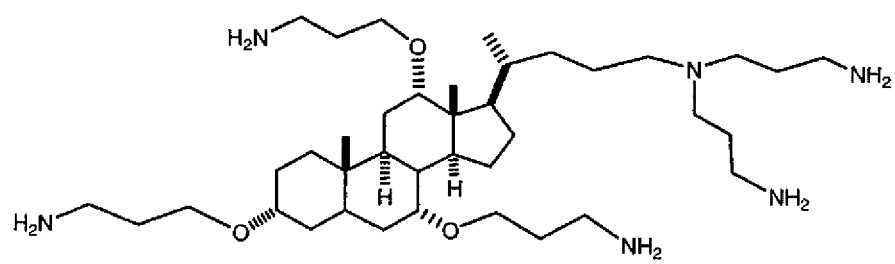
FIG. 17: shows structure of CSA-358.
Figure 18:
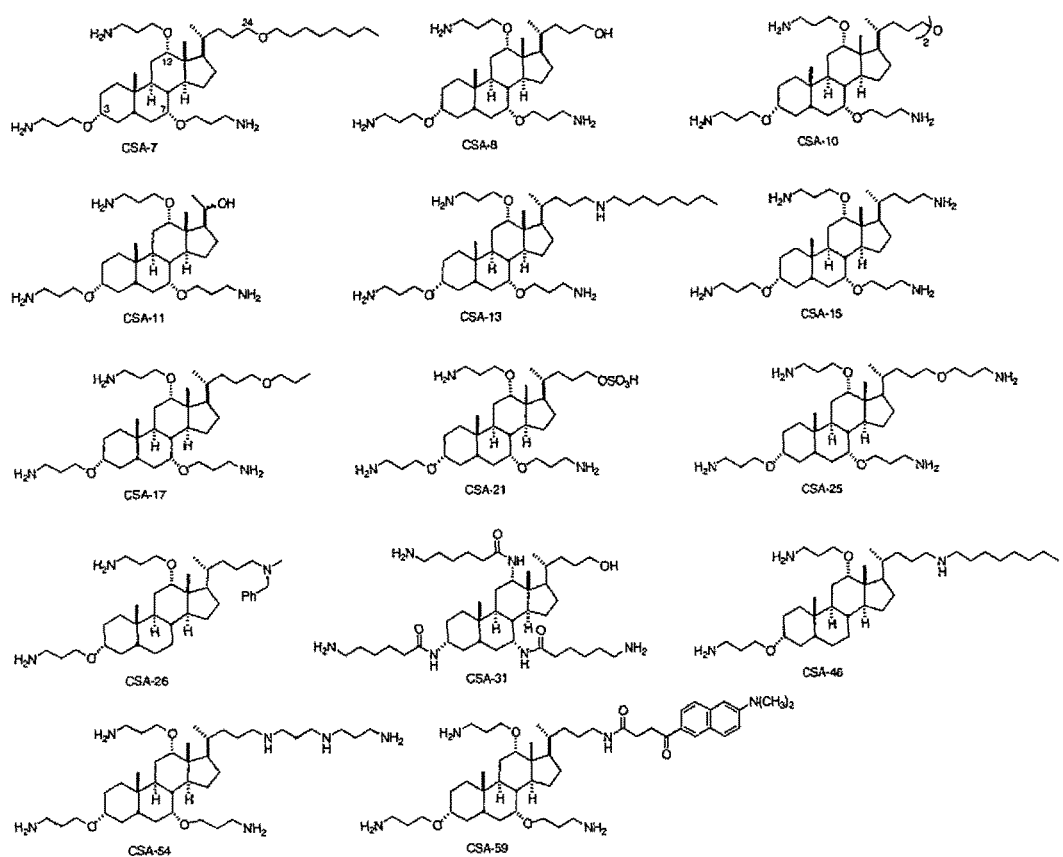
FIG. 18: shows structures of various CSAs.

Compounds 352-354 were dissolved in 50 mM phosphate buffered water (pH 2.0, 7.0 or 12.0) at approximately 10 mM concentrations. The structures of compounds 352-354 are given in FIG. 9. Decomposition of the compounds was observed via HPLC (cyano-silica column, 0.15% TFA water-acetonitrile gradient elution). Table 15 shows the stabilities (half-lives) of compounds 352-354 in phosphate buffer at room temperature, pH 2.0, pH 7.0 and pH 12.0. These compounds were used since they contain a chromophore that facilitated monitoring of decomposition by absorption methods common in the HPLC apparatus used.

At low pH, the amines are expected to be protonated and the compounds showed relative stability. At higher pH, the amines were less strongly protonated and became involved in ester hydrolysis. The γ-aminobutyric acid-derived compound was especially susceptible to hydrolysis, presumably yielding pyrrolidone. In general, the compounds are believed to hydrolyse to give cholic acid, choline or octanol, and glycine, beta-alanine, or pyrrolidone, depending on the particular compound.

Decomposition through ester hydrolysis yielded compounds that were less polar and easily separable from the starting compounds. Initially, only one benezene-containing decomposition product was observed; at longer reaction times, two other decomposition products were observed which presumably corresponded to sequential ester hydrolysis.

Example 15

This example includes a description of additional exemplary synthetic procedures for producing compounds of formula I. In one example, hydroxyl groups on cholic acid can be converted into amine groups as described in in Hsieh et al. (Synthesis and DNA Binding Properties of C3-, C12-, and C24-Substituted Amino-Steroids Derived from Bile Acids, Biorganic and Medicinal Chemistry, 1995, vol. 6, 823-838).

Compounds of formula I prepared as shown in the following Scheme.

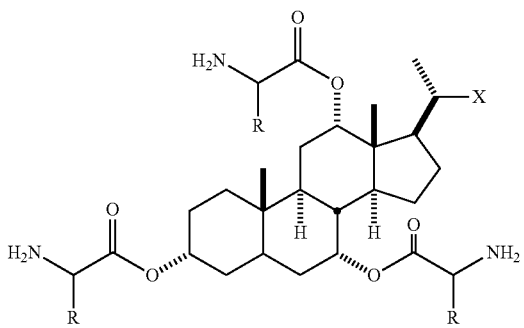

The R groups correspond to the side chain of any combination of amino acids (D or L)

Alterations in the stereochemistry within the steroid (AB ring juncture)

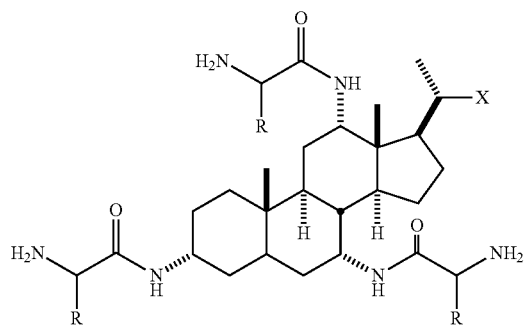

The R groups correspond to the side chain of any combination of amino acids (D or L)

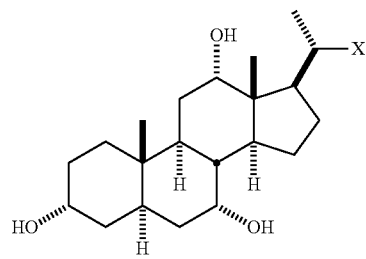

Alterations in the stereochemistry within the steroid (AB ring juncture)

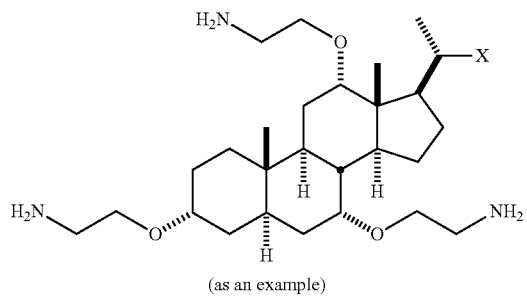

(as an example)

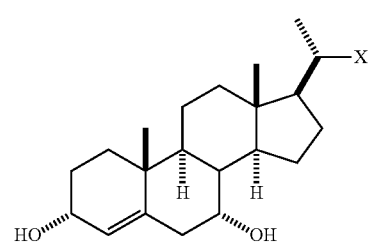

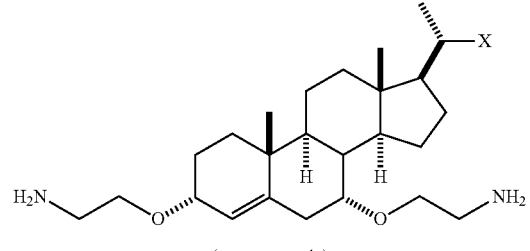

(as an example)

Alterations in
the stereochemistry within
the steroid (AB ring juncture)

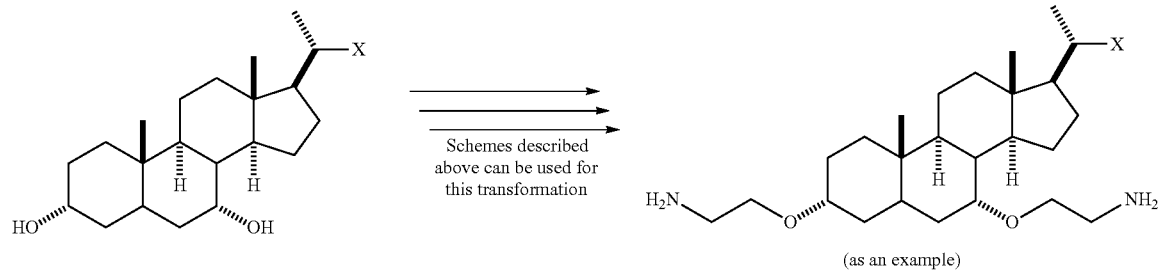

Alterations in
the stereochemistry within
the steroid (AB ring juncture)

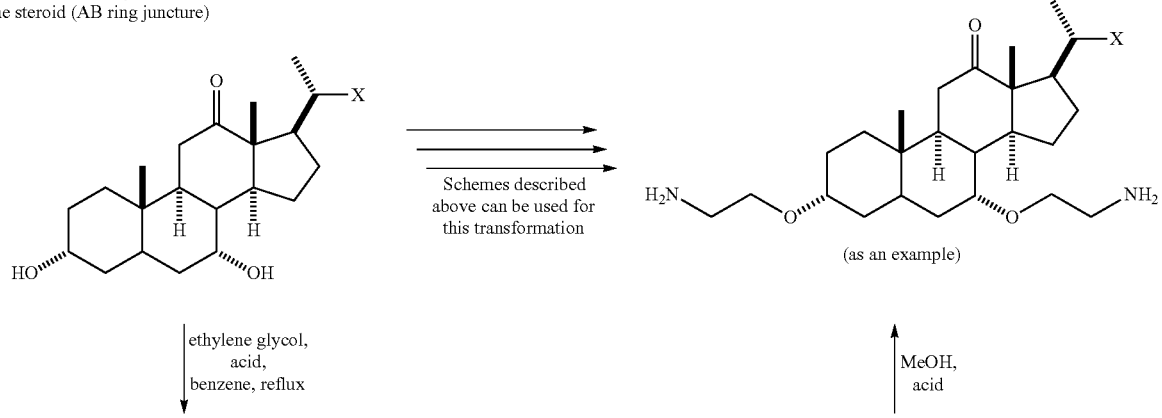

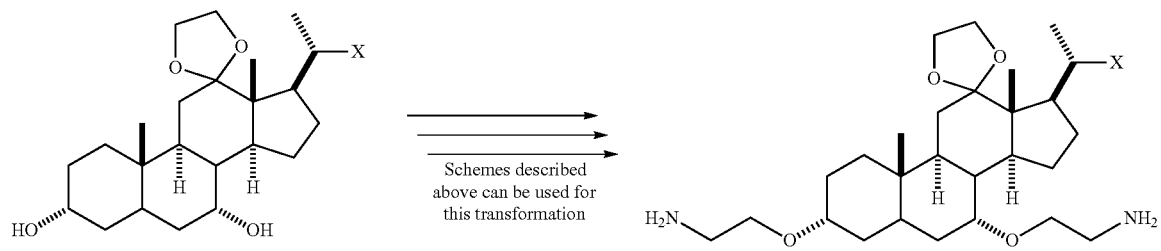

Description of the steroid starting materials shown above can be found in Dictionary of Steroids, Hill, R. R.; Kirk, D. N.; Makin, H. L. J.; Murphy. G. M., eds Chapman and Hall: New York, 1991.

What is claimed:

1. A method of detecting a tumor, cancer or neoplasia, or diagnosing a subject having or at risk of having a tumor, cancer or neoplasia, comprising:
   administering a detectably labeled cationic steroid antimicrobial (CSA) of formula V, or a pharmaceutically acceptable salt thereof, to the subject under conditions whereby the labeled CSA binds to cell membranes in cells of a tumor, cancer or neoplasia:

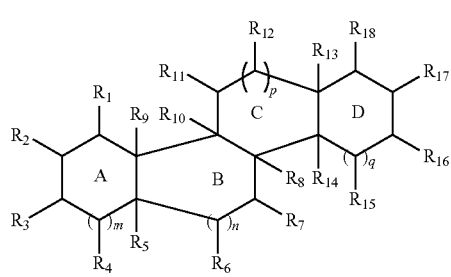

where:
  each of fused rings A, B, C, and D is independently saturated, or is fully or partially unsaturated, provided that at least two of A, B, C, and D are saturated, wherein rings A, B, C, and D form a ring system;
  each of m, n, p, and q is independently 0 or 1; and
  each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, substituted or unsubstituted (C1-C10) alkyl, (C1-C10) hydroxyalkyl, (C1-C10) alkyloxy-(C1-C10) alkyl, (C1-C10) alkylcarboxy-(C1-C10) alkyl, (C1-C10) alkylamino-(C1-C10) alkyl, (C1-C10) alkylamino-(C1-C10) alkylamino, (C1-C10) alkylamino-(C1-C10) alkylamino-(C1-C10) alkylamino, substituted or unsubstituted (C1-C10) aminoalkyl, substituted or unsubstituted aryl, substituted or unsubstituted arylamino-(C1-C10) alkyl, (C1-C10) haloalkyl, C2-C6 alkenyl, C2-C6 alkynyl, oxo, linking group attached to a second steroid, substituted or unsubstituted (C1-C10) aminoalkyloxy, substituted or unsubstituted (C1-C10) aminoalkyloxy-(C1-C10) alkyl, substituted or unsubstituted (C1-C10) aminoalkylcarboxy, substituted or unsubstituted (C1-C10) aminoalkylaminocarbonyl, substituted or unsubstituted (C1-C10) aminoalkylcarboxamido, $H_2N$—HC(Q5)-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyl oxy, (C1-C10) quaternary ammonium alkylcarboxy, and (C1-C10) guanidinoalkyl carboxy, where Q5 is a side chain of an amino acid, and P.G. is an amino protecting group, and
  each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, substituted or unsubstituted (C1-C10) alkyl, (C1-C10) hydroxyalkyl, (C1-C10) alkyloxy-(C1-C10) alkyl, substituted or unsubstituted (C1-C10) aminoalkyl, substituted or unsubstituted aryl, C1-C10 haloalkyl, C2-C6 alkenyl, C2-C6 alkynyl, oxo, linking group attached to a second steroid, substituted or unsubstituted (C1-C10) aminoalkyloxy, substituted or unsubstituted (C1-C10) aminoalkylcarboxy, substituted or unsubstituted (C1-C10) aminoalkylaminocarbonyl, $H_2N$—HC(Q5)-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy, where Q5 is a side chain of any amino acid, P.G. is an amino protecting group,
  provided that at least three of $R_6$, $R_7$, $R_{11}$, $R_{12}$, $R_{15}$, $R_{16}$, $R_{17}$, and $R_{18}$ are disposed on the same face of the ring system and are independently selected from the group consisting of substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, substituted or unsubstituted (C1-C10) aminoalkylcarboxy, substituted or unsubstituted arylamino-(C1-C10) alkyl, substituted or unsubstituted (C1-C10) aminoalkyloxy-(C1-C10) alkyl, substituted or unsubstituted (C1-C10) aminoalkylaminocarbonyl, (C1-C10) quaternary ammonium alkylcarboxy, $H_2NHC(Q5)$-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy, and wherein the detectably labeled CSA includes at least one radioisotope label selected from the group consisting of (i) a radioisotope of carbon, hydrogen, nitrogen, oxygen, or sulfur included in the structure of the CSA and (ii) a radioisotope of a metal or metal oxide covalently linked or conjugated to a basic site of the CSA selected from oxygen, sulfur, or nitrogen; and
detecting the presence, absence, or distribution of the detectably labeled CSA in a whole body, a particular region, a general area, a specific organ, a specific tissue, or a local portion of a region, organ, or tissue of the subject to ascertain the presence or absence of, a tumor, cancer or neoplasia, thereby detecting the tumor, cancer or neoplasia, or diagnosing the subject as having or not having a tumor, cancer or neoplasia.

2. A method of imaging a tumor, cancer or neoplasia in a subject having or at risk of having a tumor, cancer or neoplasia, comprising:
  administering a detectably labeled cationic steroid antimicrobial (CSA) of formula V, or a pharmaceutically acceptable salt thereof, to the subject under conditions whereby the labeled CSA binds to cell membranes in cells of a tumor, cancer or neoplasia:

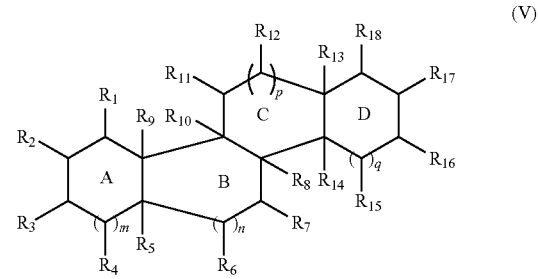

(V)

where:
  each of fused rings A, B, C, and D is independently saturated, or is fully or partially unsaturated, provided that at least two of A, B, C, and D are saturated, wherein rings A, B, C, and D form a ring system;
  each of m, n, p, and q is independently 0 or 1; and
  each of $R_1$ through $R_4$, $R_6$, $R_7$, $R_{11}$, $R_{12}$, $R_{15}$, $R_{16}$, $R_{17}$, and $R_{18}$ is independently selected from the group consisting of hydrogen, hydroxyl, substituted or unsubstituted (C1-C10) alkyl, (C1-C10) hydroxyalkyl, (C1-C10) alkyloxy-(C1-C10) alkyl, (C1-C10) alkylcarboxy-(C1-C10) alkyl, (C1-C10) alkylamino-(C1-C10) alkyl, (C1-C10) alkylamino-(C1-C10) alkylamino, (C1-C10) alkylamino-(C1-C10) alkylamino-(C1-C10) alkylamino, substituted or unsubstituted (C1-C10) aminoalkyl, substituted or unsubstituted aryl, substituted or unsubstituted arylamino-(C1-C10) alkyl, (C1-C10) haloalkyl, C2-C6 alkenyl, C2-C6 alkynyl, oxo, linking group attached to a second steroid, substituted or unsubstituted (C1-C10) aminoalkyloxy, substituted or unsubstituted (C1-C10) aminoalkyloxy-(C1-C10) alkyl, substituted or unsubstituted (C1-C10) aminoalkylcarboxy, substituted or unsubstituted (C1-C10) aminoalkylaminocarbonyl, substituted or unsubstituted (C1-C10) aminoalkylcarboxamido, $H_2N$—HC(Q5)-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyl oxy, (C1-C10) quaternary ammonium alkylcarboxy, and (C1-C10) guanidinoalkyl carboxy, where Q5 is a side chain of an amino acid, and P.G. is an amino protecting group, and each of $R_5$, $R_8$, $R_9$, $R_{10}$, $R_{13}$, and $R_{14}$ is independently: deleted when one of fused rings A, B, C, or D is unsaturated so as to complete the valency of the carbon atom at that site, or selected from the group consisting of hydrogen, hydroxyl, substituted or unsubstituted (C1-C10) alkyl, (C1-C10) hydroxyalkyl, (C1-C10) alkyloxy-(C1-C10) alkyl, substituted or unsubstituted (C1-C10) aminoalkyl, substituted or unsubstituted aryl, C1-C10 haloalkyl, C2-C6 alkenyl, C2-C6 alkynyl, oxo, linking group attached to a second steroid, substituted or unsubstituted (C1-C10) aminoalkyloxy, substituted or unsubstituted (C1-C10) aminoalkylcarboxy, substituted or unsubstituted (C1-C10) aminoalkylaminocarbonyl, $H_2N$—HC(Q5)-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy, where Q5 is a side chain of any amino acid, P.G. is an amino protecting group, provided that at least three of $R_6$, $R_7$, $R_{11}$, $R_{12}$, $R_{15}$, $R_{16}$, $R_{17}$, and $R_{18}$ are disposed on the same face of the ring system and are independently selected from the group consisting of substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, substituted or unsubstituted (C1-C10) aminoalkylcarboxy, substituted or unsubstituted aryl amino-(C1-C10) alkyl, substituted or unsubstituted (C1-C10) aminoalkyloxy-(C1-C10) alkyl, substituted or unsubstituted (C1-C10) aminoalkylaminocarbonyl, (C1-C10) quaternary ammonium alkylcarboxy, $H_2NHC(Q5)$-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkylcarboxy, and wherein the detectably labeled CSA includes at least one radioisotope label selected from the group consisting of (i) a radioisotope of carbon, hydrogen, nitrogen, oxygen, or sulfur included in the structure of the CSA and (ii) a radioisotope of a metal or metal oxide covalently linked or conjugated to a basic site of the CSA selected from oxygen, sulfur, or nitrogen; and imaging a whole body, a particular region, a general area, a specific organ, a specific tissue, or a local portion of a region, organ, or tissue of the subject to determine the presence, absence or distribution of the labeled CSA in the subject to ascertain the presence or absence of a tumor, cancer or neoplasia.

3. The method of claim 1 or 2, wherein the labeled CSA contains a plurality of cationic amine groups and the at least one radioisotope label is associated with one or more of the amine groups, and wherein the at least one radioisotope label is of one or more radioisotopes of: C, N, O, H, S, Cu, Fe, Ga, Ti, Sr, Y, Tc, In, Pm, Gd, Sm, Ho, Lu, Re, At, Bi or Ac.

4. The method of claim 1, wherein the radioisotope of a metal or metal oxide comprises a crystal.

5. The method of claim 1, wherein the radioisotope of a metal or metal oxide includes one or more of: gold, silver, copper, boron, manganese, gadolinium, iron, chromium, barium, europium, erbium, praseodynium, indium, or technetium.

6. The method of claim 1, wherein the radioisotope of a metal oxide comprises one or more of: Gd(III), Mn(II), Mn(III), Cr(II), Cr(III), Cu(II), Fe(III), Pr(III), Nd(III) Sm(III), Tb(III), Yb(III) Dy(III), Ho(III), Eu(II), Eu(III), or Er(III).

7. The method of claim 1 or 2, wherein the method detects the presence or absence, type, kind, location, extent, severity, or progression of the tumor, cancer or neoplasia.

8. The method of claim 1 or 2, wherein the detecting or imaging is performed using positron-emission tomography (PET), gamma-scintigraphy, computed tomography (CT), Computed Axial Tomography (CAT), or single photon emission tomography (SPECT).

9. The method of claim 1 or 2, wherein $R_{18}$ includes a substituted or unsubstituted (C1-C10) aminoalkyl and the following group bonded thereto:

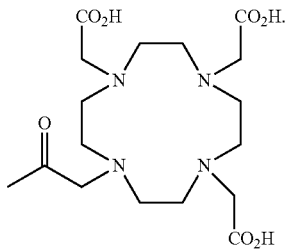 [SMILES: CC(=O)CN1CCN(CC(=O)O)CCN(CC(=O)O)CCN(CC(=O)O)CC1]

10. The method of claim 9, wherein the CSA is CSA-110:

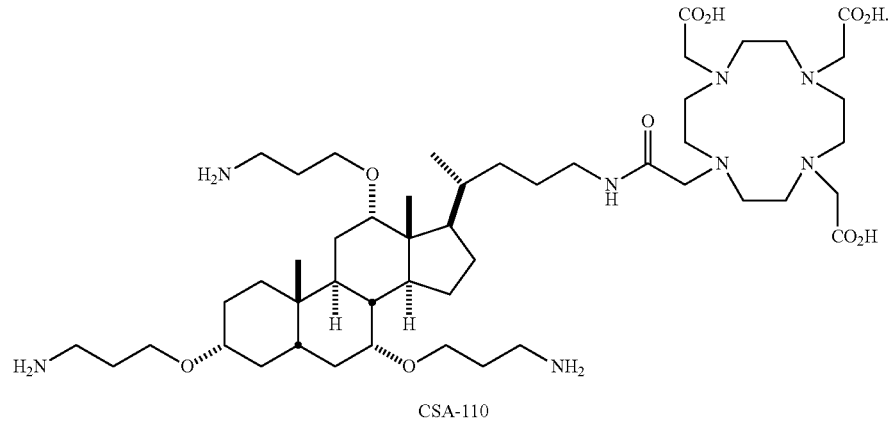

CSA-110

11. A method of detecting a tumor, cancer or neoplasia, or diagnosing a subject having or at risk of having a tumor, cancer or neoplasia, comprising:

administering a detectably labeled cationic steroid antimicrobial (CSA) of Formula (I), or a pharmaceutically acceptable salt thereof, to the subject under conditions whereby the labeled CSA binds to cell membranes in cells of a tumor, cancer or neoplasia:

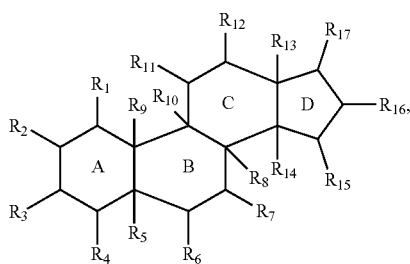

wherein:
fused rings A, B, C, and D are independently saturated or fully or partially unsaturated;

each of $R_1$ through $R_4$, $R_6$, $R_7$, $R_{11}$, $R_{12}$, $R_{15}$, $R_{16}$, and $R_{17}$ is independently selected from the group consisting of hydrogen, hydroxyl, a substituted or unsubstituted (C1-C10) alkyl, (C1-C10) hydroxyalkyl, (C1-C10) alkyloxy-(C1-C10) alkyl, (C1-C10) alkylcarboxy-(C1-C10) alkyl, (C1-C10) alkylamino-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkyl, a substituted or unsubstituted aryl, a substituted or unsubstituted arylamino-(C1-C10) alkyl, (C1-C10) haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkyloxy-(C1-C10) alkyl, a substituted or unsubstituted (C1-C10) aminoalkylcarboxy, a substituted or unsubstituted (C1-C10) aminoalkylaminocarbonyl, a substituted or unsubstituted (C1-C10) aminoalkylcarboxamido, $H_2N$—HC(Q5)-C(O)—O—, $H_2N$—HC(Q5)-C(O)—N(H)—, (C1-C10) azidoalkyloxy, (C1-C10) cyanoalkyloxy, P.G. —HN—HC(Q5)-C(O)—O—, (C1-C10) guanidinoalkyl oxy, (C1-C10) quaternary ammonium alkylcarboxy, and (C1-C10) guanidinoalkyl carboxy, where Q5 is a side chain of an amino acid, P.G. is an amino protecting group, and $R_5$, $R_8$, $R_9$, $R_{10}$, $R_{13}$, and $R_{14}$ is each independently deleted when one of fused rings A, B, C, or D is unsaturated so as to complete the valency of the carbon atom at that site, or selected from the group consisting of hydrogen, hydroxyl, a substituted or unsubstituted (C1-C10) alkyl, (C1-C10) hydroxyalkyl, (C1-C10) alkyloxy-(C1-C10) alkyl, a substituted or unsubstituted (C1-C10) aminoalkyl, a substituted or unsubstituted aryl, C1-C10 haloalkyl, C2-C6 alkenyl, C2-C6 alkynyl, oxo, a linking group attached to a second steroid, a substituted or unsubstituted (C1-C10) aminoalkyloxy, a substituted or unsubstituted (C1-C10) aminoalkylcarboxy, a substituted or unsubstituted (C1-C10) aminoalkylaminocarbonyl, $H_2N$—HC(Q5)-C(O)—O—, $H_2N$—HC(Q5)-C(O)—N(H)—, (C1-C10) azidoalkyloxy, (C1-C10) cyanoalkyloxy, P.G.—HN—HC(Q5)-C(O)—O—, (C1-C10) guanidinoalkyloxy, and (C1-C10) guanidinoalkyl carboxy, where Q5 is a side chain of an amino acid, P.G. is an amino protecting group, provided that at least two of $R_1$ through $R_4$, $R_6$, $R_7$, $R_{11}$, $R_{12}$, $R_{15}$, $R_{16}$, and $R_{17}$ are independently selected from the group consisting of a substituted or unsubstituted (C1-C10) aminoalkyloxy, (C1-C10) alkylcarboxy-(C1-C10) alkyl, (C1-C10) alkylamino-(C1-C10) alkylamino, (C1-C10) alkylamino-(C1-C10) alkylamino-(C1-C10) alkylamino, a substituted or unsubstituted (C1-C10) aminoalkylcarboxy, a substituted or unsubstituted arylamino-(C1-C10) alkyl, a substituted or unsubstituted (C1-C10) aminoalkyloxy-(C1-C10) alkyl, a substituted or unsubstituted (C1-C10) aminoalkylaminocarbonyl, (C1-C10) quaternary ammonium alkylcarboxy, $H_2N$—HC(Q5)-C(O)—O—, $H_2N$—HC(Q5)-C(O)—N(H)—, (C1-C10) azidoalkyloxy, (C1-C10) cyanoalkyloxy, P.G. —HN—HC(Q5)-C(O)—O—, (C1-C10) guanidinoalkyloxy, and (C1-C10) guanidinoalkylcarboxy, and provided that $R_{17}$ includes a substituted or unsubstituted (C1-C10) aminoalkyl and the following group bonded thereto:

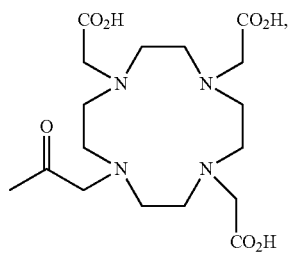 [SMILES: CC(=O)CN1CCN(CC(=O)O)CCN(CC(=O)O)CCN(CC(=O)O)CC1]

and wherein the detectably labeled CSA includes at least one radioisotope label selected from the group consisting of (i) a radioisotope of carbon, hydrogen, nitrogen, oxygen, or sulfur included in the structure of the CSA and (ii) a radioisotope of a metal or metal oxide covalently linked or conjugated to a basic site of the CSA selected from oxygen, sulfur, or nitrogen; and detecting the presence, absence, or distribution of the detectably labeled CSA in a whole body, a particular region, a general area, a specific organ, a specific tissue, or a local portion of a region, organ, or tissue of the subject to ascertain the presence or absence of a tumor, cancer or neoplasia, thereby detecting the tumor, cancer or neoplasia, or diagnosing the subject as having or not having a tumor, cancer or neoplasia.

12. The method of claim 11, wherein $R_{17}$ includes an amide group at the C24 position.

13. The method of claim 11, wherein the CSA is CSA-110:

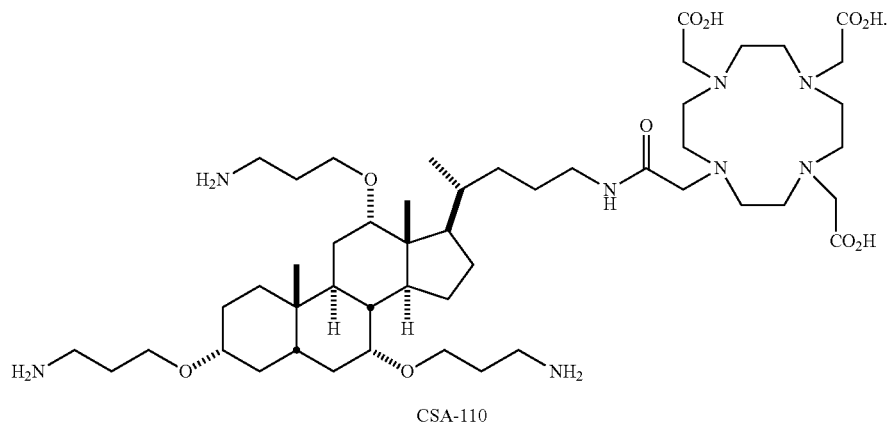
CSA-110

UNITED STATES PATENT AND TRADEMARK OFFICE
CERTIFICATE OF CORRECTION

PATENT NO. : 9,943,614 B2
APPLICATION NO. : 13/000010
DATED : April 17, 2018
INVENTOR(S) : Paul B. Savage Page 1 of 3

It is certified that error appears in the above-identified patent and that said Letters Patent is hereby corrected as shown below:

On the Title Page

Page 3
Item (56), References Cited, OTHER PUBLICATIONS, change "Melinda Yin, et al; "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan 1, 2002." to —Melinda Yin, et al; "Antiangiogenic Treatment Delays Chondrocyte Maturation and Bone Formation During Lim Skeletogenesis", Journal of Bone and Mineral Research, American Society for Bone and Mineral Research, New York, NY, US, vol. 17, No. 1, Jan 1, 2002.—

Item (56), References Cited, OTHER PUBLICATIONS, change "Fritsch et al, "In Vitro Activity of Nine Developmental Cationic Steroid Compounds (Ceragenins) against Clnical Isolates of Clostridium difficile," The 46th Interscience Conference on Anti-microbial Agents and Chemotherapy, Sep. 27, 2006, pp. 1-1." to —Fritsch et al, "In Vitro Activity of Nine Developmental Cationic Steroid Compounds (Ceragenins) against Clinical Isolates of Clostridium difficile," The 46th Interscience Conference on Anti-microbial Agents and Chemotherapy, Sep. 27, 2006, pp. 1-1.—

In the Specification

Column 1
Line 35, remove "while"

Column 4
Line 49, change "avidinfbiotin" to —avidin/biotin—

Column 6
Line 22, change "incltide" to —include—
Line 48, change "include" to —includes—

Signed and Sealed this
Eighteenth Day of December, 2018

Andrei Iancu
*Director of the United States Patent and Trademark Office*

CERTIFICATE OF CORRECTION (continued)
U.S. Pat. No. 9,943,614 B2

Column 8
Line 3, change "espophagug" to —esophagus—
Line 4, change "rectum)" to —rectum—

Column 9
Line 24, change "succinly" to —succinyl—
Line 30, remove "a"
Line 32, change "animal" to —animals—

Column 13
Line 44, change "a" to —an—

Column 14
Line 53, change "is" to —are—

Column 19
Line 2, change "are" to —that are—
Line 20, change "are" to —that are—
Line 25, remove first instance of "at least two of"

Column 50
Line 45, remove first instance of "lung"

Column 51
Line 34, change "synthestic" to —synthetic—

Column 54
Line 42, change "followed" to —following—

Column 60
Line 13, change "synthestic" to —synthetic—

Column 61
Line 59, change "synthestic" to —synthetic—

Column 65
Line 63, change "with twice" to —twice with—

Column 66
Line 17, change "synthestic" to —synthetic—

Column 69
Line 4, change "synthestic" to —synthetic—

Column 70
Line 22, change "synthestic" to —synthetic—

Column 71
Line 39, change "synthestic" to —synthetic—

Column 75
Line 4, change "synthestic" to —synthetic—

Column 78
Line 27, change "synthestic" to —synthetic—
Line 55, change "synthestic" to —synthetic—

Column 81
Line 10, change "desire" to —desired—